(12) United States Patent
Schneider et al.

(10) Patent No.: US 10,597,695 B2
(45) Date of Patent: Mar. 24, 2020

(54) MODIFIED CREATINASE

(71) Applicant: Radiometer Medical ApS, Brønshøj (DK)

(72) Inventors: Palle Schneider, Espergaerde (DK); Jens Østergaard, Lyngby (DK); Thomas Steen Hansen, Herlev (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 208 days.

(21) Appl. No.: 15/553,660

(22) PCT Filed: Feb. 23, 2016

(86) PCT No.: PCT/EP2016/053760
§ 371 (c)(1),
(2) Date: Aug. 25, 2017

(87) PCT Pub. No.: WO2016/135136
PCT Pub. Date: Sep. 1, 2016

(65) Prior Publication Data
US 2018/0340207 A1      Nov. 29, 2018

(30) Foreign Application Priority Data
Feb. 27, 2015   (DK) .................................. 2015 00114

(51) Int. Cl.
| | | |
|---|---|---|
| *C12N 9/78* | (2006.01) | |
| *C12Q 1/34* | (2006.01) | |
| *C12N 1/20* | (2006.01) | |
| *C12N 15/00* | (2006.01) | |
| *C07H 21/04* | (2006.01) | |
| *C12N 9/86* | (2006.01) | |

(52) U.S. Cl.
CPC ................. *C12Q 1/34* (2013.01); *C12N 9/86* (2013.01); *C12N 15/00* (2013.01)

(58) Field of Classification Search
None
See application file for complete search history.

(56) References Cited

U.S. PATENT DOCUMENTS 6,080,553 A * 6/2000 Sogabe .................... C12Q 1/34
                                                                435/18

FOREIGN PATENT DOCUMENTS

| DE | 195 36 506 A1 | 4/1996 |
|---|---|---|
| EP | 0 790 303 A1 | 8/1997 |
| EP | 1 134 284 A1 | 9/2001 |
| JP | H10-174585 | 6/1998 |
| JP | 2008-516235 | 5/2008 |
| WO | WO 2006/042001 A2 | 4/2006 |

OTHER PUBLICATIONS

Furukawa. Q9RHU9. UnitProtKB. Oct. 2013.*
Wyss. Creatine and Creatinine Metabolism. Physiological Reviews. vol. 80, No. 3, Jul. 2000.*
Heldermon. Site-directed mutation of conserved cysteine residues does not inactivate the *Streptococcus pyogenes* hyaluronan synthase. Glycobiology, vol. 11, Issue 12, Dec. 1, 2001, pp. 1017-1024.*
Berberich, Jason A. et al., "A stable three-enzyme creatinine biosensor. 1. Impact of structure, function and environment on PEGylated and immobilized sarcosine oxidase," Acta Biomaterials I, pp. 173-181 (2005).
English language abstract of DE 195 36 506 A1, Apr. 4, 1996.
International Search Report of International Application No. PCT/EP2016/053760, dated May 4, 2016.
Written Opinion of the International Searching Authority for International Application No. PCT/EP3016.053760.

* cited by examiner

*Primary Examiner* — Yong D Pak
(74) *Attorney, Agent, or Firm* — Finnegan, Henderson, Farabow, Garrett & Dunner, LLP

(57) ABSTRACT

The invention relates to a mutant polypeptide having *creatine amidinohydrolase* activity, where the polypeptide both retains thermostable activity in the presence of reagents that modify thiol groups. The invention further relates to methods for producing the mutant polypeptide; and to a sensor comprising the mutant polypeptide for use in the measurement of creatinine in samples of physiological fluids. Additionally, the invention teaches how to use the mutant polypeptide to enhance the life-time of a creatinine sensor, and a method for producing the sensor.

15 Claims, 2 Drawing Sheets

Specification includes a Sequence Listing.

SEQUENCE LISTING

```
<160> NUMBER OF SEQ ID NOS: 48

<210> SEQ ID NO 1
<211> LENGTH: 1215
<212> TYPE: DNA
<213> ORGANISM: Alcaligenes strain:KS-85
<220> FEATURE:
<221> NAME/KEY: CDS
<222> LOCATION: (1)..(1215)
<223> OTHER INFORMATION: AB016788.1 Alcaligenes sp. strain:KS-85. gene
      encoding creatine amidinohydrolase [Q9RHU9]

<400> SEQUENCE: 1 atg act gac gac atg ttg cac gtg atg aaa tgg cac aac ggc gaa aaa        48
Met Thr Asp Asp Met Leu His Val Met Lys Trp His Asn Gly Glu Lys
1               5                   10                  15 gat tat tcg ccg ttt tcg gat gcc gag atg acc cgc cgc caa aac gac        96
Asp Tyr Ser Pro Phe Ser Asp Ala Glu Met Thr Arg Arg Gln Asn Asp
                20                  25                  30 gtt cgc ggc tgg atg gcc aag aac aat gtc gat gcg gcg ctg ttc acc       144
Val Arg Gly Trp Met Ala Lys Asn Asn Val Asp Ala Ala Leu Phe Thr
            35                  40                  45 tct tat cac tgc atc aac tac tat tcc ggc tgg ctg tac tgc tat ttc       192
Ser Tyr His Cys Ile Asn Tyr Tyr Ser Gly Trp Leu Tyr Cys Tyr Phe
        50                  55                  60 gga cgc aag tac ggc atg gtc atc gac cac aac aac gcc acg acg att       240
Gly Arg Lys Tyr Gly Met Val Ile Asp His Asn Asn Ala Thr Thr Ile
65                  70                  75                  80 tcg gcc ggc atc gac ggc ggc cag ccc tgg cgc cgc agc ttc ggc gac       288
Ser Ala Gly Ile Asp Gly Gly Gln Pro Trp Arg Arg Ser Phe Gly Asp
                85                  90                  95 aac atc acc tac acc gac tgg cgc cgc gac aat ttc tat cgc gcc gtg       336
Asn Ile Thr Tyr Thr Asp Trp Arg Arg Asp Asn Phe Tyr Arg Ala Val
                100                 105                 110 cgc cag ctg acc acg ggc gcc aag cgc atc ggc atc gag ttc gac cac       384
Arg Gln Leu Thr Thr Gly Ala Lys Arg Ile Gly Ile Glu Phe Asp His
            115                 120                 125 gtc aat ctc gac ttc cgc cgc cag ctc gag gaa gcc cta ccg ggc gtc       432
Val Asn Leu Asp Phe Arg Arg Gln Leu Glu Glu Ala Leu Pro Gly Val
        130                 135                 140 gag ttc gtc gac atc agc cag ccc tcg atg tgg atg cgc acc atc aag       480
Glu Phe Val Asp Ile Ser Gln Pro Ser Met Trp Met Arg Thr Ile Lys
145                 150                 155                 160
```

-continued

| | | |
|---|---|---|
| tcg ctc gaa gag cag aag ctg atc cgc gaa ggc gcc cgc gtg tgt gac<br>Ser Leu Glu Glu Gln Lys Leu Ile Arg Glu Gly Ala Arg Val Cys Asp<br>165　　　　　　　　　170　　　　　　　　　175 | 528 |
| gtc ggc ggc gcg gcc tgc gcg gct gcc atc aag gcc ggc gtg ccc gag<br>Val Gly Gly Ala Ala Cys Ala Ala Ala Ile Lys Ala Gly Val Pro Glu<br>180　　　　　　　　　185　　　　　　　　　190 | 576 |
| cat gaa gtg gcg atc gcc acc acc aat gcg atg atc cgc gag atc gcc<br>His Glu Val Ala Ile Ala Thr Thr Asn Ala Met Ile Arg Glu Ile Ala<br>195　　　　　　　　　200　　　　　　　　　205 | 624 |
| aaa tcg ttc ccc ttc gtg gag ctg atg gac acc tgg acc tgg ttc cag<br>Lys Ser Phe Pro Phe Val Glu Leu Met Asp Thr Trp Thr Trp Phe Gln<br>210　　　　　　　　　215　　　　　　　　　220 | 672 |
| tcg ggc atc aac acc gac ggc gcg cac aat ccg gtc acc aac cgc atc<br>Ser Gly Ile Asn Thr Asp Gly Ala His Asn Pro Val Thr Asn Arg Ile<br>225　　　　　　　　　230　　　　　　　　　235　　　　　　　　　240 | 720 |
| gtg caa tcc ggc gac atc ctt tcg ctc aac acc ttc ccg atg atc ttc<br>Val Gln Ser Gly Asp Ile Leu Ser Leu Asn Thr Phe Pro Met Ile Phe<br>245　　　　　　　　　250　　　　　　　　　255 | 768 |
| ggc tac tac acc gcg ctg gag cgc acg ctg ttc tgc gac cat gtc gat<br>Gly Tyr Tyr Thr Ala Leu Glu Arg Thr Leu Phe Cys Asp His Val Asp<br>260　　　　　　　　　265　　　　　　　　　270 | 816 |
| gac gcc agc ctc gac atc tgg gag aag aac gtg gcc gtg cat cgc cgc<br>Asp Ala Ser Leu Asp Ile Trp Glu Lys Asn Val Ala Val His Arg Arg<br>275　　　　　　　　　280　　　　　　　　　285 | 864 |
| ggg ctc gag ctg atc aag ccg ggc gcg cgc tgc aag gac atc gcc atc<br>Gly Leu Glu Leu Ile Lys Pro Gly Ala Arg Cys Lys Asp Ile Ala Ile<br>290　　　　　　　　　295　　　　　　　　　300 | 912 |
| gag ctc aac gag atg tac cgc gag tgg gac ctg ctg aag tac cgc tcc<br>Glu Leu Asn Glu Met Tyr Arg Glu Trp Asp Leu Leu Lys Tyr Arg Ser<br>305　　　　　　　　　310　　　　　　　　　315　　　　　　　　　320 | 960 |
| ttc ggc tat ggc cac tcc ttc ggc gtg ctg tgc cac tac tac ggt cgc<br>Phe Gly Tyr Gly His Ser Phe Gly Val Leu Cys His Tyr Tyr Gly Arg<br>325　　　　　　　　　330　　　　　　　　　335 | 1008 |
| gag gcg ggc gtg gag ctg cgc gag gac atc gac acc gag ctg aag ccc<br>Glu Ala Gly Val Glu Leu Arg Glu Asp Ile Asp Thr Glu Leu Lys Pro<br>340　　　　　　　　　345　　　　　　　　　350 | 1056 |
| ggc atg gtg gtc tcc atg gag ccg atg gtg atg ctg ccg gag ggc atg<br>Gly Met Val Val Ser Met Glu Pro Met Val Met Leu Pro Glu Gly Met<br>355　　　　　　　　　360　　　　　　　　　365 | 1104 |
| ccc ggt gcc ggc ggc tat cgc gag cac gac atc ctg atc gtc ggg gag<br>Pro Gly Ala Gly Gly Tyr Arg Glu His Asp Ile Leu Ile Val Gly Glu<br>370　　　　　　　　　375　　　　　　　　　380 | 1152 |
| gac ggt gcc gag aac atc acc ggc ttc ccg ttc ggt ccg gaa cac aac<br>Asp Gly Ala Glu Asn Ile Thr Gly Phe Pro Phe Gly Pro Glu His Asn<br>385　　　　　　　　　390　　　　　　　　　395　　　　　　　　　400 | 1200 |
| atc atc cgc aac tga<br>Ile Ile Arg Asn | 1215 |

<210> SEQ ID NO 2
<211> LENGTH: 404
<212> TYPE: PRT
<213> ORGANISM: Alcaligenes strain:KS-85

<400> SEQUENCE: 2

Met Thr Asp Asp Met Leu His Val Met Lys Trp His Asn Gly Glu Lys
1               5                   10                  15

Asp Tyr Ser Pro Phe Ser Asp Ala Glu Met Thr Arg Arg Gln Asn Asp
            20                  25                  30

Val Arg Gly Trp Met Ala Lys Asn Asn Val Asp Ala Ala Leu Phe Thr

```
            35                  40                  45
Ser Tyr His Cys Ile Asn Tyr Tyr Ser Gly Trp Leu Tyr Cys Tyr Phe
 50                  55                  60

Gly Arg Lys Tyr Gly Met Val Ile Asp His Asn Asn Ala Thr Thr Ile
 65                  70                  75                  80

Ser Ala Gly Ile Asp Gly Gly Gln Pro Trp Arg Arg Ser Phe Gly Asp
                 85                  90                  95

Asn Ile Thr Tyr Thr Asp Trp Arg Arg Asp Asn Phe Tyr Arg Ala Val
            100                 105                 110

Arg Gln Leu Thr Thr Gly Ala Lys Arg Ile Gly Ile Glu Phe Asp His
            115                 120                 125

Val Asn Leu Asp Phe Arg Arg Gln Leu Glu Glu Ala Leu Pro Gly Val
130                 135                 140

Glu Phe Val Asp Ile Ser Gln Pro Ser Met Trp Met Arg Thr Ile Lys
145                 150                 155                 160

Ser Leu Glu Glu Gln Lys Leu Ile Arg Glu Gly Ala Arg Val Cys Asp
                165                 170                 175

Val Gly Gly Ala Ala Cys Ala Ala Ile Lys Ala Gly Val Pro Glu
                180                 185                 190

His Glu Val Ala Ile Ala Thr Thr Asn Ala Met Ile Arg Glu Ile Ala
            195                 200                 205

Lys Ser Phe Pro Phe Val Glu Leu Met Asp Thr Trp Thr Trp Phe Gln
210                 215                 220

Ser Gly Ile Asn Thr Asp Gly Ala His Asn Pro Val Thr Asn Arg Ile
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
                260                 265                 270

Asp Ala Ser Leu Asp Ile Trp Glu Lys Asn Val Ala Val His Arg Arg
            275                 280                 285

Gly Leu Glu Leu Ile Lys Pro Gly Ala Arg Cys Lys Asp Ile Ala Ile
            290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Asp Thr Glu Leu Lys Pro
                340                 345                 350

Gly Met Val Val Ser Met Glu Pro Met Val Met Leu Pro Glu Gly Met
            355                 360                 365

Pro Gly Ala Gly Gly Tyr Arg Glu His Asp Ile Leu Ile Val Gly Glu
            370                 375                 380

Asp Gly Ala Glu Asn Ile Thr Gly Phe Pro Phe Gly Pro Glu His Asn
385                 390                 395                 400

Ile Ile Arg Asn

<210> SEQ ID NO 3
<211> LENGTH: 404
<212> TYPE: PRT
<213> ORGANISM: Alcaligenes sp.
<220> FEATURE:
<221> NAME/KEY: mat_peptide
<222> LOCATION: (1)..(404)
<223> OTHER INFORMATION: Mutant creatine amidinohydrolase _Alcaligenes
``` sp. Q9RHU9 with C175A+C299A substitutions

<400> SEQUENCE: 3

```
Met Thr Asp Asp Met Leu His Val Met Lys Trp His Asn Gly Glu Lys
1               5                   10                  15

Asp Tyr Ser Pro Phe Ser Asp Ala Glu Met Thr Arg Arg Gln Asn Asp
            20                  25                  30

Val Arg Gly Trp Met Ala Lys Asn Asn Val Asp Ala Ala Leu Phe Thr
        35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Asp His Asn Asn Ala Thr Thr Ile
65              70                  75                  80

Ser Ala Gly Ile Asp Gly Gly Gln Pro Trp Arg Arg Ser Phe Gly Asp
            85                  90                  95

Asn Ile Thr Tyr Thr Asp Trp Arg Arg Asp Asn Phe Tyr Arg Ala Val
            100                 105                 110

Arg Gln Leu Thr Thr Gly Ala Lys Arg Ile Gly Ile Glu Phe Asp His
        115                 120                 125

Val Asn Leu Asp Phe Arg Arg Gln Leu Glu Glu Ala Leu Pro Gly Val
130                 135                 140

Glu Phe Val Asp Ile Ser Gln Pro Ser Met Trp Met Arg Thr Ile Lys
145                 150                 155                 160

Ser Leu Glu Glu Gln Lys Leu Ile Arg Glu Gly Ala Arg Val Ala Asp
                165                 170                 175

Val Gly Gly Ala Ala Cys Ala Ala Ile Lys Ala Gly Val Pro Glu
            180                 185                 190

His Glu Val Ala Ile Ala Thr Thr Asn Ala Met Ile Arg Glu Ile Ala
        195                 200                 205

Lys Ser Phe Pro Phe Val Glu Leu Met Asp Thr Trp Thr Trp Phe Gln
210                 215                 220

Ser Gly Ile Asn Thr Asp Gly Ala His Asn Pro Val Thr Asn Arg Ile
225                 230                 235                 240

Val Gln Ser Gly Asp Ile Leu Ser Leu Asn Thr Phe Pro Met Ile Phe
            245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
        275                 280                 285

Gly Leu Glu Leu Ile Lys Pro Gly Ala Arg Ala Lys Asp Ile Ala Ile
        290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
            325                 330                 335

Glu Ala Gly Val Glu Leu Arg Glu Asp Ile Asp Thr Glu Leu Lys Pro
            340                 345                 350

Gly Met Val Val Ser Met Glu Pro Met Val Met Leu Pro Glu Gly Met
        355                 360                 365

Pro Gly Ala Gly Gly Tyr Arg Glu His Asp Ile Leu Ile Val Gly Glu
370                 375                 380

Asp Gly Ala Glu Asn Ile Thr Gly Phe Pro Phe Gly Pro Glu His Asn
385                 390                 395                 400
```

Ile Ile Arg Asn

<210> SEQ ID NO 4
<211> LENGTH: 404
<212> TYPE: PRT
<213> ORGANISM: Alcaligenes sp.
<220> FEATURE:
<221> NAME/KEY: mat_peptide
<222> LOCATION: (1)..(404)
<223> OTHER INFORMATION: Mutant creatine amidinohydrolase _Alcaligenes
      sp. Q9RHU9 with C175A+C299A+C268L substitutions

<400> SEQUENCE: 4

Met Thr Asp Asp Met Leu His Val Met Lys Trp His Asn Gly Glu Lys
1               5                   10                  15

Asp Tyr Ser Pro Phe Ser Asp Ala Glu Met Thr Arg Arg Gln Asn Asp
                20                  25                  30

Val Arg Gly Trp Met Ala Lys Asn Asn Val Asp Ala Ala Leu Phe Thr
            35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Asp His Asn Asn Ala Thr Thr Ile
65                  70                  75                  80

Ser Ala Gly Ile Asp Gly Gly Gln Pro Trp Arg Arg Ser Phe Gly Asp
                85                  90                  95

Asn Ile Thr Tyr Thr Asp Trp Arg Arg Asp Asn Phe Tyr Arg Ala Val
            100                 105                 110

Arg Gln Leu Thr Thr Gly Ala Lys Arg Ile Gly Ile Glu Phe Asp His
            115                 120                 125

Val Asn Leu Asp Phe Arg Arg Gln Leu Glu Glu Ala Leu Pro Gly Val
    130                 135                 140

Glu Phe Val Asp Ile Ser Gln Pro Ser Met Trp Met Arg Thr Ile Lys
145                 150                 155                 160

Ser Leu Glu Glu Gln Lys Leu Ile Arg Glu Gly Ala Arg Val Ala Asp
                165                 170                 175

Val Gly Gly Ala Ala Cys Ala Ala Ile Lys Ala Gly Val Pro Glu
            180                 185                 190

His Glu Val Ala Ile Ala Thr Thr Asn Ala Met Ile Arg Glu Ile Ala
    195                 200                 205

Lys Ser Phe Pro Phe Val Glu Leu Met Asp Thr Trp Thr Trp Phe Gln
210                 215                 220

Ser Gly Ile Asn Thr Asp Gly Ala His Asn Pro Val Thr Asn Arg Ile
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Leu Asp His Val Asp
            260                 265                 270

Asp Ala Ser Leu Asp Ile Trp Glu Lys Asn Val Ala Val His Arg Arg
            275                 280                 285

Gly Leu Glu Leu Ile Lys Pro Gly Ala Arg Ala Lys Asp Ile Ala Ile
    290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Asp Thr Glu Leu Lys Pro

```
              340                 345                 350
Gly Met Val Val Ser Met Glu Pro Met Val Met Leu Pro Glu Gly Met
            355                 360                 365

Pro Gly Ala Gly Gly Tyr Arg Glu His Asp Ile Leu Ile Val Gly Glu
370                 375                 380

Asp Gly Ala Glu Asn Ile Thr Gly Phe Pro Phe Gly Pro Glu His Asn
385                 390                 395                 400

Ile Ile Arg Asn

<210> SEQ ID NO 5
<211> LENGTH: 1203
<212> TYPE: DNA
<213> ORGANISM: Ochrobactrum anthropi
<220> FEATURE:
<221> NAME/KEY: CDS
<222> LOCATION: (1)..(1203)
<223> OTHER INFORMATION: AIK40910.1 Ochrobactrum anthropi gene encoding
      creatine amidinohydrolase [A0A076WGB5]

<400> SEQUENCE: 5
```

| | | | | | | | | | | | | | | | | |
|---|---|---|---|---|---|---|---|---|---|---|---|---|---|---|---|---|
| atg | ctg | cat | gtc | atg | aaa | tgg | cac | aat | ggc | gag | aag | gac | tat | tcg | ccg | 48 |
| Met | Leu | His | Val | Met | Lys | Trp | His | Asn | Gly | Glu | Lys | Asp | Tyr | Ser | Pro | |
| 1 | | | | 5 | | | | | 10 | | | | | 15 | | |

```
ttc tcc gag gcc gaa atg acc cgc cgt cag aac gac gtg cgg ggc tgg      96
Phe Ser Glu Ala Glu Met Thr Arg Arg Gln Asn Asp Val Arg Gly Trp
             20                  25                  30 atg gcc aag aac gac gtc gat gcg gcg ctg ttc acc tcc tac cat tgc     144
Met Ala Lys Asn Asp Val Asp Ala Ala Leu Phe Thr Ser Tyr His Cys
         35                  40                  45 atc aac tat tat tcg ggt tgg ctg tac tgc tat ttc ggc cgc aaa tac     192
Ile Asn Tyr Tyr Ser Gly Trp Leu Tyr Cys Tyr Phe Gly Arg Lys Tyr
     50                  55                  60 ggc atg gtc atc gac cac aac aag gcg acc acc atc tcc gcc ggc atc     240
Gly Met Val Ile Asp His Asn Lys Ala Thr Thr Ile Ser Ala Gly Ile
65                  70                  75                  80 gat ggc ggc cag ccc tgg cgg cgc agc ttc ggc gac aac atc acc tat     288
Asp Gly Gly Gln Pro Trp Arg Arg Ser Phe Gly Asp Asn Ile Thr Tyr
                 85                  90                  95 acc gac tgg cgc cgg gac aat ttc tat cag gca gtg cgc cag ttg acg     336
Thr Asp Trp Arg Arg Asp Asn Phe Tyr Gln Ala Val Arg Gln Leu Thr
            100                 105                 110 aag ggc gcc aag cgc gtc ggc atc gaa ttc gat cat gtc tcg ctc gac     384
Lys Gly Ala Lys Arg Val Gly Ile Glu Phe Asp His Val Ser Leu Asp
        115                 120                 125 ttc cgc cgc cag ctc gag gaa gcg ctg ccg ggc gtc gag ttc gtg gat     432
Phe Arg Arg Gln Leu Glu Glu Ala Leu Pro Gly Val Glu Phe Val Asp
    130                 135                 140 gtc ggc cag ccc tcg atg tgg atg cgc acg atc aag tcg gcg gag gag     480
Val Gly Gln Pro Ser Met Trp Met Arg Thr Ile Lys Ser Ala Glu Glu
145                 150                 155                 160 cag aag ctg atc cgc gaa gga gcg cgc gtg tgt gac gta ggc ggt gcg     528
Gln Lys Leu Ile Arg Glu Gly Ala Arg Val Cys Asp Val Gly Gly Ala
                165                 170                 175 gcc tgc gcg gcg gcg gtc aag gct ggc gta ccg gaa cat gaa gtc gcc     576
Ala Cys Ala Ala Ala Val Lys Ala Gly Val Pro Glu His Glu Val Ala
            180                 185                 190 atc gcc acc acc aat gca atg gtc cgc gag atc gcc aag tcg ttt ccg     624
Ile Ala Thr Thr Asn Ala Met Val Arg Glu Ile Ala Lys Ser Phe Pro
        195                 200                 205 ttc gtc gag ctg atg gac acc tgg acc tgg ttc cag tcg ggc atc aac     672
Phe Val Glu Leu Met Asp Thr Trp Thr Trp Phe Gln Ser Gly Ile Asn
```

-continued

```
                Phe Val Glu Leu Met Asp Thr Trp Thr Trp Phe Gln Ser Gly Ile Asn
                210                 215                 220 acc gac ggc gcc cac aac ccg gtc aca aac cgc atc gtg cag tcg ggc      720
Thr Asp Gly Ala His Asn Pro Val Thr Asn Arg Ile Val Gln Ser Gly
225                 230                 235                 240 gat atc ctt tcg ctc aat acc ttc ccg atg atc ttc ggc tat tac acc      768
Asp Ile Leu Ser Leu Asn Thr Phe Pro Met Ile Phe Gly Tyr Tyr Thr
                245                 250                 255 gcg ctc gag cgg acg ctg ttc tgc gac cat gtc gac gat gcc agc ctc      816
Ala Leu Glu Arg Thr Leu Phe Cys Asp His Val Asp Asp Ala Ser Leu
            260                 265                 270 gat atc tgg gag aag aac gtg gcc gtc cac cgt cgc ggg ctg gag ctg      864
Asp Ile Trp Glu Lys Asn Val Ala Val His Arg Arg Gly Leu Glu Leu
        275                 280                 285 atc aag ccg ggc gcc cgc tgc aag gac atc gcg ctc gaa ctc aac gac      912
Ile Lys Pro Gly Ala Arg Cys Lys Asp Ile Ala Leu Glu Leu Asn Asp
    290                 295                 300 atg tat cgc gag tgg gac ctg ctg aag tac cgt tcg ttc ggc tac ggc      960
Met Tyr Arg Glu Trp Asp Leu Leu Lys Tyr Arg Ser Phe Gly Tyr Gly
305                 310                 315                 320 cat tcc ttc ggc gtg ctg tgc cac tac tat ggc cgc gag gcc ggg gtg     1008
His Ser Phe Gly Val Leu Cys His Tyr Tyr Gly Arg Glu Ala Gly Val
                325                 330                 335 gaa ctg cgc gag gac atc gac acg gtg ctg gag ccc ggc atg gtg gtt     1056
Glu Leu Arg Glu Asp Ile Asp Thr Val Leu Glu Pro Gly Met Val Val
            340                 345                 350 tcc atg gag ccg atg gtg atg ctg ccg gaa ggc gcg ccg ggc gcc ggc     1104
Ser Met Glu Pro Met Val Met Leu Pro Glu Gly Ala Pro Gly Ala Gly
        355                 360                 365 ggc tat cgc gag cac gac atc ctg atc gtc aag gag gac agc gcc gag     1152
Gly Tyr Arg Glu His Asp Ile Leu Ile Val Lys Glu Asp Ser Ala Glu
    370                 375                 380 aac atc acc ggc ttc ccc ttc ggc ccc gag cac aac atc atc aag aac     1200
Asn Ile Thr Gly Phe Pro Phe Gly Pro Glu His Asn Ile Ile Lys Asn
385                 390                 395                 400 tga                                                                 1203
```

<210> SEQ ID NO 6
<211> LENGTH: 400
<212> TYPE: PRT
<213> ORGANISM: Ochrobactrum anthropi

<400> SEQUENCE: 6

```
Met Leu His Val Met Lys Trp His Asn Gly Glu Lys Asp Tyr Ser Pro
1               5                   10                  15

Phe Ser Glu Ala Glu Met Thr Arg Arg Gln Asn Asp Val Arg Gly Trp
            20                  25                  30

Met Ala Lys Asn Asp Val Asp Ala Ala Leu Phe Thr Ser Tyr His Cys
        35                  40                  45

Ile Asn Tyr Tyr Ser Gly Trp Leu Tyr Cys Tyr Phe Gly Arg Lys Tyr
    50                  55                  60

Gly Met Val Ile Asp His Asn Lys Ala Thr Thr Ile Ser Ala Gly Ile
65                  70                  75                  80

Asp Gly Gly Gln Pro Trp Arg Arg Ser Phe Gly Asp Asn Ile Thr Tyr
                85                  90                  95

Thr Asp Trp Arg Arg Asp Asn Phe Tyr Gln Ala Val Arg Gln Leu Thr
            100                 105                 110

Lys Gly Ala Lys Arg Val Gly Ile Glu Phe Asp His Val Ser Leu Asp
```

```
            115                 120                 125
Phe Arg Arg Gln Leu Glu Glu Ala Leu Pro Gly Val Glu Phe Val Asp
    130                 135                 140

Val Gly Gln Pro Ser Met Trp Met Arg Thr Ile Lys Ser Ala Glu Glu
145                 150                 155                 160

Gln Lys Leu Ile Arg Glu Gly Ala Arg Val Cys Asp Val Gly Gly Ala
                165                 170                 175

Ala Cys Ala Ala Ala Val Lys Ala Gly Val Pro Glu His Glu Val Ala
            180                 185                 190

Ile Ala Thr Thr Asn Ala Met Val Arg Glu Ile Ala Lys Ser Phe Pro
        195                 200                 205

Phe Val Glu Leu Met Asp Thr Trp Thr Trp Phe Gln Ser Gly Ile Asn
    210                 215                 220

Thr Asp Gly Ala His Asn Pro Val Thr Asn Arg Ile Val Gln Ser Gly
225                 230                 235                 240

Asp Ile Leu Ser Leu Asn Thr Phe Pro Met Ile Phe Gly Tyr Tyr Thr
                245                 250                 255

Ala Leu Glu Arg Thr Leu Phe Cys Asp His Val Asp Asp Ala Ser Leu
            260                 265                 270

Asp Ile Trp Glu Lys Asn Val Ala Val His Arg Arg Gly Leu Glu Leu
        275                 280                 285

Ile Lys Pro Gly Ala Arg Cys Lys Asp Ile Ala Leu Glu Leu Asn Asp
    290                 295                 300

Met Tyr Arg Glu Trp Asp Leu Leu Lys Tyr Arg Ser Phe Gly Tyr Gly
305                 310                 315                 320

His Ser Phe Gly Val Leu Cys His Tyr Tyr Gly Arg Glu Ala Gly Val
                325                 330                 335

Glu Leu Arg Glu Asp Ile Asp Thr Val Leu Glu Pro Gly Met Val Val
            340                 345                 350

Ser Met Glu Pro Met Val Met Leu Pro Glu Gly Ala Pro Gly Ala Gly
        355                 360                 365

Gly Tyr Arg Glu His Asp Ile Leu Ile Val Lys Glu Asp Ser Ala Glu
    370                 375                 380

Asn Ile Thr Gly Phe Pro Phe Gly Pro Glu His Asn Ile Ile Lys Asn
385                 390                 395                 400
```

<210> SEQ ID NO 7
<211> LENGTH: 400
<212> TYPE: PRT
<213> ORGANISM: Ochrobactrum anthropi
<220> FEATURE:
<221> NAME/KEY: mat_peptide
<222> LOCATION: (1)..(400)
<223> OTHER INFORMATION: Mutant creatine amidinohydrolase _Ochrobactrum anthropi A0A076WGB5 with C171A+C295A substitutions

<400> SEQUENCE: 7

```
Met Leu His Val Met Lys Trp His Asn Gly Lys Asp Tyr Ser Pro
1               5                   10                  15

Phe Ser Glu Ala Glu Met Thr Arg Arg Gln Asn Asp Val Arg Gly Trp
                20                  25                  30

Met Ala Lys Asn Asp Val Asp Ala Leu Phe Thr Ser Tyr His Cys
            35                  40                  45

Ile Asn Tyr Tyr Ser Gly Trp Leu Tyr Cys Tyr Phe Gly Arg Lys Tyr
        50                  55                  60

Gly Met Val Ile Asp His Asn Lys Ala Thr Thr Ile Ser Ala Gly Ile
```

```
                65                  70                  75                  80
Asp Gly Gly Gln Pro Trp Arg Arg Ser Phe Gly Asp Asn Ile Thr Tyr
                            85                  90                  95

Thr Asp Trp Arg Arg Asp Asn Phe Tyr Gln Ala Val Arg Gln Leu Thr
                100                 105                 110

Lys Gly Ala Lys Arg Val Gly Ile Glu Phe Asp His Val Ser Leu Asp
                115                 120                 125

Phe Arg Arg Gln Leu Glu Glu Ala Leu Pro Gly Val Glu Phe Val Asp
130                 135                 140

Val Gly Gln Pro Ser Met Trp Met Arg Thr Ile Lys Ser Ala Glu Glu
145                 150                 155                 160

Gln Lys Leu Ile Arg Glu Gly Ala Arg Val Ala Asp Val Gly Gly Ala
                165                 170                 175

Ala Cys Ala Ala Ala Val Lys Ala Gly Val Pro Glu His Glu Val Ala
                180                 185                 190

Ile Ala Thr Thr Asn Ala Met Val Arg Glu Ile Ala Lys Ser Phe Pro
                195                 200                 205

Phe Val Glu Leu Met Asp Thr Trp Thr Trp Phe Gln Ser Gly Ile Asn
                210                 215                 220

Thr Asp Gly Ala His Asn Pro Val Thr Asn Arg Ile Val Gln Ser Gly
225                 230                 235                 240

Asp Ile Leu Ser Leu Asn Thr Phe Pro Met Ile Phe Gly Tyr Tyr Thr
                245                 250                 255

Ala Leu Glu Arg Thr Leu Phe Cys Asp His Val Asp Asp Ala Ser Leu
                260                 265                 270

Asp Ile Trp Glu Lys Asn Val Ala Val His Arg Arg Gly Leu Glu Leu
                275                 280                 285

Ile Lys Pro Gly Ala Arg Ala Lys Asp Ile Ala Leu Glu Leu Asn Asp
                290                 295                 300

Met Tyr Arg Glu Trp Asp Leu Leu Lys Tyr Arg Ser Phe Gly Tyr Gly
305                 310                 315                 320

His Ser Phe Gly Val Leu Cys His Tyr Tyr Gly Arg Glu Ala Gly Val
                325                 330                 335

Glu Leu Arg Glu Asp Ile Asp Thr Val Leu Glu Pro Gly Met Val Val
                340                 345                 350

Ser Met Glu Pro Met Val Met Leu Pro Glu Gly Ala Pro Gly Ala Gly
                355                 360                 365

Gly Tyr Arg Glu His Asp Ile Leu Ile Val Lys Glu Asp Ser Ala Glu
                370                 375                 380

Asn Ile Thr Gly Phe Pro Phe Gly Pro Glu His Asn Ile Ile Lys Asn
385                 390                 395                 400
```

<210> SEQ ID NO 8
<211> LENGTH: 400
<212> TYPE: PRT
<213> ORGANISM: Ochrobactrum anthropi
<220> FEATURE:
<221> NAME/KEY: mat_peptide
<222> LOCATION: (1)..(400)
<223> OTHER INFORMATION: Mutant creatine amidinohydrolase _Ochrobactrum
      anthropi A0A076WGB5 with C171A+C295A+C264L substitutions

<400> SEQUENCE: 8

```
Met Leu His Val Met Lys Trp His Asn Gly Glu Lys Asp Tyr Ser Pro
1               5                   10                  15

Phe Ser Glu Ala Glu Met Thr Arg Arg Gln Asn Asp Val Arg Gly Trp
```

```
                    20                  25                  30
Met Ala Lys Asn Asp Val Asp Ala Ala Leu Phe Thr Ser Tyr His Cys
                35                  40                  45

Ile Asn Tyr Tyr Ser Gly Trp Leu Tyr Cys Tyr Phe Gly Arg Lys Tyr
        50                  55                  60

Gly Met Val Ile Asp His Asn Lys Ala Thr Thr Ile Ser Ala Gly Ile
65                  70                  75                  80

Asp Gly Gly Gln Pro Trp Arg Arg Ser Phe Gly Asp Asn Ile Thr Tyr
                85                  90                  95

Thr Asp Trp Arg Arg Asp Asn Phe Tyr Gln Ala Val Arg Gln Leu Thr
                100                 105                 110

Lys Gly Ala Lys Arg Val Gly Ile Glu Phe Asp His Val Ser Leu Asp
                115                 120                 125

Phe Arg Arg Gln Leu Glu Glu Ala Leu Pro Gly Val Glu Phe Val Asp
                130                 135                 140

Val Gly Gln Pro Ser Met Trp Met Arg Thr Ile Lys Ser Ala Glu Glu
145                 150                 155                 160

Gln Lys Leu Ile Arg Glu Gly Ala Arg Val Ala Asp Val Gly Gly Ala
                165                 170                 175

Ala Cys Ala Ala Ala Val Lys Ala Gly Val Pro Glu His Glu Val Ala
                180                 185                 190

Ile Ala Thr Thr Asn Ala Met Val Arg Glu Ile Ala Lys Ser Phe Pro
                195                 200                 205

Phe Val Glu Leu Met Asp Thr Trp Thr Trp Phe Gln Ser Gly Ile Asn
                210                 215                 220

Thr Asp Gly Ala His Asn Pro Val Thr Asn Arg Ile Val Gln Ser Gly
225                 230                 235                 240

Asp Ile Leu Ser Leu Asn Thr Phe Pro Met Ile Phe Gly Tyr Tyr Thr
                245                 250                 255

Ala Leu Glu Arg Thr Leu Phe Leu Asp His Val Asp Asp Ala Ser Leu
                260                 265                 270

Asp Ile Trp Glu Lys Asn Val Ala Val His Arg Arg Gly Leu Glu Leu
                275                 280                 285

Ile Lys Pro Gly Ala Arg Ala Lys Asp Ile Ala Leu Glu Leu Asn Asp
                290                 295                 300

Met Tyr Arg Glu Trp Asp Leu Leu Lys Tyr Arg Ser Phe Gly Tyr Gly
305                 310                 315                 320

His Ser Phe Gly Val Leu Cys His Tyr Tyr Gly Arg Glu Ala Gly Val
                325                 330                 335

Glu Leu Arg Glu Asp Ile Asp Thr Val Leu Glu Pro Gly Met Val Val
                340                 345                 350

Ser Met Glu Pro Met Val Met Leu Pro Glu Gly Ala Pro Gly Ala Gly
                355                 360                 365

Gly Tyr Arg Glu His Asp Ile Leu Ile Val Lys Glu Asp Ser Ala Glu
                370                 375                 380

Asn Ile Thr Gly Phe Pro Phe Gly Pro Glu His Asn Ile Ile Lys Asn
385                 390                 395                 400

<210> SEQ ID NO 9
<211> LENGTH: 1215
<212> TYPE: DNA
<213> ORGANISM: Mesorhizobium sp
<220> FEATURE:
<221> NAME/KEY: CDS
<222> LOCATION: (1)..(1215)
```

<223> OTHER INFORMATION: ESY78205.1 Mesorhizobium sp. LNHC221B00 gene
encoding creatine amidinohydrolase [LNHC221B00]

<400> SEQUENCE: 9

| | | | | | | | | | | | | | | | | |
|---|---|---|---|---|---|---|---|---|---|---|---|---|---|---|---|---|
| atg | act | gac | gac | atg | ctg | cac | gtg | gtg | aaa | tgg | cac | aac | gga | gag | aag | 48 |
| Met | Thr | Asp | Asp | Met | Leu | His | Val | Val | Lys | Trp | His | Asn | Gly | Glu | Lys | |
| 1 | | | | 5 | | | | | 10 | | | | | 15 | | |

| gac | tat | tct | ccc | ttc | tcg | gaa | gct | gag | atg | aag | cgc | cgc | caa | aac | gac | 96 |
|---|---|---|---|---|---|---|---|---|---|---|---|---|---|---|---|---|
| Asp | Tyr | Ser | Pro | Phe | Ser | Glu | Ala | Glu | Met | Lys | Arg | Arg | Gln | Asn | Asp | |
| | | | 20 | | | | | 25 | | | | | 30 | | | |

| gta | cgt | cgc | tgg | atg | gcc | gac | aac | aac | gtc | gac | gcg | gcc | ctg | ttc | acc | 144 |
|---|---|---|---|---|---|---|---|---|---|---|---|---|---|---|---|---|
| Val | Arg | Arg | Trp | Met | Ala | Asp | Asn | Asn | Val | Asp | Ala | Ala | Leu | Phe | Thr | |
| | 35 | | | | | 40 | | | | | 45 | | | | | |

| tcc | tat | cat | tgc | atc | aac | tac | tat | tcc | ggt | tgg | ctc | tac | tgc | tac | ttc | 192 |
|---|---|---|---|---|---|---|---|---|---|---|---|---|---|---|---|---|
| Ser | Tyr | His | Cys | Ile | Asn | Tyr | Tyr | Ser | Gly | Trp | Leu | Tyr | Cys | Tyr | Phe | |
| 50 | | | | | 55 | | | | | 60 | | | | | | |

| ggc | cgc | aag | tac | ggc | atg | gtc | atc | gac | cag | gac | aac | gcc | acg | acc | atc | 240 |
|---|---|---|---|---|---|---|---|---|---|---|---|---|---|---|---|---|
| Gly | Arg | Lys | Tyr | Gly | Met | Val | Ile | Asp | Gln | Asp | Asn | Ala | Thr | Thr | Ile | |
| 65 | | | | | 70 | | | | | 75 | | | | | 80 | |

| tcg | gcc | ggc | att | gat | ggc | ggc | cag | ccc | tat | cgc | cgc | agc | ttc | ggc | gac | 288 |
|---|---|---|---|---|---|---|---|---|---|---|---|---|---|---|---|---|
| Ser | Ala | Gly | Ile | Asp | Gly | Gly | Gln | Pro | Tyr | Arg | Arg | Ser | Phe | Gly | Asp | |
| | | | | 85 | | | | | 90 | | | | | 95 | | |

| aac | att | acc | tac | acg | gac | tgg | cgc | cgc | gac | aac | tac | tat | cgc | gcc | gtg | 336 |
|---|---|---|---|---|---|---|---|---|---|---|---|---|---|---|---|---|
| Asn | Ile | Thr | Tyr | Thr | Asp | Trp | Arg | Arg | Asp | Asn | Tyr | Tyr | Arg | Ala | Val | |
| | | | 100 | | | | | 105 | | | | | 110 | | | |

| cgc | cag | ttg | acg | gcg | ggc | gcc | aag | cgc | gtc | ggc | atc | gag | ttc | gat | cat | 384 |
|---|---|---|---|---|---|---|---|---|---|---|---|---|---|---|---|---|
| Arg | Gln | Leu | Thr | Ala | Gly | Ala | Lys | Arg | Val | Gly | Ile | Glu | Phe | Asp | His | |
| | | 115 | | | | | 120 | | | | | 125 | | | | |

| gtc | aat | ctc | gat | ttc | cgc | cgg | caa | ctc | gaa | gag | gcg | ctg | ccg | ggc | gtc | 432 |
|---|---|---|---|---|---|---|---|---|---|---|---|---|---|---|---|---|
| Val | Asn | Leu | Asp | Phe | Arg | Arg | Gln | Leu | Glu | Glu | Ala | Leu | Pro | Gly | Val | |
| 130 | | | | | 135 | | | | | 140 | | | | | | |

| gaa | ttc | atc | gat | att | gcc | caa | ccc | tcg | atg | tgg | atg | cgc | tcg | atc | aaa | 480 |
|---|---|---|---|---|---|---|---|---|---|---|---|---|---|---|---|---|
| Glu | Phe | Ile | Asp | Ile | Ala | Gln | Pro | Ser | Met | Trp | Met | Arg | Ser | Ile | Lys | |
| 145 | | | | | 150 | | | | | 155 | | | | | 160 | |

| tcg | gtg | gag | gag | cac | acc | ttg | atc | cgc | gag | ggg | gcg | cgc | gtc | agc | gac | 528 |
|---|---|---|---|---|---|---|---|---|---|---|---|---|---|---|---|---|
| Ser | Val | Glu | Glu | His | Thr | Leu | Ile | Arg | Glu | Gly | Ala | Arg | Val | Ser | Asp | |
| | | | | 165 | | | | | 170 | | | | | 175 | | |

| gtc | ggc | ggc | gca | gcg | tgc | gtg | gcg | gcg | gta | aag | gcc | ggc | gtt | ccg | gag | 576 |
|---|---|---|---|---|---|---|---|---|---|---|---|---|---|---|---|---|
| Val | Gly | Gly | Ala | Ala | Cys | Val | Ala | Ala | Val | Lys | Ala | Gly | Val | Pro | Glu | |
| | | | 180 | | | | | 185 | | | | | 190 | | | |

| cac | gag | gtg | gcg | atc | gcc | acc | acc | gat | gca | atg | atc | cgc | gaa | atc | gcg | 624 |
|---|---|---|---|---|---|---|---|---|---|---|---|---|---|---|---|---|
| His | Glu | Val | Ala | Ile | Ala | Thr | Thr | Asp | Ala | Met | Ile | Arg | Glu | Ile | Ala | |
| | | 195 | | | | | 200 | | | | | 205 | | | | |

| aaa | tcg | cac | ccc | ttc | gtc | gaa | ctg | atg | gac | acc | tgg | acc | tgg | ttc | cag | 672 |
|---|---|---|---|---|---|---|---|---|---|---|---|---|---|---|---|---|
| Lys | Ser | His | Pro | Phe | Val | Glu | Leu | Met | Asp | Thr | Trp | Thr | Trp | Phe | Gln | |
| 210 | | | | | 215 | | | | | 220 | | | | | | |

| tcg | ggc | atc | aac | acc | gat | ggc | gcg | cac | aat | ccg | gtc | acg | aac | cgc | gtc | 720 |
|---|---|---|---|---|---|---|---|---|---|---|---|---|---|---|---|---|
| Ser | Gly | Ile | Asn | Thr | Asp | Gly | Ala | His | Asn | Pro | Val | Thr | Asn | Arg | Val | |
| 225 | | | | | 230 | | | | | 235 | | | | | 240 | |

| gtg | cgg | gct | gga | gac | atc | ctg | tcg | ctc | aac | acc | ttt | ccg | atg | atc | ttc | 768 |
|---|---|---|---|---|---|---|---|---|---|---|---|---|---|---|---|---|
| Val | Arg | Ala | Gly | Asp | Ile | Leu | Ser | Leu | Asn | Thr | Phe | Pro | Met | Ile | Phe | |
| | | | | 245 | | | | | 250 | | | | | 255 | | |

| ggc | tac | tac | acc | gca | ctc | gaa | cgg | acg | ctg | ttc | tgc | gac | cac | gcc | gac | 816 |
|---|---|---|---|---|---|---|---|---|---|---|---|---|---|---|---|---|
| Gly | Tyr | Tyr | Thr | Ala | Leu | Glu | Arg | Thr | Leu | Phe | Cys | Asp | His | Ala | Asp | |
| | | | 260 | | | | | 265 | | | | | 270 | | | |

| gat | gcc | agc | ctg | gac | gta | tgg | cag | aag | aat | gtc | gcc | gtg | cat | cgc | cgt | 864 |
|---|---|---|---|---|---|---|---|---|---|---|---|---|---|---|---|---|
| Asp | Ala | Ser | Leu | Asp | Val | Trp | Gln | Lys | Asn | Val | Ala | Val | His | Arg | Arg | |
| | | 275 | | | | | 280 | | | | | 285 | | | | |

| ggt | ctc | gag | ctg | atc | aag | cct | ggc | gtc | cgt | tgc | aag | gac | atc | gca | atc | 912 |
|---|---|---|---|---|---|---|---|---|---|---|---|---|---|---|---|---|
| Gly | Leu | Glu | Leu | Ile | Lys | Pro | Gly | Val | Arg | Cys | Lys | Asp | Ile | Ala | Ile | |

```
                  290                 295                 300
gag ctc aac gag atg tac cgc gag tgg gat ctc ctg aaa tac cgg tcc       960
Glu Leu Asn Glu Met Tyr Arg Glu Trp Asp Leu Leu Lys Tyr Arg Ser
305                 310                 315                 320 ttc ggg tat ggc cac tcc ttc ggt gtg ctc tgc cac tat tat ggc cgc      1008
Phe Gly Tyr Gly His Ser Phe Gly Val Leu Cys His Tyr Tyr Gly Arg
                325                 330                 335 gag gct ggc gtc gag ttg cgt gag gac atc gaa aca gtg ctg gag ccc      1056
Glu Ala Gly Val Glu Leu Arg Glu Asp Ile Glu Thr Val Leu Glu Pro
                340                 345                 350 ggc atg gtg gtg tcg atg gag ccg atg gtc atg ttg ccg gaa ggc acg      1104
Gly Met Val Val Ser Met Glu Pro Met Val Met Leu Pro Glu Gly Thr
                355                 360                 365 cca ggc gcc ggc ggc tac cgc gag cat gac atc ctg atc gtc aag gac      1152
Pro Gly Ala Gly Gly Tyr Arg Glu His Asp Ile Leu Ile Val Lys Asp
370                 375                 380 gac ggc gcc gaa aac atc acc ggt ttc ccc ttc ggg ccg gaa cac aac      1200
Asp Gly Ala Glu Asn Ile Thr Gly Phe Pro Phe Gly Pro Glu His Asn
385                 390                 395                 400 atc atc agg aat tga                                                  1215
Ile Ile Arg Asn <210> SEQ ID NO 10
<211> LENGTH: 404
<212> TYPE: PRT
<213> ORGANISM: Mesorhizobium sp

<400> SEQUENCE: 10

Met Thr Asp Asp Met Leu His Val Val Lys Trp His Asn Gly Glu Lys
1               5                   10                  15

Asp Tyr Ser Pro Phe Ser Glu Ala Glu Met Lys Arg Arg Gln Asn Asp
                20                  25                  30

Val Arg Arg Trp Met Ala Asp Asn Val Asp Ala Ala Leu Phe Thr
            35                  40                  45

Ser Tyr His Cys Ile Asn Tyr Tyr Ser Gly Trp Leu Tyr Cys Tyr Phe
50                  55                  60

Gly Arg Lys Tyr Gly Met Val Ile Asp Gln Asp Asn Ala Thr Thr Ile
65                  70                  75                  80

Ser Ala Gly Ile Asp Gly Gly Gln Pro Tyr Arg Arg Ser Phe Gly Asp
                85                  90                  95

Asn Ile Thr Tyr Thr Asp Trp Arg Arg Asp Asn Tyr Tyr Arg Ala Val
                100                 105                 110

Arg Gln Leu Thr Ala Gly Ala Lys Arg Val Gly Ile Glu Phe Asp His
            115                 120                 125

Val Asn Leu Asp Phe Arg Arg Gln Leu Glu Glu Ala Leu Pro Gly Val
130                 135                 140

Glu Phe Ile Asp Ile Ala Gln Pro Ser Met Trp Met Arg Ser Ile Lys
145                 150                 155                 160

Ser Val Glu Glu His Thr Leu Ile Arg Glu Gly Ala Arg Val Ser Asp
                165                 170                 175

Val Gly Gly Ala Ala Cys Val Ala Ala Val Lys Ala Gly Val Pro Glu
                180                 185                 190

His Glu Val Ala Ile Ala Thr Thr Asp Ala Met Ile Arg Glu Ile Ala
            195                 200                 205

Lys Ser His Pro Phe Val Glu Leu Met Asp Thr Trp Thr Trp Phe Gln
210                 215                 220
```

```
Ser Gly Ile Asn Thr Asp Gly Ala His Asn Pro Val Thr Asn Arg Val
225                 230                 235                 240

Val Arg Ala Gly Asp Ile Leu Ser Leu Asn Thr Phe Pro Met Ile Phe
            245                 250                 255

Gly Tyr Tyr Thr Ala Leu Glu Arg Thr Leu Phe Cys Asp His Ala Asp
            260                 265                 270

Asp Ala Ser Leu Asp Val Trp Gln Lys Asn Val Ala Val His Arg Arg
        275                 280                 285

Gly Leu Glu Leu Ile Lys Pro Gly Val Arg Cys Lys Asp Ile Ala Ile
        290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Glu Thr Val Leu Glu Pro
                340                 345                 350

Gly Met Val Val Ser Met Glu Pro Met Val Met Leu Pro Glu Gly Thr
            355                 360                 365

Pro Gly Ala Gly Gly Tyr Arg Glu His Asp Ile Leu Ile Val Lys Asp
    370                 375                 380

Asp Gly Ala Glu Asn Ile Thr Gly Phe Pro Phe Gly Pro Glu His Asn
385                 390                 395                 400

Ile Ile Arg Asn

<210> SEQ ID NO 11
<211> LENGTH: 404
<212> TYPE: PRT
<213> ORGANISM: Mesorhizobium sp
<220> FEATURE:
<221> NAME/KEY: mat_peptide
<222> LOCATION: (1)..(404)
<223> OTHER INFORMATION: Mutant creatine amidinohydrolase _Mesorhizobium
      sp. X6DLM3 with S175A+C299A substitutions

<400> SEQUENCE: 11

Met Thr Asp Asp Met Leu His Val Val Lys Trp His Asn Gly Glu Lys
1               5                   10                  15

Asp Tyr Ser Pro Phe Ser Glu Ala Glu Met Lys Arg Arg Gln Asn Asp
            20                  25                  30

Val Arg Arg Trp Met Ala Asp Asn Val Asp Ala Ala Leu Phe Thr
        35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Asp Gln Asp Asn Ala Thr Thr Ile
65                  70                  75                  80

Ser Ala Gly Ile Asp Gly Gly Gln Pro Tyr Arg Arg Ser Phe Gly Asp
                85                  90                  95

Asn Ile Thr Tyr Thr Asp Trp Arg Asp Asn Tyr Tyr Arg Ala Val
            100                 105                 110

Arg Gln Leu Thr Ala Gly Ala Lys Arg Val Gly Ile Glu Phe Asp His
        115                 120                 125

Val Asn Leu Asp Phe Arg Arg Gln Leu Glu Glu Leu Pro Gly Val
        130                 135                 140

Glu Phe Ile Asp Ile Ala Gln Pro Ser Met Trp Met Arg Ser Ile Lys
145                 150                 155                 160

Ser Val Glu Glu His Thr Leu Ile Arg Glu Gly Ala Arg Val Ala Asp
```

```
                    165                 170                 175
Val Gly Gly Ala Ala Cys Val Ala Ala Val Lys Ala Gly Val Pro Glu
                180                 185                 190

His Glu Val Ala Ile Ala Thr Thr Asp Ala Met Ile Arg Glu Ile Ala
            195                 200                 205

Lys Ser His Pro Phe Val Glu Leu Met Asp Thr Trp Thr Trp Phe Gln
        210                 215                 220

Ser Gly Ile Asn Thr Asp Gly Ala His Asn Pro Val Thr Asn Arg Val
225                 230                 235                 240

Val Arg Ala Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Ala Asp
                260                 265                 270

Asp Ala Ser Leu Asp Val Trp Gln Lys Asn Val Ala Val His Arg Arg
            275                 280                 285

Gly Leu Glu Leu Ile Lys Pro Gly Val Arg Ala Lys Asp Ile Ala Ile
        290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Glu Thr Val Leu Glu Pro
            340                 345                 350

Gly Met Val Val Ser Met Glu Pro Met Val Met Leu Pro Glu Gly Thr
        355                 360                 365

Pro Gly Ala Gly Gly Tyr Arg Glu His Asp Ile Leu Ile Val Lys Asp
    370                 375                 380

Asp Gly Ala Glu Asn Ile Thr Gly Phe Pro Phe Gly Pro Glu His Asn
385                 390                 395                 400

Ile Ile Arg Asn

<210> SEQ ID NO 12
<211> LENGTH: 404
<212> TYPE: PRT
<213> ORGANISM: Mesorhizobium sp
<220> FEATURE:
<221> NAME/KEY: mat_peptide
<222> LOCATION: (1)..(404)
<223> OTHER INFORMATION: Mutant creatine amidinohydrolase _Mesorhizobium
      sp. X6DLM3 with S175A+C299A+C268L substitutions

<400> SEQUENCE: 12

Met Thr Asp Asp Met Leu His Val Val Lys Trp His Asn Gly Glu Lys
1               5                   10                  15

Asp Tyr Ser Pro Phe Ser Glu Ala Glu Met Lys Arg Arg Gln Asn Asp
                20                  25                  30

Val Arg Arg Trp Met Ala Asp Asn Asn Val Asp Ala Ala Leu Phe Thr
            35                  40                  45

Ser Tyr His Cys Ile Asn Tyr Tyr Ser Gly Trp Leu Tyr Cys Tyr Phe
        50                  55                  60

Gly Arg Lys Tyr Gly Met Val Ile Asp Gln Asp Asn Ala Thr Thr Ile
65                  70                  75                  80

Ser Ala Gly Ile Asp Gly Gly Gln Pro Tyr Arg Arg Ser Phe Gly Asp
                85                  90                  95

Asn Ile Thr Tyr Thr Asp Trp Arg Arg Asp Asn Tyr Tyr Arg Ala Val
            100                 105                 110
```

```
Arg Gln Leu Thr Ala Gly Ala Lys Arg Val Gly Ile Glu Phe Asp His
        115                 120                 125
Val Asn Leu Asp Phe Arg Arg Gln Leu Glu Glu Ala Leu Pro Gly Val
    130                 135                 140
Glu Phe Ile Asp Ile Ala Gln Pro Ser Met Trp Met Arg Ser Ile Lys
145                 150                 155                 160
Ser Val Glu Glu His Thr Leu Ile Arg Glu Gly Ala Arg Val Ala Asp
                165                 170                 175
Val Gly Gly Ala Ala Cys Val Ala Ala Val Lys Ala Gly Val Pro Glu
            180                 185                 190
His Glu Val Ala Ile Ala Thr Thr Asp Ala Met Ile Arg Glu Ile Ala
        195                 200                 205
Lys Ser His Pro Phe Val Glu Leu Met Asp Thr Trp Thr Trp Phe Gln
    210                 215                 220
Ser Gly Ile Asn Thr Asp Gly Ala His Asn Pro Val Thr Asn Arg Val
225                 230                 235                 240
Val Arg Ala Gly Asp Ile Leu Ser Leu Asn Thr Phe Pro Met Ile Phe
                245                 250                 255
Gly Tyr Tyr Thr Ala Leu Glu Arg Thr Leu Phe Leu Asp His Ala Asp
            260                 265                 270
Asp Ala Ser Leu Asp Val Trp Gln Lys Asn Val Ala Val His Arg Arg
        275                 280                 285
Gly Leu Glu Leu Ile Lys Pro Gly Val Arg Ala Lys Asp Ile Ala Ile
    290                 295                 300
Glu Leu Asn Glu Met Tyr Arg Glu Trp Asp Leu Leu Lys Tyr Arg Ser
305                 310                 315                 320
Phe Gly Tyr Gly His Ser Phe Gly Val Leu Cys His Tyr Tyr Gly Arg
                325                 330                 335
Glu Ala Gly Val Glu Leu Arg Glu Asp Ile Glu Thr Val Leu Glu Pro
            340                 345                 350
Gly Met Val Val Ser Met Glu Pro Met Val Met Leu Pro Glu Gly Thr
        355                 360                 365
Pro Gly Ala Gly Gly Tyr Arg Glu His Asp Ile Leu Ile Val Lys Asp
    370                 375                 380
Asp Gly Ala Glu Asn Ile Thr Gly Phe Pro Phe Gly Pro Glu His Asn
385                 390                 395                 400
Ile Ile Arg Asn

<210> SEQ ID NO 13
<211> LENGTH: 1218
<212> TYPE: DNA
<213> ORGANISM: Roseovarius sp
<220> FEATURE:
<221> NAME/KEY: CDS
<222> LOCATION: (1)..(1218)
<223> OTHER INFORMATION: EDM33382.1 Roseovarius sp. TM1035 gene
      encoding creatine amidinohydrolase [A6DVF8]

<400> SEQUENCE: 13 atg ctt gac gac atg ttg cac gtc acg gaa tgg cac aac ggc gaa aag    48
Met Leu Asp Asp Met Leu His Val Thr Glu Trp His Asn Gly Glu Lys
1               5                   10                  15 gag ttt tcg ccc ttt tcc gac aat gaa atg gcc cgc gcc cag aac gaa    96
Glu Phe Ser Pro Phe Ser Asp Asn Glu Met Ala Arg Arg Gln Asn Glu
            20                  25                  30 ttg cgc gtc tgg atg gcc gat aac aac gtc gat gcg gcg ctc ttc acg   144
```

```
                Leu Arg Val Trp Met Ala Asp Asn Asn Val Asp Ala Ala Leu Phe Thr
                        35                  40                  45 tcc tat cac tgc att aac tat tac tca ggc tgg ctc tac tgc tat ttc        192
Ser Tyr His Cys Ile Asn Tyr Tyr Ser Gly Trp Leu Tyr Cys Tyr Phe
 50                  55                  60 ggt cgc aaa tat ggc atg gtc att gac caa aag aac gcc acg acc att        240
Gly Arg Lys Tyr Gly Met Val Ile Asp Gln Lys Asn Ala Thr Thr Ile
 65                  70                  75                  80 tcc gca ggc atc gac ggc ggc cag ccc tgg cgg cga aca ttc ggc agc        288
Ser Ala Gly Ile Asp Gly Gly Gln Pro Trp Arg Arg Thr Phe Gly Ser
                     85                  90                  95 aat gtc acc tat acc gac tgg cgg cgc gac aat ttc tac cgc gcg gtg        336
Asn Val Thr Tyr Thr Asp Trp Arg Arg Asp Asn Phe Tyr Arg Ala Val
                    100                 105                 110 cag ggc ctg acc aag ggt gcc cgc cgc gtc ggc atc gag ttt gac cat        384
Gln Gly Leu Thr Lys Gly Ala Arg Arg Val Gly Ile Glu Phe Asp His
                115                 120                 125 gtt tcg ctc gat tat cgc cag ctt ttg cag gat gcc ctg ccc ggc gtc        432
Val Ser Leu Asp Tyr Arg Gln Leu Leu Gln Asp Ala Leu Pro Gly Val
130                 135                 140 gaa ttg gtg gac gtg agc caa ccc tcg atg tgg atg cgc acc atc aaa        480
Glu Leu Val Asp Val Ser Gln Pro Ser Met Trp Met Arg Thr Ile Lys
145                 150                 155                 160 tcc gcc gag gaa atc aag ctc atc acc gaa ggc gcg cgc atc tgt gac        528
Ser Ala Glu Glu Ile Lys Leu Ile Thr Glu Gly Ala Arg Ile Cys Asp
                    165                 170                 175 gtg ggg ggc tat gcc gtg gcg ggc gct gtc aag gca ggc gtg ccc gaa        576
Val Gly Gly Tyr Ala Val Ala Gly Ala Val Lys Ala Gly Val Pro Glu
                180                 185                 190 cac gaa gtg gcg att gcg ggc aca aat gcg atg atc cgc gag att gcc        624
His Glu Val Ala Ile Ala Gly Thr Asn Ala Met Ile Arg Glu Ile Ala
            195                 200                 205 aaa tcc ttc ccc ttt gtc gaa ctg atg gac acc tgg aca tgg ttc cag        672
Lys Ser Phe Pro Phe Val Glu Leu Met Asp Thr Trp Thr Trp Phe Gln
210                 215                 220 tcg ggc atc aac acc gat ggc gcg cat aac ccc gtg acc aac cgc gtg        720
Ser Gly Ile Asn Thr Asp Gly Ala His Asn Pro Val Thr Asn Arg Val
225                 230                 235                 240 gtg caa tcg ggc gat atc ctc agc ctc aac acc ttc ccg atg atc ttt        768
Val Gln Ser Gly Asp Ile Leu Ser Leu Asn Thr Phe Pro Met Ile Phe
                245                 250                 255 ggc tat tac acc gcg ctc gaa cgc acg ctt ttt tgc gat cat gtc gat        816
Gly Tyr Tyr Thr Ala Leu Glu Arg Thr Leu Phe Cys Asp His Val Asp
                260                 265                 270 gac gcc agc ctc gac atc tgg gag aaa aac gtc gcc gtg cat cgt cgc        864
Asp Ala Ser Leu Asp Ile Trp Glu Lys Asn Val Ala Val His Arg Arg
            275                 280                 285 ggg ctg gag ttg atg aaa ccc ggc gcg cgc tgc atg gat atc gcg att        912
Gly Leu Glu Leu Met Lys Pro Gly Ala Arg Cys Met Asp Ile Ala Ile
290                 295                 300 gag ctg aac gag atg tat cgc gaa tgg gac ctg ctg aaa tac cgc tct        960
Glu Leu Asn Glu Met Tyr Arg Glu Trp Asp Leu Leu Lys Tyr Arg Ser
305                 310                 315                 320 ttc gga tat ggc cac agc ttt ggc gtg ctc agc cac tat tat ggc cgt       1008
Phe Gly Tyr Gly His Ser Phe Gly Val Leu Ser His Tyr Tyr Gly Arg
                325                 330                 335 gag gcg ggc gtg gaa ctg cgc gag gat atc gac acc gtg ctg aaa ccc       1056
Glu Ala Gly Val Glu Leu Arg Glu Asp Ile Asp Thr Val Leu Lys Pro
                340                 345                 350
```

```
ggc atg gtc gtg tcg atg gaa ccc atg gtg atg atc ccc gaa ggc cag      1104
Gly Met Val Val Ser Met Glu Pro Met Val Met Ile Pro Glu Gly Gln
        355                 360                 365 ccc ggc gcc ggt ggc tac cgc gag cat gac att ctg gtc atc gga gaa      1152
Pro Gly Ala Gly Gly Tyr Arg Glu His Asp Ile Leu Val Ile Gly Glu
370                 375                 380 gac ggg gcc gag aat atc acc ggc ttc ccc ttc gga cct gaa cat aac      1200
Asp Gly Ala Glu Asn Ile Thr Gly Phe Pro Phe Gly Pro Glu His Asn
385                 390                 395                 400 atc gtc ggc aaa ggc taa                                              1218
Ile Val Gly Lys Gly
                405

<210> SEQ ID NO 14
<211> LENGTH: 405
<212> TYPE: PRT
<213> ORGANISM: Roseovarius sp

<400> SEQUENCE: 14

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Val Trp Met Ala Asp Asn Val Asp Ala Ala Leu Phe Thr
        35                  40                  45

Ser Tyr His Cys Ile Asn Tyr Ser Gly Trp Leu Tyr Cys Tyr Phe
    50                  55                  60

Gly Arg Lys Tyr Gly Met Val Ile Asp Gln Lys Asn Ala Thr Thr Ile
65                  70                  75                  80

Ser Ala Gly Ile Asp Gly Gly Gln Pro Trp Arg Arg Thr Phe Gly Ser
                85                  90                  95

Asn Val Thr Tyr Thr Asp Trp Arg Arg Asp Asn Phe Tyr Arg Ala Val
            100                 105                 110

Gln Gly Leu Thr Lys Gly Ala Arg Arg Val Gly Ile Glu Phe Asp His
        115                 120                 125

Val Ser Leu Asp Tyr Arg Gln Leu Leu Gln Asp Ala Leu Pro Gly Val
130                 135                 140

Glu Leu Val Asp Val Ser Gln Pro Ser Met Trp Met Arg Thr Ile Lys
145                 150                 155                 160

Ser Ala Glu Glu Ile Lys Leu Ile Thr Glu Gly Ala Arg Ile Cys Asp
                165                 170                 175

Val Gly Gly Tyr Ala Val Ala Gly Ala Val Lys Ala Gly Val Pro Glu
            180                 185                 190

His Glu Val Ala Ile Ala Gly Thr Asn Ala Met Ile Arg Glu Ile Ala
        195                 200                 205

Lys Ser Phe Pro Phe Val Glu Leu Met Asp Thr Trp Thr Trp Phe Gln
210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
        275                 280                 285

Gly Leu Glu Leu Met Lys Pro Gly Ala Arg Cys Met Asp Ile Ala Ile
```

```
            290                 295                 300
Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Gln
        355                 360                 365

Pro Gly Ala Gly Gly Tyr Arg Glu His Asp Ile Leu Val Ile Gly Glu
    370                 375                 380

Asp Gly Ala Glu Asn Ile Thr Gly Phe Pro Phe Gly Pro Glu His Asn
385                 390                 395                 400

Ile Val Gly Lys Gly
            405

<210> SEQ ID NO 15
<211> LENGTH: 405
<212> TYPE: PRT
<213> ORGANISM: Roseovarius sp.
<220> FEATURE:
<221> NAME/KEY: mat_peptide
<222> LOCATION: (1)..(405)
<223> OTHER INFORMATION: Mutant creatine amidinohydrolase _Roseovarius
      sp. A6DVF8 with C175A+C299A substitutions

<400> SEQUENCE: 15

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Val Trp Met Ala Asp Asn Val Asp Ala Ala Leu Phe Thr
        35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Asp Gln Lys Asn Ala Thr Thr Ile
65                  70                  75                  80

Ser Ala Gly Ile Asp Gly Gly Gln Pro Trp Arg Arg Thr Phe Gly Ser
                85                  90                  95

Asn Val Thr Tyr Thr Asp Trp Arg Arg Asp Asn Phe Tyr Arg Ala Val
            100                 105                 110

Gln Gly Leu Thr Lys Gly Ala Arg Arg Val Gly Ile Glu Phe Asp His
        115                 120                 125

Val Ser Leu Asp Tyr Arg Gln Leu Leu Gln Asp Ala Leu Pro Gly Val
    130                 135                 140

Glu Leu Val Asp Val Ser Gln Pro Ser Met Trp Met Arg Thr Ile Lys
145                 150                 155                 160

Ser Ala Glu Glu Ile Lys Leu Ile Thr Glu Gly Ala Arg Ile Ala Asp
                165                 170                 175

Val Gly Gly Tyr Ala Val Ala Gly Ala Val Lys Ala Gly Val Pro Glu
            180                 185                 190

His Glu Val Ala Ile Ala Gly Thr Asn Ala Met Ile Arg Glu Ile Ala
        195                 200                 205

Lys Ser Phe Pro Phe Val Glu Leu Met Asp Thr Trp Thr Trp Phe Gln
    210                 215                 220

Ser Gly Ile Asn Thr Asp Gly Ala His Asn Pro Val Thr Asn Arg Val
```

```
            225                 230                 235                 240
Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
            275                 280                 285

Gly Leu Glu Leu Met Lys Pro Gly Ala Arg Ala Met Asp Ile Ala Ile
            290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Gln
            355                 360                 365

Pro Gly Ala Gly Gly Tyr Arg Glu His Asp Ile Leu Val Ile Gly Glu
            370                 375                 380

Asp Gly Ala Glu Asn Ile Thr Gly Phe Pro Phe Gly Pro Glu His Asn
385                 390                 395                 400

Ile Val Gly Lys Gly
                405

<210> SEQ ID NO 16
<211> LENGTH: 405
<212> TYPE: PRT
<213> ORGANISM: Roseovarius sp.
<220> FEATURE:
<221> NAME/KEY: mat_peptide
<222> LOCATION: (1)..(405)
<223> OTHER INFORMATION: Mutant creatine amidinohydrolase _Roseovarius
      sp. A6DVF8 with C175A+C299A+C268L substitutions

<400> SEQUENCE: 16

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Val Trp Met Ala Asp Asn Val Asp Ala Ala Leu Phe Thr
            35                  40                  45

Ser Tyr His Cys Ile Asn Tyr Tyr Ser Gly Trp Leu Tyr Cys Tyr Phe
        50                  55                  60

Gly Arg Lys Tyr Gly Met Val Ile Asp Gln Lys Asn Ala Thr Thr Ile
65                  70                  75                  80

Ser Ala Gly Ile Asp Gly Gly Gln Pro Trp Arg Arg Thr Phe Gly Ser
                85                  90                  95

Asn Val Thr Tyr Thr Asp Trp Arg Arg Asp Asn Phe Tyr Arg Ala Val
            100                 105                 110

Gln Gly Leu Thr Lys Gly Ala Arg Arg Val Gly Ile Glu Phe Asp His
            115                 120                 125

Val Ser Leu Asp Tyr Arg Gln Leu Leu Gln Asp Ala Leu Pro Gly Val
            130                 135                 140

Glu Leu Val Asp Val Ser Gln Pro Ser Met Trp Met Arg Thr Ile Lys
145                 150                 155                 160

Ser Ala Glu Glu Ile Lys Leu Ile Thr Glu Gly Ala Arg Ile Ala Asp
```

-continued

```
                  165                 170                 175
Val Gly Gly Tyr Ala Val Ala Gly Ala Val Lys Ala Gly Val Pro Glu
            180                 185                 190

His Glu Val Ala Ile Ala Gly Thr Asn Ala Met Ile Arg Glu Ile Ala
            195                 200                 205

Lys Ser Phe Pro Phe Val Glu Leu Met Asp Thr Trp Thr Trp Phe Gln
            210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Leu Asp His Val Asp
            260                 265                 270

Asp Ala Ser Leu Asp Ile Trp Glu Lys Asn Val Ala Val His Arg Arg
            275                 280                 285

Gly Leu Glu Leu Met Lys Pro Gly Ala Arg Ala Met Asp Ile Ala Ile
            290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Gln
            355                 360                 365

Pro Gly Ala Gly Gly Tyr Arg Glu His Asp Ile Leu Val Ile Gly Glu
            370                 375                 380

Asp Gly Ala Glu Asn Ile Thr Gly Phe Pro Phe Gly Pro Glu His Asn
385                 390                 395                 400

Ile Val Gly Lys Gly
                405
```

<210> SEQ ID NO 17
<211> LENGTH: 1218
<212> TYPE: DNA
<213> ORGANISM: Roseovarius sp.
<220> FEATURE:
<221> NAME/KEY: CDS
<222> LOCATION: (1)..(1218)
<223> OTHER INFORMATION: EAQ25420.1 Roseovarius sp. 217 gene encoding creatine amidinohydrolase [A3W1E4]

<400> SEQUENCE: 17

```
atg ctt gac gac atg ctg cac gtg acc gaa tgg cac aac gga gaa aag    48
Met Leu Asp Asp Met Leu His Val Thr Glu Trp His Asn Gly Glu Lys
1               5                   10                  15 gaa ttt tcg ccc ttt tcc gac aat gaa atg gcc cgc cgc cag aac gaa    96
Glu Phe Ser Pro Phe Ser Asp Asn Glu Met Ala Arg Arg Gln Asn Glu
            20                  25                  30 ttg cgc gtc tgg atg gcc gac aac aat gtc gat gcg gcg ctc ttc acg   144
Leu Arg Val Trp Met Ala Asp Asn Asn Val Asp Ala Ala Leu Phe Thr
        35                  40                  45 tcc tat cac tgc att aac tat tac tcg ggc tgg ctc tac tgc tat ttc   192
Ser Tyr His Cys Ile Asn Tyr Tyr Ser Gly Trp Leu Tyr Cys Tyr Phe
    50                  55                  60 ggt cgc aaa tat ggc atg gtc att gac caa aag aac gcc acg acg att   240
Gly Arg Lys Tyr Gly Met Val Ile Asp Gln Lys Asn Ala Thr Thr Ile
65                  70                  75                  80
```

-continued

| | | |
|---|---|---|
| tcc gca ggc atc gac ggc ggt cag ccg tgg cgc cgg acc ttt ggc agc<br>Ser Ala Gly Ile Asp Gly Gly Gln Pro Trp Arg Arg Thr Phe Gly Ser<br>    85              90              95 | 288 |
| aac gtc acc tat acc gac tgg cgg cgc gac aat ttc tat cgc gcg gtg<br>Asn Val Thr Tyr Thr Asp Trp Arg Arg Asp Asn Phe Tyr Arg Ala Val<br>        100             105             110 | 336 |
| cag ggc ctg acc aag ggc gcc cgc cgt gtg ggc atc gag ttt gac cat<br>Gln Gly Leu Thr Lys Gly Ala Arg Arg Val Gly Ile Glu Phe Asp His<br>    115             120             125 | 384 |
| gtc tcg ctc gac tac cgc caa ctc ttg cag gat gcg cta ccg ggc gtc<br>Val Ser Leu Asp Tyr Arg Gln Leu Leu Gln Asp Ala Leu Pro Gly Val<br>130             135             140 | 432 |
| gaa ctg gtg gac gtg agc cag ccc tcg atg tgg atg cgc acc atc aaa<br>Glu Leu Val Asp Val Ser Gln Pro Ser Met Trp Met Arg Thr Ile Lys<br>145             150             155             160 | 480 |
| tcc gcc gag gaa atc aag ctc atc acc gaa ggc gcg cgc atc tgc gac<br>Ser Ala Glu Glu Ile Lys Leu Ile Thr Glu Gly Ala Arg Ile Cys Asp<br>        165             170             175 | 528 |
| gtc ggc ggc tat gcc gtg gcc ggt gcc gtc aag gca ggc gtg ccc gag<br>Val Gly Gly Tyr Ala Val Ala Gly Ala Val Lys Ala Gly Val Pro Glu<br>    180             185             190 | 576 |
| cat gag gtg gcc atc gcg ggc acc aac gcg atg atc cgc gag atc gcc<br>His Glu Val Ala Ile Ala Gly Thr Asn Ala Met Ile Arg Glu Ile Ala<br>    195             200             205 | 624 |
| aaa tcc ttc ccc ttt gtc gaa ctg atg gat acc tgg aca tgg ttc cag<br>Lys Ser Phe Pro Phe Val Glu Leu Met Asp Thr Trp Thr Trp Phe Gln<br>210             215             220 | 672 |
| tcg ggc atc aac acc gac ggc gcg cat aac ccc gtg acc aac cgc gtg<br>Ser Gly Ile Asn Thr Asp Gly Ala His Asn Pro Val Thr Asn Arg Val<br>225             230             235             240 | 720 |
| gtg caa tcg ggc gac atc ctc agc ctc aac acc ttt ccg atg atc ttt<br>Val Gln Ser Gly Asp Ile Leu Ser Leu Asn Thr Phe Pro Met Ile Phe<br>        245             250             255 | 768 |
| ggc tat tac acc gcg ctc gaa cgc acg ctt ttt tgc gat cac gtc gat<br>Gly Tyr Tyr Thr Ala Leu Glu Arg Thr Leu Phe Cys Asp His Val Asp<br>    260             265             270 | 816 |
| gac gcc agc ctc gac atc tgg gag aaa aac gtc gcc gtg cat cgc cgc<br>Asp Ala Ser Leu Asp Ile Trp Glu Lys Asn Val Ala Val His Arg Arg<br>    275             280             285 | 864 |
| ggg ctg gaa ctg atg aag ccc ggc gcg cgc tgc atg gat atc gcg atc<br>Gly Leu Glu Leu Met Lys Pro Gly Ala Arg Cys Met Asp Ile Ala Ile<br>290             295             300 | 912 |
| gaa ctc aat gag atg tat cgc gac tgg gat ctg ctg aaa tac cgc tcc<br>Glu Leu Asn Glu Met Tyr Arg Asp Trp Asp Leu Leu Lys Tyr Arg Ser<br>305             310             315             320 | 960 |
| ttt ggc tac ggc cac agc ttt ggc gtg ctc agc cac tac tat ggc cgc<br>Phe Gly Tyr Gly His Ser Phe Gly Val Leu Ser His Tyr Tyr Gly Arg<br>        325             330             335 | 1008 |
| gag gca ggg gtg gaa ctg cgc gag gat atc gac acc gtg ctg aaa ccc<br>Glu Ala Gly Val Glu Leu Arg Glu Asp Ile Asp Thr Val Leu Lys Pro<br>    340             345             350 | 1056 |
| ggc atg gtc gtg tcg atg gaa ccg atg gtg atg atc ccc gag ggc cag<br>Gly Met Val Val Ser Met Glu Pro Met Val Met Ile Pro Glu Gly Gln<br>    355             360             365 | 1104 |
| ccc ggt gcc ggt ggc tac cgc gag cat gac att ctg gtc atc ggt gaa<br>Pro Gly Ala Gly Gly Tyr Arg Glu His Asp Ile Leu Val Ile Gly Glu<br>370             375             380 | 1152 |
| gat ggg gcc gag aat atc acc ggc ttt ccg ttc ggc ccc gaa cat aac<br>Asp Gly Ala Glu Asn Ile Thr Gly Phe Pro Phe Gly Pro Glu His Asn | 1200 |

```
                385                 390                 395                 400
atc gtc ggc aaa ggc taa                                                              1218
Ile Val Gly Lys Gly
            405

<210> SEQ ID NO 18
<211> LENGTH: 405
<212> TYPE: PRT
<213> ORGANISM: Roseovarius sp.

<400> SEQUENCE: 18

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Val Trp Met Ala Asp Asn Val Asp Ala Ala Leu Phe Thr
        35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Asp Gln Lys Asn Ala Thr Thr Ile
65                  70                  75                  80

Ser Ala Gly Ile Asp Gly Gly Gln Pro Trp Arg Arg Thr Phe Gly Ser
                85                  90                  95

Asn Val Thr Tyr Thr Asp Trp Arg Arg Asp Asn Phe Tyr Arg Ala Val
            100                 105                 110

Gln Gly Leu Thr Lys Gly Ala Arg Arg Val Gly Ile Glu Phe Asp His
        115                 120                 125

Val Ser Leu Asp Tyr Arg Gln Leu Leu Gln Asp Ala Leu Pro Gly Val
    130                 135                 140

Glu Leu Val Asp Val Ser Gln Pro Ser Met Trp Met Arg Thr Ile Lys
145                 150                 155                 160

Ser Ala Glu Glu Ile Lys Leu Ile Thr Glu Gly Ala Arg Ile Cys Asp
                165                 170                 175

Val Gly Gly Tyr Ala Val Ala Gly Ala Val Lys Ala Gly Val Pro Glu
            180                 185                 190

His Glu Val Ala Ile Ala Gly Thr Asn Ala Met Ile Arg Glu Ile Ala
        195                 200                 205

Lys Ser Phe Pro Phe Val Glu Leu Met Asp Thr Trp Thr Trp Phe Gln
    210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
        275                 280                 285

Gly Leu Glu Leu Met Lys Pro Gly Ala Arg Cys Met Asp Ile Ala Ile
    290                 295                 300

Glu Leu Asn Glu Met Tyr Arg Asp Trp Asp Leu Leu Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350
```

```
Gly Met Val Val Ser Met Glu Pro Met Val Met Ile Pro Glu Gly Gln
            355                 360                 365

Pro Gly Ala Gly Gly Tyr Arg Glu His Asp Ile Leu Val Ile Gly Glu
    370                 375                 380

Asp Gly Ala Glu Asn Ile Thr Gly Phe Pro Phe Gly Pro Glu His Asn
385                 390                 395                 400

Ile Val Gly Lys Gly
                405

<210> SEQ ID NO 19
<211> LENGTH: 405
<212> TYPE: PRT
<213> ORGANISM: Roseovarius sp
<220> FEATURE:
<221> NAME/KEY: mat_peptide
<222> LOCATION: (1)..(405)
<223> OTHER INFORMATION: Mutant creatine amidinohydrolase _Roseovarius
      sp. A3W1E4 with C175A+C299A substitutions

<400> SEQUENCE: 19

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Val Trp Met Ala Asp Asn Asn Val Asp Ala Ala Leu Phe Thr
        35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Asp Gln Lys Asn Ala Thr Thr Ile
65                  70                  75                  80

Ser Ala Gly Ile Asp Gly Gly Gln Pro Trp Arg Arg Thr Phe Gly Ser
                85                  90                  95

Asn Val Thr Tyr Thr Asp Trp Arg Arg Asp Asn Phe Tyr Arg Ala Val
            100                 105                 110

Gln Gly Leu Thr Lys Gly Ala Arg Arg Val Gly Ile Glu Phe Asp His
        115                 120                 125

Val Ser Leu Asp Tyr Arg Gln Leu Leu Gln Asp Ala Leu Pro Gly Val
    130                 135                 140

Glu Leu Val Asp Val Ser Gln Pro Ser Met Trp Met Arg Thr Ile Lys
145                 150                 155                 160

Ser Ala Glu Glu Ile Lys Leu Ile Thr Glu Gly Ala Arg Ile Ala Asp
                165                 170                 175

Val Gly Gly Tyr Ala Val Ala Gly Ala Val Lys Ala Gly Val Pro Glu
            180                 185                 190

His Glu Val Ala Ile Ala Gly Thr Asn Ala Met Ile Arg Glu Ile Ala
        195                 200                 205

Lys Ser Phe Pro Phe Val Glu Leu Met Asp Thr Trp Thr Trp Phe Gln
    210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
        275                 280                 285
```

```
Gly Leu Glu Leu Met Lys Pro Gly Ala Arg Ala Met Asp Ile Ala Ile
            290                 295                 300

Glu Leu Asn Glu Met Tyr Arg Asp Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Gln
                355                 360                 365

Pro Gly Ala Gly Gly Tyr Arg Glu His Asp Ile Leu Val Ile Gly Glu
            370                 375                 380

Asp Gly Ala Glu Asn Ile Thr Gly Phe Pro Phe Gly Pro Glu His Asn
385                 390                 395                 400

Ile Val Gly Lys Gly
                405

<210> SEQ ID NO 20
<211> LENGTH: 405
<212> TYPE: PRT
<213> ORGANISM: Roseovarius sp.
<220> FEATURE:
<221> NAME/KEY: mat_peptide
<222> LOCATION: (1)..(405)
<223> OTHER INFORMATION: Mutant creatine amidinohydrolase _Roseovarius
      sp. A3W1E4 with C175A+C299A-C268L substitutions

<400> SEQUENCE: 20

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Val Trp Met Ala Asp Asn Val Asp Ala Ala Leu Phe Thr
            35                  40                  45

Ser Tyr His Cys Ile Asn Tyr Tyr Ser Gly Trp Leu Tyr Cys Tyr Phe
50                  55                  60

Gly Arg Lys Tyr Gly Met Val Ile Asp Gln Lys Asn Ala Thr Thr Ile
65                  70                  75                  80

Ser Ala Gly Ile Asp Gly Gly Gln Pro Trp Arg Arg Thr Phe Gly Ser
                85                  90                  95

Asn Val Thr Tyr Thr Asp Trp Arg Arg Asp Asn Phe Tyr Arg Ala Val
            100                 105                 110

Gln Gly Leu Thr Lys Gly Ala Arg Arg Val Gly Ile Glu Phe Asp His
            115                 120                 125

Val Ser Leu Asp Tyr Arg Gln Leu Leu Gln Asp Ala Leu Pro Gly Val
            130                 135                 140

Glu Leu Val Asp Val Ser Gln Pro Ser Met Trp Met Arg Thr Ile Lys
145                 150                 155                 160

Ser Ala Glu Glu Ile Lys Leu Ile Thr Glu Gly Ala Arg Ile Ala Asp
                165                 170                 175

Val Gly Gly Tyr Ala Val Ala Gly Ala Val Lys Ala Gly Val Pro Glu
            180                 185                 190

His Glu Val Ala Ile Ala Gly Thr Asn Ala Met Ile Arg Glu Ile Ala
            195                 200                 205

Lys Ser Phe Pro Phe Val Glu Leu Met Asp Thr Trp Thr Trp Phe Gln
210                 215                 220
```

```
Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
            245                 250                 255

Gly Tyr Tyr Thr Ala Leu Glu Arg Thr Leu Phe Leu Asp His Val Asp
            260                 265                 270

Asp Ala Ser Leu Asp Ile Trp Glu Lys Asn Val Ala Val His Arg Arg
        275                 280                 285

Gly Leu Glu Leu Met Lys Pro Gly Ala Arg Ala Met Asp Ile Ala Ile
        290                 295                 300

Glu Leu Asn Glu Met Tyr Arg Asp Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Gln
            355                 360                 365

Pro Gly Ala Gly Gly Tyr Arg Glu His Asp Ile Leu Val Ile Gly Glu
        370                 375                 380

Asp Gly Ala Glu Asn Ile Thr Gly Phe Pro Phe Gly Pro Glu His Asn
385                 390                 395                 400

Ile Val Gly Lys Gly
            405

<210> SEQ ID NO 21
<211> LENGTH: 1215
<212> TYPE: DNA
<213> ORGANISM: Paracoccus denitrificans
<220> FEATURE:
<221> NAME/KEY: CDS
<222> LOCATION: (1)..(1215)
<223> OTHER INFORMATION: ABL69129.1 Paracoccus denitrificans PD1222 gene
      encoding creatine amidinohydrolase [A1B0T5]

<400> SEQUENCE: 21 atg acc gac gac atg ctt cat gtc atg gaa tgg cat aat ggc gat aag      48
Met Thr Asp Asp Met Leu His Val Met Glu Trp His Asn Gly Asp Lys
1               5                   10                  15 gat ttt tcc cct ttc tcg gat gcc gag atg cag cgg cgc cag gac gac      96
Asp Phe Ser Pro Phe Ser Asp Ala Glu Met Gln Arg Arg Gln Asp Asp
                20                  25                  30 atg cgc cgc tgg atg gcc ggg aac ggc gtc gat gcg gca ctg ttc acc     144
Met Arg Arg Trp Met Ala Gly Asn Gly Val Asp Ala Ala Leu Phe Thr
            35                  40                  45 tcg tat cac tgc atc aac tat tat tcg ggc tgg ctc tac tgc tat ttc     192
Ser Tyr His Cys Ile Asn Tyr Tyr Ser Gly Trp Leu Tyr Cys Tyr Phe
        50                  55                  60 ggc cgc aaa tac ggc atg gtc atc acc cag gac gcg gcg acc acc atc     240
Gly Arg Lys Tyr Gly Met Val Ile Thr Gln Asp Ala Ala Thr Thr Ile
65                  70                  75                  80 agc gcc ggc atc gat ggc ggt cag ccg tgg cgg cgc agc ttt ggc ggc     288
Ser Ala Gly Ile Asp Gly Gly Gln Pro Trp Arg Arg Ser Phe Gly Gly
                85                  90                  95 aac gtc acc tat acc gat tgg cgg cgc gac aat tat ttc cgc gcg gtg     336
Asn Val Thr Tyr Thr Asp Trp Arg Arg Asp Asn Tyr Phe Arg Ala Val
            100                 105                 110 cgg cag ctg acc ccc ggc gtc aag cgg ctg gga atc gag ttc gac cat     384
```

```
Arg Gln Leu Thr Pro Gly Val Lys Arg Leu Gly Ile Glu Phe Asp His
            115                 120                 125 gtc aac atg gac ttg cgc cgc cag ctt gag gca gcc ctg ccg ggg gtg      432
Val Asn Met Asp Leu Arg Arg Gln Leu Glu Ala Ala Leu Pro Gly Val
        130                 135                 140 gaa ttc gtc gat gtc ggc cag ccc tcg atg tgg atg cgc tcg atc aag      480
Glu Phe Val Asp Val Gly Gln Pro Ser Met Trp Met Arg Ser Ile Lys
145                 150                 155                 160 tcg gcc gag gaa cac aag ctg atc cgc gag ggc gcg cgc atc tgc gac      528
Ser Ala Glu Glu His Lys Leu Ile Arg Glu Gly Ala Arg Ile Cys Asp
                165                 170                 175 gtg ggc ggc gcg gcg gtg gcg gct gcg gtc aag gcg ggc gtg ccc gag      576
Val Gly Gly Ala Ala Val Ala Ala Ala Val Lys Ala Gly Val Pro Glu
            180                 185                 190 cac gag gtc gcc atc gcc tcg acc aat gcc atg atc cgc gag atc gcc      624
His Glu Val Ala Ile Ala Ser Thr Asn Ala Met Ile Arg Glu Ile Ala
        195                 200                 205 gcc tcc ttc ccc ttc gtc gag ctg atg gat acc tgg acc tgg ttc cag      672
Ala Ser Phe Pro Phe Val Glu Leu Met Asp Thr Trp Thr Trp Phe Gln
210                 215                 220 tcc ggc atc aac acc gac ggg gcg cat aac ccg gtg acg aac aag aag      720
Ser Gly Ile Asn Thr Asp Gly Ala His Asn Pro Val Thr Asn Lys Lys
225                 230                 235                 240 atc gca tcg ggc gag atc ctg tcg ctg aac tgc ttc ccg atg atc ttc      768
Ile Ala Ser Gly Glu Ile Leu Ser Leu Asn Cys Phe Pro Met Ile Phe
                245                 250                 255 ggc tat tat acc gcg ctg gaa cgc acg atg ttt tgc gac agc gtg gac      816
Gly Tyr Tyr Thr Ala Leu Glu Arg Thr Met Phe Cys Asp Ser Val Asp
            260                 265                 270 gat gcc agc ctc gac atc tgg gaa aag aac gtc gcc gtg cat cgc cgg      864
Asp Ala Ser Leu Asp Ile Trp Glu Lys Asn Val Ala Val His Arg Arg
        275                 280                 285 ggc ctg gaa ctg atc aag ccc ggt gcg aaa tgc aac gag atc gca ttg      912
Gly Leu Glu Leu Ile Lys Pro Gly Ala Lys Cys Asn Glu Ile Ala Leu
290                 295                 300 gag ctc aac gac atg tac cgc cag tgg gat ctg ctg aaa tat cgc agc      960
Glu Leu Asn Asp Met Tyr Arg Gln Trp Asp Leu Leu Lys Tyr Arg Ser
305                 310                 315                 320 ttc ggc tat ggc cac tcc ttc ggc gtc ctg agc cac tat tac ggg cgc     1008
Phe Gly Tyr Gly His Ser Phe Gly Val Leu Ser His Tyr Tyr Gly Arg
                325                 330                 335 gag gcc ggg gtc gag ctg cgc gag gac atc gag acc gag ctg aag ccc     1056
Glu Ala Gly Val Glu Leu Arg Glu Asp Ile Glu Thr Glu Leu Lys Pro
            340                 345                 350 ggc atg gtg gtc tcg atg gaa ccg atg gtg atg ttg ccc gag ggt gcg     1104
Gly Met Val Val Ser Met Glu Pro Met Val Met Leu Pro Glu Gly Ala
        355                 360                 365 ccc ggc gcg ggc ggc tat cgc gag cat gac atc ctg atc gtg acc gag     1152
Pro Gly Ala Gly Gly Tyr Arg Glu His Asp Ile Leu Ile Val Thr Glu
370                 375                 380 gac ggg gcc gat aac atc acc ggg ttc ccc ttc ggc ccc gag cac aac     1200
Asp Gly Ala Asp Asn Ile Thr Gly Phe Pro Phe Gly Pro Glu His Asn
385                 390                 395                 400 atc atc cgc aac tga                                                 1215
Ile Ile Arg Asn <210> SEQ ID NO 22
<211> LENGTH: 404
<212> TYPE: PRT
<213> ORGANISM: Paracoccus denitrificans
```

<400> SEQUENCE: 22

Met Thr Asp Asp Met Leu His Val Met Glu Trp His Asn Gly Asp Lys
1               5                   10                  15

Asp Phe Ser Pro Phe Ser Asp Ala Glu Met Gln Arg Arg Gln Asp Asp
            20                  25                  30

Met Arg Arg Trp Met Ala Gly Asn Gly Val Asp Ala Ala Leu Phe Thr
        35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Thr Gln Asp Ala Ala Thr Thr Ile
65              70                  75                  80

Ser Ala Gly Ile Asp Gly Gly Gln Pro Trp Arg Arg Ser Phe Gly Gly
                85                  90                  95

Asn Val Thr Tyr Thr Asp Trp Arg Arg Asp Asn Tyr Phe Arg Ala Val
                100                 105                 110

Arg Gln Leu Thr Pro Gly Val Lys Arg Leu Gly Ile Glu Phe Asp His
            115                 120                 125

Val Asn Met Asp Leu Arg Arg Gln Leu Glu Ala Ala Leu Pro Gly Val
130                 135                 140

Glu Phe Val Asp Val Gly Gln Pro Ser Met Trp Met Arg Ser Ile Lys
145                 150                 155                 160

Ser Ala Glu Glu His Lys Leu Ile Arg Glu Gly Ala Arg Ile Cys Asp
                165                 170                 175

Val Gly Gly Ala Ala Val Ala Ala Val Lys Ala Gly Val Pro Glu
                180                 185                 190

His Glu Val Ala Ile Ala Ser Thr Asn Ala Met Ile Arg Glu Ile Ala
                195                 200                 205

Ala Ser Phe Pro Phe Val Glu Leu Met Asp Thr Trp Thr Trp Phe Gln
            210                 215                 220

Ser Gly Ile Asn Thr Asp Gly Ala His Asn Pro Val Thr Asn Lys Lys
225                 230                 235                 240

Ile Ala Ser Gly Glu Ile Leu Ser Leu Asn Cys Phe Pro Met Ile Phe
                245                 250                 255

Gly Tyr Tyr Thr Ala Leu Glu Arg Thr Met Phe Cys Asp Ser Val Asp
                260                 265                 270

Asp Ala Ser Leu Asp Ile Trp Glu Lys Asn Val Ala Val His Arg Arg
            275                 280                 285

Gly Leu Glu Leu Ile Lys Pro Gly Ala Lys Cys Asn Glu Ile Ala Leu
            290                 295                 300

Glu Leu Asn Asp Met Tyr Arg Gln Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Thr Glu Leu Lys Pro
                340                 345                 350

Gly Met Val Val Ser Met Glu Pro Met Val Met Leu Pro Glu Gly Ala
            355                 360                 365

Pro Gly Ala Gly Gly Tyr Arg Glu His Asp Ile Leu Ile Val Thr Glu
            370                 375                 380

Asp Gly Ala Asp Asn Ile Thr Gly Phe Pro Phe Gly Pro Glu His Asn
385                 390                 395                 400

Ile Ile Arg Asn

<210> SEQ ID NO 23
<211> LENGTH: 404
<212> TYPE: PRT
<213> ORGANISM: Paracoccus denitrificans
<220> FEATURE:
<221> NAME/KEY: mat_peptide
<222> LOCATION: (1)..(404)
<223> OTHER INFORMATION: Mutant creatine amidinohydrolase _Paracoccus denitrificans A1B0T5 with C175A+C299A substitutions

<400> SEQUENCE: 23

```
Met Thr Asp Asp Met Leu His Val Met Glu Trp His Asn Gly Asp Lys
1               5                   10                  15

Asp Phe Ser Pro Phe Ser Asp Ala Glu Met Gln Arg Arg Gln Asp Asp
            20                  25                  30

Met Arg Arg Trp Met Ala Gly Asn Gly Val Asp Ala Ala Leu Phe Thr
        35                  40                  45

Ser Tyr His Cys Ile Asn Tyr Tyr Ser Gly Trp Leu Tyr Cys Tyr Phe
50                  55                  60

Gly Arg Lys Tyr Gly Met Val Ile Thr Gln Asp Ala Ala Thr Thr Ile
65                  70                  75                  80

Ser Ala Gly Ile Asp Gly Gly Gln Pro Trp Arg Arg Ser Phe Gly Gly
            85                  90                  95

Asn Val Thr Tyr Thr Asp Trp Arg Arg Asp Asn Tyr Phe Arg Ala Val
            100                 105                 110

Arg Gln Leu Thr Pro Gly Val Lys Arg Leu Gly Ile Glu Phe Asp His
        115                 120                 125

Val Asn Met Asp Leu Arg Arg Gln Leu Glu Ala Ala Leu Pro Gly Val
130                 135                 140

Glu Phe Val Asp Val Gly Gln Pro Ser Met Trp Met Arg Ser Ile Lys
145                 150                 155                 160

Ser Ala Glu Glu His Lys Leu Ile Arg Glu Gly Ala Arg Ile Ala Asp
            165                 170                 175

Val Gly Gly Ala Ala Val Ala Ala Ala Val Lys Ala Gly Val Pro Glu
            180                 185                 190

His Glu Val Ala Ile Ala Ser Thr Asn Ala Met Ile Arg Glu Ile Ala
        195                 200                 205

Ala Ser Phe Pro Phe Val Glu Leu Met Asp Thr Trp Thr Trp Phe Gln
210                 215                 220

Ser Gly Ile Asn Thr Asp Gly Ala His Asn Pro Val Thr Asn Lys Lys
225                 230                 235                 240

Ile Ala Ser Gly Glu Ile Leu Ser Leu Asn Cys Phe Pro Met Ile Phe
            245                 250                 255

Gly Tyr Tyr Thr Ala Leu Glu Arg Thr Met Phe Cys Asp Ser Val Asp
            260                 265                 270

Asp Ala Ser Leu Asp Ile Trp Glu Lys Asn Val Ala Val His Arg Arg
        275                 280                 285

Gly Leu Glu Leu Ile Lys Pro Gly Ala Lys Ala Asn Glu Ile Ala Leu
290                 295                 300

Glu Leu Asn Asp Met Tyr Arg Gln Trp Asp Leu Leu Tyr Arg Ser
305                 310                 315                 320

Phe Gly Tyr Gly His Ser Phe Gly Val Leu Ser His Tyr Tyr Gly Arg
            325                 330                 335

Glu Ala Gly Val Glu Leu Arg Glu Asp Ile Glu Thr Glu Leu Lys Pro
            340                 345                 350
```

```
Gly Met Val Val Ser Met Glu Pro Met Val Met Leu Pro Glu Gly Ala
            355                 360                 365
Pro Gly Ala Gly Gly Tyr Arg Glu His Asp Ile Leu Ile Val Thr Glu
370                 375                 380
Asp Gly Ala Asp Asn Ile Thr Gly Phe Pro Phe Gly Pro Glu His Asn
385                 390                 395                 400
Ile Ile Arg Asn

<210> SEQ ID NO 24
<211> LENGTH: 404
<212> TYPE: PRT
<213> ORGANISM: Paracoccus denitrificans
<220> FEATURE:
<221> NAME/KEY: mat_peptide
<222> LOCATION: (1)..(404)
<223> OTHER INFORMATION: Mutant creatine amidinohydrolase _Paracoccus
      denitrificans A1B0T5 with C175A+C299A+C268L substitutions

<400> SEQUENCE: 24

Met Thr Asp Asp Met Leu His Val Met Glu Trp His Asn Gly Asp Lys
1               5                   10                  15
Asp Phe Ser Pro Phe Ser Asp Ala Glu Met Gln Arg Arg Gln Asp Asp
            20                  25                  30
Met Arg Arg Trp Met Ala Gly Asn Gly Val Asp Ala Ala Leu Phe Thr
        35                  40                  45
Ser Tyr His Cys Ile Asn Tyr Tyr Ser Gly Trp Leu Tyr Cys Tyr Phe
    50                  55                  60
Gly Arg Lys Tyr Gly Met Val Ile Thr Gln Asp Ala Ala Thr Thr Ile
65                  70                  75                  80
Ser Ala Gly Ile Asp Gly Gly Gln Pro Trp Arg Arg Ser Phe Gly Gly
            85                  90                  95
Asn Val Thr Tyr Thr Asp Trp Arg Arg Asp Asn Tyr Phe Arg Ala Val
            100                 105                 110
Arg Gln Leu Thr Pro Gly Val Lys Arg Leu Gly Ile Glu Phe Asp His
        115                 120                 125
Val Asn Met Asp Leu Arg Arg Gln Leu Glu Ala Ala Leu Pro Gly Val
    130                 135                 140
Glu Phe Val Asp Val Gly Gln Pro Ser Met Trp Met Arg Ser Ile Lys
145                 150                 155                 160
Ser Ala Glu Glu His Lys Leu Ile Arg Glu Gly Ala Arg Ile Ala Asp
            165                 170                 175
Val Gly Gly Ala Ala Val Ala Ala Val Lys Ala Gly Val Pro Glu
            180                 185                 190
His Glu Val Ala Ile Ala Ser Thr Asn Ala Met Ile Arg Glu Ile Ala
        195                 200                 205
Ala Ser Phe Pro Phe Val Glu Leu Met Asp Thr Trp Thr Trp Phe Gln
    210                 215                 220
Ser Gly Ile Asn Thr Asp Gly Ala His Asn Pro Val Thr Asn Lys Lys
225                 230                 235                 240
Ile Ala Ser Gly Glu Ile Leu Ser Leu Asn Cys Phe Pro Met Ile Phe
            245                 250                 255
Gly Tyr Tyr Thr Ala Leu Glu Arg Thr Met Phe Leu Asp Ser Val Asp
            260                 265                 270
Asp Ala Ser Leu Asp Ile Trp Glu Lys Asn Val Ala Val His Arg Arg
        275                 280                 285
```

```
Gly Leu Glu Leu Ile Lys Pro Gly Ala Lys Ala Asn Glu Ile Ala Leu
            290                 295                 300

Glu Leu Asn Asp Met Tyr Arg Gln Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Glu Thr Glu Leu Lys Pro
            340                 345                 350

Gly Met Val Val Ser Met Glu Pro Met Val Met Leu Pro Glu Gly Ala
        355                 360                 365

Pro Gly Ala Gly Gly Tyr Arg Glu His Asp Ile Leu Ile Val Thr Glu
370                 375                 380

Asp Gly Ala Asp Asn Ile Thr Gly Phe Pro Phe Gly Pro Glu His Asn
385                 390                 395                 400

Ile Ile Arg Asn

<210> SEQ ID NO 25
<211> LENGTH: 1215
<212> TYPE: DNA
<213> ORGANISM: Rubellimicrobium mesophilum
<220> FEATURE:
<221> NAME/KEY: CDS
<222> LOCATION: (1)..(1215)
<223> OTHER INFORMATION: EYD77030.1 Rubellimicrobium mesophilum DSM
      19309 gene encoding creatine amidinohydrolase [A0A017HRV0]

<400> SEQUENCE: 25 atg gcc gag gac atg ctg cac gta atg gga tgg cac aac ggg gat aag      48
Met Ala Glu Asp Met Leu His Val Met Gly Trp His Asn Gly Asp Lys
1               5                   10                  15 gaa tat tca ccc ttc tcc gag gcc gag atg agc cga cgg caa ggc gat      96
Glu Tyr Ser Pro Phe Ser Glu Ala Glu Met Ser Arg Arg Gln Gly Asp
            20                  25                  30 atc cgg aca tgg atg gcc gag aac gac gtc gat gcc gcg ctg ttc acg     144
Ile Arg Thr Trp Met Ala Glu Asn Asp Val Asp Ala Ala Leu Phe Thr
        35                  40                  45 tcc tat cat tgc atc aat tac tat tcc ggc tgg ctc tat tgc caa ttc     192
Ser Tyr His Cys Ile Asn Tyr Tyr Ser Gly Trp Leu Tyr Cys Gln Phe
    50                  55                  60 ggc cgg aga tac gga atg atc gtc acc cag gac agg gcg ctg acg gtg     240
Gly Arg Arg Tyr Gly Met Ile Val Thr Gln Asp Arg Ala Leu Thr Val
65                  70                  75                  80 tcc gcc ggg atc gac ggc ggc cag ccc tgg cga cgg agc ttc ggc gac     288
Ser Ala Gly Ile Asp Gly Gly Gln Pro Trp Arg Arg Ser Phe Gly Asp
                85                  90                  95 aac atc acc tac acc gat tgg cgg cgc gac aac ttc tac cgt gcg gtg     336
Asn Ile Thr Tyr Thr Asp Trp Arg Arg Asp Asn Phe Tyr Arg Ala Val
            100                 105                 110 cgc cag aac ctg ccg ggc gtg agg cgc ctc gga atc gag ttc gac cac     384
Arg Gln Asn Leu Pro Gly Val Arg Arg Leu Gly Ile Glu Phe Asp His
        115                 120                 125 gtc tcg ctc gac ttc cga cgt cag ctc ggc gag gcg ctg ccg ggc gtg     432
Val Ser Leu Asp Phe Arg Arg Gln Leu Gly Glu Ala Leu Pro Gly Val
    130                 135                 140 gag ttc gtg gac gtg ggc cag ccc tcg atg tgg atg cgg acc atc aag     480
Glu Phe Val Asp Val Gly Gln Pro Ser Met Trp Met Arg Thr Ile Lys
145                 150                 155                 160 tcc gag gag gag cgg agg ctc atc cgc gag ggc gcg cgg gtc tgc gac     528
Ser Glu Glu Glu Arg Arg Leu Ile Arg Glu Gly Ala Arg Val Cys Asp
                165                 170                 175
```

| | | | | | | | | | | | | | | | |
|---|---|---|---|---|---|---|---|---|---|---|---|---|---|---|---|
| gtc | ggt | ggc | gcg | gcg | gtg | gcg | gag | gcg | gtg | agg | gcg | ggc | gtg | ccc | gag | 576
| Val | Gly | Gly | Ala | Ala | Val | Ala | Glu | Ala | Val | Arg | Ala | Gly | Val | Pro | Glu |
| | | | 180 | | | | | 185 | | | | | 190 | | |

```
gtc ggt ggc gcg gcg gtg gcg gag gcg gtg agg gcg ggc gtg ccc gag      576
Val Gly Gly Ala Ala Val Ala Glu Ala Val Arg Ala Gly Val Pro Glu
            180                 185                 190 cat gag gtc gcc atc gcc tcg acc aat gcg atg atc cgc gag atc gcg      624
His Glu Val Ala Ile Ala Ser Thr Asn Ala Met Ile Arg Glu Ile Ala
                195                 200                 205 agg tcg ttc ccc tat gtg gag ctg atg gac acc tgg acc tgg ttc cag      672
Arg Ser Phe Pro Tyr Val Glu Leu Met Asp Thr Trp Thr Trp Phe Gln
    210                 215                 220 tcg ggc atc aac acc gat ggc gcg cac aac ccg gtc acc aat cgc gtg      720
Ser Gly Ile Asn Thr Asp Gly Ala His Asn Pro Val Thr Asn Arg Val
225                 230                 235                 240 gtc cag tcg ggg gac atc ctg tcg ctc aac tgc ttc ccg atg atc ttc      768
Val Gln Ser Gly Asp Ile Leu Ser Leu Asn Cys Phe Pro Met Ile Phe
                245                 250                 255 ggc tac tac acc gcg ctg gag cgg acg atg ttc tgc gac cac gtg gac      816
Gly Tyr Tyr Thr Ala Leu Glu Arg Thr Met Phe Cys Asp His Val Asp
            260                 265                 270 gac gcg agc ctc gac atc tgg gag aag aac gtg gcc gtc cac cgg cgg      864
Asp Ala Ser Leu Asp Ile Trp Glu Lys Asn Val Ala Val His Arg Arg
        275                 280                 285 ggg ctg gag ctg atc cga ccc ggg gcg aag tgc aac gag atc gcc gcc      912
Gly Leu Glu Leu Ile Arg Pro Gly Ala Lys Cys Asn Glu Ile Ala Ala
    290                 295                 300 gag ctg aac gag atg tac cgg cag tgg gac ctg ctg cag tat cgc agc      960
Glu Leu Asn Glu Met Tyr Arg Gln Trp Asp Leu Leu Gln Tyr Arg Ser
305                 310                 315                 320 ttc ggc tac ggg cat tcc ttc ggg gtg ctc tgc cac tac tac ggc cgc     1008
Phe Gly Tyr Gly His Ser Phe Gly Val Leu Cys His Tyr Tyr Gly Arg
                325                 330                 335 gag gcg ggc gtg gag ctg cgg gag gac atc gac acc gag ctg aag ccc     1056
Glu Ala Gly Val Glu Leu Arg Glu Asp Ile Asp Thr Glu Leu Lys Pro
            340                 345                 350 ggg atg gtc gtc tcc atg gag ccc atg gtg atg atc ccg aac ggc aac     1104
Gly Met Val Val Ser Met Glu Pro Met Val Met Ile Pro Asn Gly Asn
        355                 360                 365 ccc ggg gcg ggc ggc tac cgc gag cac gac ata ctg atc gtg acc gag     1152
Pro Gly Ala Gly Gly Tyr Arg Glu His Asp Ile Leu Ile Val Thr Glu
    370                 375                 380 gat ggg gcg gag aac atc acc aag ttc ccc ttc ggc ccc gag cac aac     1200
Asp Gly Ala Glu Asn Ile Thr Lys Phe Pro Phe Gly Pro Glu His Asn
385                 390                 395                 400 gtc atc cgc aac tga                                                  1215
Val Ile Arg Asn <210> SEQ ID NO 26
<211> LENGTH: 404
<212> TYPE: PRT
<213> ORGANISM: Rubellimicrobium mesophilum

<400> SEQUENCE: 26

Met Ala Glu Asp Met Leu His Val Met Gly Trp His Asn Gly Asp Lys
1               5                   10                  15

Glu Tyr Ser Pro Phe Ser Glu Ala Glu Met Ser Arg Arg Gln Gly Asp
            20                  25                  30

Ile Arg Thr Trp Met Ala Glu Asn Asp Val Asp Ala Ala Leu Phe Thr
        35                  40                  45

Ser Tyr His Cys Ile Asn Tyr Ser Gly Trp Leu Tyr Cys Gln Phe
    50                  55                  60
```

Gly Arg Arg Tyr Gly Met Ile Val Thr Gln Asp Arg Ala Leu Thr Val
65                  70                  75                  80

Ser Ala Gly Ile Asp Gly Gly Gln Pro Trp Arg Arg Ser Phe Gly Asp
                85                  90                  95

Asn Ile Thr Tyr Thr Asp Trp Arg Arg Asp Asn Phe Tyr Arg Ala Val
            100                 105                 110

Arg Gln Asn Leu Pro Gly Val Arg Arg Leu Gly Ile Glu Phe Asp His
        115                 120                 125

Val Ser Leu Asp Phe Arg Arg Gln Leu Gly Glu Ala Leu Pro Gly Val
    130                 135                 140

Glu Phe Val Asp Val Gly Gln Pro Ser Met Trp Met Arg Thr Ile Lys
145                 150                 155                 160

Ser Glu Glu Arg Arg Leu Ile Arg Glu Gly Ala Arg Val Cys Asp
                165                 170                 175

Val Gly Gly Ala Ala Val Ala Glu Ala Val Arg Ala Gly Val Pro Glu
                180                 185                 190

His Glu Val Ala Ile Ala Ser Thr Asn Ala Met Ile Arg Glu Ile Ala
            195                 200                 205

Arg Ser Phe Pro Tyr Val Glu Leu Met Asp Thr Trp Thr Trp Phe Gln
210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Cys Phe Pro Met Ile Phe
                245                 250                 255

Gly Tyr Tyr Thr Ala Leu Glu Arg Thr Met Phe Cys Asp His Val Asp
            260                 265                 270

Asp Ala Ser Leu Asp Ile Trp Glu Lys Asn Val Ala Val His Arg Arg
            275                 280                 285

Gly Leu Glu Leu Ile Arg Pro Gly Ala Lys Cys Asn Glu Ile Ala Ala
290                 295                 300

Glu Leu Asn Glu Met Tyr Arg Gln Trp Asp Leu Leu Gln Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Gly Asp Ile Asp Thr Glu Leu Lys Pro
            340                 345                 350

Gly Met Val Val Ser Met Glu Pro Met Val Met Ile Pro Asn Gly Asn
                355                 360                 365

Pro Gly Ala Gly Gly Tyr Arg Glu His Asp Ile Leu Ile Val Thr Glu
            370                 375                 380

Asp Gly Ala Glu Asn Ile Thr Lys Phe Pro Phe Gly Pro Glu His Asn
385                 390                 395                 400

Val Ile Arg Asn

<210> SEQ ID NO 27
<211> LENGTH: 404
<212> TYPE: PRT
<213> ORGANISM: Rubellimicrobium mesophilum
<220> FEATURE:
<221> NAME/KEY: mat_peptide
<222> LOCATION: (1)..(404)
<223> OTHER INFORMATION: Mutant creatine amidinohydrolase _Rubelli-
      microbium mesophilum A0A017HRV0 with C175A+C299A substitutions

<400> SEQUENCE: 27

```
Met Ala Glu Asp Met Leu His Val Met Gly Trp His Asn Gly Asp Lys
1               5                   10                  15
Glu Tyr Ser Pro Phe Ser Glu Ala Glu Met Ser Arg Arg Gln Gly Asp
            20                  25                  30
Ile Arg Thr Trp Met Ala Glu Asn Asp Val Asp Ala Ala Leu Phe Thr
        35                  40                  45
Ser Tyr His Cys Ile Asn Tyr Tyr Ser Gly Trp Leu Tyr Cys Gln Phe
50                  55                  60
Gly Arg Arg Tyr Gly Met Ile Val Thr Gln Asp Arg Ala Leu Thr Val
65                      70                  75                  80
Ser Ala Gly Ile Asp Gly Gly Gln Pro Trp Arg Arg Ser Phe Gly Asp
                85                  90                  95
Asn Ile Thr Tyr Thr Asp Trp Arg Arg Asp Asn Phe Tyr Arg Ala Val
                100                 105                 110
Arg Gln Asn Leu Pro Gly Val Arg Arg Leu Gly Ile Glu Phe Asp His
            115                 120                 125
Val Ser Leu Asp Phe Arg Arg Gln Leu Gly Glu Ala Leu Pro Gly Val
    130                 135                 140
Glu Phe Val Asp Val Gly Gln Pro Ser Met Trp Met Arg Thr Ile Lys
145                 150                 155                 160
Ser Glu Glu Glu Arg Arg Leu Ile Arg Glu Gly Ala Arg Val Ala Asp
            165                 170                 175
Val Gly Gly Ala Ala Val Ala Glu Val Arg Ala Gly Val Pro Glu
                180                 185                 190
His Glu Val Ala Ile Ala Ser Thr Asn Ala Met Ile Arg Glu Ile Ala
            195                 200                 205
Arg Ser Phe Pro Tyr Val Glu Leu Met Asp Thr Trp Thr Trp Phe Gln
    210                 215                 220
Ser Gly Ile Asn Thr Asp Gly Ala His Asn Pro Val Thr Asn Arg Val
225                 230                 235                 240
Val Gln Ser Gly Asp Ile Leu Ser Leu Asn Cys Phe Pro Met Ile Phe
                245                 250                 255
Gly Tyr Tyr Thr Ala Leu Glu Arg Thr Met Phe Cys Asp His Val Asp
            260                 265                 270
Asp Ala Ser Leu Asp Ile Trp Glu Lys Asn Val Ala Val His Arg Arg
    275                 280                 285
Gly Leu Glu Leu Ile Arg Pro Gly Ala Lys Ala Asn Glu Ile Ala Ala
290                 295                 300
Glu Leu Asn Glu Met Tyr Arg Gln Trp Asp Leu Leu Gln Tyr Arg Ser
305                 310                 315                 320
Phe Gly Tyr Gly His Ser Phe Gly Val Leu Cys His Tyr Tyr Gly Arg
                325                 330                 335
Glu Ala Gly Val Glu Leu Arg Glu Asp Ile Asp Thr Glu Leu Lys Pro
            340                 345                 350
Gly Met Val Val Ser Met Glu Pro Met Val Met Ile Pro Asn Gly Asn
                355                 360                 365
Pro Gly Ala Gly Gly Tyr Arg Glu His Asp Ile Leu Ile Val Thr Glu
370                 375                 380
Asp Gly Ala Glu Asn Ile Thr Lys Phe Pro Phe Gly Pro Glu His Asn
385                 390                 395                 400
Val Ile Arg Asn

<210> SEQ ID NO 28
```

<211> LENGTH: 404
<212> TYPE: PRT
<213> ORGANISM: Rubellimicrobium mesophilum
<220> FEATURE:
<221> NAME/KEY: mat_peptide
<222> LOCATION: (1)..(404)
<223> OTHER INFORMATION: Mutant creatine amidinohydrolase
_Rubellimicrobium mesophilum A0A017HRV0 with C175A+C299A+C268L
substitutions

<400> SEQUENCE: 28

```
Met Ala Glu Asp Met Leu His Val Met Gly Trp His Asn Gly Asp Lys
1               5                   10                  15

Glu Tyr Ser Pro Phe Ser Glu Ala Glu Met Ser Arg Arg Gln Gly Asp
            20                  25                  30

Ile Arg Thr Trp Met Ala Glu Asn Asp Val Asp Ala Ala Leu Phe Thr
        35                  40                  45

Ser Tyr His Cys Ile Asn Tyr Tyr Ser Gly Trp Leu Tyr Cys Gln Phe
    50                  55                  60

Gly Arg Arg Tyr Gly Met Ile Val Thr Gln Asp Arg Ala Leu Thr Val
65                  70                  75                  80

Ser Ala Gly Ile Asp Gly Gly Gln Pro Trp Arg Arg Ser Phe Gly Asp
            85                  90                  95

Asn Ile Thr Tyr Thr Asp Trp Arg Arg Asp Asn Phe Tyr Arg Ala Val
            100                 105                 110

Arg Gln Asn Leu Pro Gly Val Arg Arg Leu Gly Ile Glu Phe Asp His
        115                 120                 125

Val Ser Leu Asp Phe Arg Arg Gln Leu Gly Glu Ala Leu Pro Gly Val
130                 135                 140

Glu Phe Val Asp Val Gly Gln Pro Ser Met Trp Met Arg Thr Ile Lys
145                 150                 155                 160

Ser Glu Glu Glu Arg Arg Leu Ile Arg Glu Gly Ala Arg Val Ala Asp
                165                 170                 175

Val Gly Gly Ala Ala Val Ala Glu Ala Val Arg Ala Gly Val Pro Glu
            180                 185                 190

His Glu Val Ala Ile Ala Ser Thr Asn Ala Met Ile Arg Glu Ile Ala
        195                 200                 205

Arg Ser Phe Pro Tyr Val Glu Leu Met Asp Thr Trp Thr Trp Phe Gln
    210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Cys Phe Pro Met Ile Phe
                245                 250                 255

Gly Tyr Tyr Thr Ala Leu Glu Arg Thr Met Phe Leu Asp His Val Asp
            260                 265                 270

Asp Ala Ser Leu Asp Ile Trp Glu Lys Asn Val Ala Val His Arg Arg
        275                 280                 285

Gly Leu Glu Leu Ile Arg Pro Gly Ala Lys Ala Asn Glu Ile Ala Ala
    290                 295                 300

Glu Leu Asn Glu Met Tyr Arg Gln Trp Asp Leu Leu Gln Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Asp Thr Glu Leu Lys Pro
            340                 345                 350

Gly Met Val Val Ser Met Glu Pro Met Val Met Ile Pro Asn Gly Asn
```

```
                    355                 360                 365
Pro Gly Ala Gly Gly Tyr Arg Glu His Asp Ile Leu Ile Val Thr Glu
            370                 375                 380

Asp Gly Ala Glu Asn Ile Thr Lys Phe Pro Phe Gly Pro Glu His Asn
385                 390                 395                 400

Val Ile Arg Asn

<210> SEQ ID NO 29
<211> LENGTH: 1215
<212> TYPE: DNA
<213> ORGANISM: Loktanella vestfoldensis
<220> FEATURE:
<221> NAME/KEY: CDS
<222> LOCATION: (1)..(1215)
<223> OTHER INFORMATION: EAQ08246.1 Loktanella vestfoldensis SKA53 gene
      encoding creatine amidinohydrolase [A3V128]

<400> SEQUENCE: 29 atg gac gac atg ctc cac gtc atg gaa tgg cac aac ggc gag aag gag      48
Met Asp Asp Met Leu His Val Met Glu Trp His Asn Gly Glu Lys Glu
1               5                   10                  15 ttc tcg ccc ttt tca gat aac gaa atg gcc cgt cgc cag aac gaa ttg      96
Phe Ser Pro Phe Ser Asp Asn Glu Met Ala Arg Arg Gln Asn Glu Leu
                20                  25                  30 cgc gac tgg atg ggc aag aac gat gtc gat gca tca ctc ttc acc tct     144
Arg Asp Trp Met Gly Lys Asn Asp Val Asp Ala Ser Leu Phe Thr Ser
            35                  40                  45 tat cac tgc atc aac tat tat agc gga tgg ctg tac tgc tat ttc ggt     192
Tyr His Cys Ile Asn Tyr Tyr Ser Gly Trp Leu Tyr Cys Tyr Phe Gly
        50                  55                  60 cgt aaa tac ggc atg gtc atc gac cag aag aac gcc act acg atc tct     240
Arg Lys Tyr Gly Met Val Ile Asp Gln Lys Asn Ala Thr Thr Ile Ser
65                  70                  75                  80 gcc ggc atc gac ggc ggc caa ccc ttc cgt cgc agc ttc ggc aac aac     288
Ala Gly Ile Asp Gly Gly Gln Pro Phe Arg Arg Ser Phe Gly Asn Asn
                85                  90                  95 atc acg tat act gac tgg cgt cgt gac aac ttc tac cgc gcg atc cag     336
Ile Thr Tyr Thr Asp Trp Arg Arg Asp Asn Phe Tyr Arg Ala Ile Gln
            100                 105                 110 caa ctg aca ccg ggt gcc aag cgc atc ggt atc gaa ttc gac cac gtg     384
Gln Leu Thr Pro Gly Ala Lys Arg Ile Gly Ile Glu Phe Asp His Val
        115                 120                 125 tcg ctg gaa tac cgc caa ctg ctt cag gat gcc ctg ccg ggc gtc gag     432
Ser Leu Glu Tyr Arg Gln Leu Leu Gln Asp Ala Leu Pro Gly Val Glu
    130                 135                 140 ttc gtt gac gtc ggt cag ccc gcg atg tgg atg cgg acg atc aag tcg     480
Phe Val Asp Val Gly Gln Pro Ala Met Trp Met Arg Thr Ile Lys Ser
145                 150                 155                 160 gcc gaa gaa atc aag ctg atc aaa gaa ggc gcc cgc gtc gcc gac gtt     528
Ala Glu Glu Ile Lys Leu Ile Lys Glu Gly Ala Arg Val Ala Asp Val
                165                 170                 175 ggc ggt gct gct gtg gcc gct gcg gtc aaa gcc ggt gtt ccc gaa cac     576
Gly Gly Ala Ala Val Ala Ala Ala Val Lys Ala Gly Val Pro Glu His
            180                 185                 190 gaa gtc gcc att gcc agt acc aat gcg atg atc cgc gag att gcc aac     624
Glu Val Ala Ile Ala Ser Thr Asn Ala Met Ile Arg Glu Ile Ala Asn
        195                 200                 205 tct ttc ccc ttc gtc gaa ttg atg gac acc tgg acc tgg ttc cag tcc     672
Ser Phe Pro Phe Val Glu Leu Met Asp Thr Trp Thr Trp Phe Gln Ser
    210                 215                 220
```

```
ggc att aac acc gac ggc gcg cac aac ccg gta acg aac aag aaa gtg      720
Gly Ile Asn Thr Asp Gly Ala His Asn Pro Val Thr Asn Lys Lys Val
225                 230                 235                 240 cag tcg ggt gaa atc ctc agc ctc aac act ttc ccg atg atc ttt ggc      768
Gln Ser Gly Glu Ile Leu Ser Leu Asn Thr Phe Pro Met Ile Phe Gly
                245                 250                 255 tac tac acg gcg ctg gaa cgc aca ctg ttc tgc gac cac gtt gat gat      816
Tyr Tyr Thr Ala Leu Glu Arg Thr Leu Phe Cys Asp His Val Asp Asp
            260                 265                 270 gca agc ctc gat atc tgg gag aag aac gtc aag gtc cac gag cgt gga      864
Ala Ser Leu Asp Ile Trp Glu Lys Asn Val Lys Val His Glu Arg Gly
        275                 280                 285 ctc gag ttg atc aag ccg ggc gcg cgc tgc atg gat atc gcg atc gag      912
Leu Glu Leu Ile Lys Pro Gly Ala Arg Cys Met Asp Ile Ala Ile Glu
    290                 295                 300 ctc aac gag atg tat cgc gaa tgg gac ctg ctg aag tat cgt tcg ttc      960
Leu Asn Glu Met Tyr Arg Glu Trp Asp Leu Leu Lys Tyr Arg Ser Phe
305                 310                 315                 320 gga tac ggc cac agc ttt ggc gtt ctg agc cat tac tat ggc cgc gag     1008
Gly Tyr Gly His Ser Phe Gly Val Leu Ser His Tyr Tyr Gly Arg Glu
                325                 330                 335 gct ggc gta gaa ctt cgc gaa gac att gaa acg gag ctc aag cca gga     1056
Ala Gly Val Glu Leu Arg Glu Asp Ile Glu Thr Glu Leu Lys Pro Gly
            340                 345                 350 atg gtc gtg tcc atg gag ccc atg gtc atg atc ccg gaa ggt cag cct     1104
Met Val Val Ser Met Glu Pro Met Val Met Ile Pro Glu Gly Gln Pro
        355                 360                 365 ggc gct ggc ggc tac cgt gag cat gac atc cta gtg atc ggc gag gac     1152
Gly Ala Gly Gly Tyr Arg Glu His Asp Ile Leu Val Ile Gly Glu Asp
    370                 375                 380 aac aca gtc gag aac atc acc gga ttc cca ttc ggc ccc gag cac aat     1200
Asn Thr Val Glu Asn Ile Thr Gly Phe Pro Phe Gly Pro Glu His Asn
385                 390                 395                 400 gtc atc aag aac taa                                                  1215
Val Ile Lys Asn <210> SEQ ID NO 30
<211> LENGTH: 404
<212> TYPE: PRT
<213> ORGANISM: Loktanella vestfoldensis

<400> SEQUENCE: 30

Met Asp Asp Met Leu His Val Met Glu Trp His Asn Gly Lys Glu
1               5                   10                  15

Phe Ser Pro Phe Ser Asp Asn Glu Met Ala Arg Arg Gln Asn Glu Leu
                20                  25                  30

Arg Asp Trp Met Gly Lys Asn Asp Val Asp Ala Ser Leu Phe Thr Ser
            35                  40                  45

Tyr His Cys Ile Asn Tyr Tyr Ser Gly Trp Leu Tyr Cys Tyr Phe Gly
        50                  55                  60

Arg Lys Tyr Gly Met Val Ile Asp Gln Lys Asn Ala Thr Thr Ile Ser
65                  70                  75                  80

Ala Gly Ile Asp Gly Gly Gln Pro Phe Arg Arg Ser Phe Gly Asn Asn
                85                  90                  95

Ile Thr Tyr Thr Asp Trp Arg Arg Asp Asn Phe Tyr Arg Ala Ile Gln
            100                 105                 110

Gln Leu Thr Pro Gly Ala Lys Arg Ile Gly Ile Glu Phe Asp His Val
        115                 120                 125
```

Ser Leu Glu Tyr Arg Gln Leu Leu Gln Asp Ala Leu Pro Gly Val Glu
   130                 135                 140

Phe Val Asp Val Gly Gln Pro Ala Met Trp Met Arg Thr Ile Lys Ser
145                 150                 155                 160

Ala Glu Glu Ile Lys Leu Ile Lys Glu Gly Ala Arg Val Ala Asp Val
                165                 170                 175

Gly Gly Ala Ala Val Ala Ala Val Lys Ala Gly Val Pro Glu His
            180                 185                 190

Glu Val Ala Ile Ala Ser Thr Asn Ala Met Ile Arg Glu Ile Ala Asn
                195                 200                 205

Ser Phe Pro Phe Val Glu Leu Met Asp Thr Trp Thr Trp Phe Gln Ser
   210                 215                 220

Gly Ile Asn Thr Asp Gly Ala His Asn Pro Val Thr Asn Lys Lys Val
225                 230                 235                 240

Gln Ser Gly Glu Ile Leu Ser Leu Asn Thr Phe Pro Met Ile Phe Gly
                245                 250                 255

Tyr Tyr Thr Ala Leu Glu Arg Thr Leu Phe Cys Asp His Val Asp Asp
            260                 265                 270

Ala Ser Leu Asp Ile Trp Glu Lys Asn Val Lys Val His Glu Arg Gly
   275                 280                 285

Leu Glu Leu Ile Lys Pro Gly Ala Arg Cys Met Asp Ile Ala Ile Glu
290                 295                 300

Leu Asn Glu Met Tyr Arg Glu Trp Asp Leu Leu Lys Tyr Arg Ser Phe
305                 310                 315                 320

Gly Tyr Gly His Ser Phe Gly Val Leu Ser His Tyr Tyr Gly Arg Glu
                325                 330                 335

Ala Gly Val Glu Leu Arg Glu Asp Ile Glu Thr Glu Leu Lys Pro Gly
            340                 345                 350

Met Val Val Ser Met Glu Pro Met Val Met Ile Pro Glu Gly Gln Pro
   355                 360                 365

Gly Ala Gly Gly Tyr Arg Glu His Asp Ile Leu Val Ile Gly Glu Asp
370                 375                 380

Asn Thr Val Glu Asn Ile Thr Gly Phe Pro Phe Gly Pro Glu His Asn
385                 390                 395                 400

Val Ile Lys Asn

<210> SEQ ID NO 31
<211> LENGTH: 404
<212> TYPE: PRT
<213> ORGANISM: Loktanella vestfoldensis
<220> FEATURE:
<221> NAME/KEY: mat_peptide
<222> LOCATION: (1)..(404)
<223> OTHER INFORMATION: Mutant creatine amidinohydrolase _Loktanella
      vestfoldensis A3V128 with C298A substitution

<400> SEQUENCE: 31

Met Asp Asp Met Leu His Val Met Glu Trp His Asn Gly Glu Lys Glu
1               5                   10                  15

Phe Ser Pro Phe Ser Asp Asn Glu Met Ala Arg Arg Gln Asn Glu Leu
                20                  25                  30

Arg Asp Trp Met Gly Lys Asn Asp Val Asp Ala Ser Leu Phe Thr Ser
            35                  40                  45

Tyr His Cys Ile Asn Tyr Tyr Ser Gly Trp Leu Tyr Cys Tyr Phe Gly
        50                  55                  60

Arg Lys Tyr Gly Met Val Ile Asp Gln Lys Asn Ala Thr Thr Ile Ser

```
            65                  70                  75                  80
Ala Gly Ile Asp Gly Gly Gln Pro Phe Arg Arg Ser Phe Gly Asn Asn
                85                  90                  95

Ile Thr Tyr Thr Asp Trp Arg Arg Asp Asn Phe Tyr Arg Ala Ile Gln
            100                 105                 110

Gln Leu Thr Pro Gly Ala Lys Arg Ile Gly Ile Glu Phe Asp His Val
            115                 120                 125

Ser Leu Glu Tyr Arg Gln Leu Leu Gln Asp Ala Leu Pro Gly Val Glu
            130                 135                 140

Phe Val Asp Val Gly Gln Pro Ala Met Trp Met Arg Thr Ile Lys Ser
145                 150                 155                 160

Ala Glu Glu Ile Lys Leu Ile Lys Glu Gly Ala Arg Val Ala Asp Val
                165                 170                 175

Gly Gly Ala Ala Val Ala Ala Val Lys Ala Gly Val Pro Glu His
                180                 185                 190

Glu Val Ala Ile Ala Ser Thr Asn Ala Met Ile Arg Glu Ile Ala Asn
                195                 200                 205

Ser Phe Pro Phe Val Glu Leu Met Asp Thr Trp Thr Trp Phe Gln Ser
            210                 215                 220

Gly Ile Asn Thr Asp Gly Ala His Asn Pro Val Thr Asn Lys Lys Val
225                 230                 235                 240

Gln Ser Gly Glu Ile Leu Ser Leu Asn Thr Phe Pro Met Ile Phe Gly
                245                 250                 255

Tyr Tyr Thr Ala Leu Glu Arg Thr Leu Phe Cys Asp His Val Asp Asp
                260                 265                 270

Ala Ser Leu Asp Ile Trp Glu Lys Asn Val Lys Val His Glu Arg Gly
            275                 280                 285

Leu Glu Leu Ile Lys Pro Gly Ala Arg Ala Met Asp Ile Ala Ile Glu
            290                 295                 300

Leu Asn Glu Met Tyr Arg Glu Trp Asp Leu Leu Lys Tyr Arg Ser Phe
305                 310                 315                 320

Gly Tyr Gly His Ser Phe Gly Val Leu Ser His Tyr Tyr Gly Arg Glu
                325                 330                 335

Ala Gly Val Glu Leu Arg Glu Asp Ile Glu Thr Glu Leu Lys Pro Gly
                340                 345                 350

Met Val Val Ser Met Glu Pro Met Val Met Ile Pro Glu Gly Gln Pro
            355                 360                 365

Gly Ala Gly Gly Tyr Arg Glu His Asp Ile Leu Val Ile Gly Glu Asp
            370                 375                 380

Asn Thr Val Glu Asn Ile Thr Gly Phe Pro Phe Gly Pro Glu His Asn
385                 390                 395                 400

Val Ile Lys Asn

<210> SEQ ID NO 32
<211> LENGTH: 404
<212> TYPE: PRT
<213> ORGANISM: Loktanella vestfoldensis
<220> FEATURE:
<221> NAME/KEY: mat_peptide
<222> LOCATION: (1)..(404)
<223> OTHER INFORMATION: Mutant creatine amidinohydrolase _Loktanella
      vestfoldensis A3V128 with C298A +C267L substitutions

<400> SEQUENCE: 32

Met Asp Asp Met Leu His Val Met Glu Trp His Asn Gly Glu Lys Glu
1               5                   10                  15
```

```
Phe Ser Pro Phe Ser Asp Asn Glu Met Ala Arg Arg Gln Asn Glu Leu
            20                  25                  30

Arg Asp Trp Met Gly Lys Asn Asp Val Asp Ala Ser Leu Phe Thr Ser
        35                  40                  45

Tyr His Cys Ile Asn Tyr Tyr Ser Gly Trp Leu Tyr Cys Tyr Phe Gly
    50                  55                  60

Arg Lys Tyr Gly Met Val Ile Asp Gln Lys Asn Ala Thr Thr Ile Ser
65                  70                  75                  80

Ala Gly Ile Asp Gly Gln Pro Phe Arg Arg Ser Phe Gly Asn Asn
                85                  90                  95

Ile Thr Tyr Thr Asp Trp Arg Arg Asp Asn Phe Tyr Arg Ala Ile Gln
                100                 105                 110

Gln Leu Thr Pro Gly Ala Lys Arg Ile Gly Ile Glu Phe Asp His Val
            115                 120                 125

Ser Leu Glu Tyr Arg Gln Leu Leu Gln Asp Ala Leu Pro Gly Val Glu
130                 135                 140

Phe Val Asp Val Gly Gln Pro Ala Met Trp Met Arg Thr Ile Lys Ser
145                 150                 155                 160

Ala Glu Glu Ile Lys Leu Ile Lys Glu Gly Ala Arg Val Ala Asp Val
                165                 170                 175

Gly Gly Ala Ala Val Ala Ala Val Lys Ala Gly Val Pro Glu His
            180                 185                 190

Glu Val Ala Ile Ala Ser Thr Asn Ala Met Ile Arg Glu Ile Ala Asn
            195                 200                 205

Ser Phe Pro Phe Val Glu Leu Met Asp Thr Trp Thr Trp Phe Gln Ser
210                 215                 220

Gly Ile Asn Thr Asp Gly Ala His Asn Pro Val Thr Asn Lys Lys Val
225                 230                 235                 240

Gln Ser Gly Glu Ile Leu Ser Leu Asn Thr Phe Pro Met Ile Phe Gly
                245                 250                 255

Tyr Tyr Thr Ala Leu Glu Arg Thr Leu Phe Leu Asp His Val Asp Asp
            260                 265                 270

Ala Ser Leu Asp Ile Trp Glu Lys Asn Val Lys Val His Glu Arg Gly
            275                 280                 285

Leu Glu Leu Ile Lys Pro Gly Ala Arg Ala Met Asp Ile Ala Ile Glu
290                 295                 300

Leu Asn Glu Met Tyr Arg Glu Trp Asp Leu Leu Lys Tyr Arg Ser Phe
305                 310                 315                 320

Gly Tyr Gly His Ser Phe Gly Val Leu Ser His Tyr Tyr Gly Arg Glu
                325                 330                 335

Ala Gly Val Glu Leu Arg Glu Asp Ile Glu Thr Glu Leu Lys Pro Gly
            340                 345                 350

Met Val Val Ser Met Glu Pro Met Val Met Ile Pro Glu Gly Gln Pro
            355                 360                 365

Gly Ala Gly Gly Tyr Arg Glu His Asp Ile Leu Val Ile Gly Glu Asp
            370                 375                 380

Asn Thr Val Glu Asn Ile Thr Gly Phe Pro Phe Gly Pro Glu His Asn
385                 390                 395                 400

Val Ile Lys Asn

<210> SEQ ID NO 33
<211> LENGTH: 1230
<212> TYPE: DNA
```

```
<213> ORGANISM: Lutibaculum baratangense
<220> FEATURE:
<221> NAME/KEY: CDS
<222> LOCATION: (1)..(1230)
<223> OTHER INFORMATION: ESR24399.1 Lutibaculum baratangense AMV1 gene
      encoding creatine amidinohydrolase [V4RGE5]

<400> SEQUENCE: 33 atg ctg gac aag acg atc ctc gac gac atg gtg cac gtc acg gag tgg      48
Met Leu Asp Lys Thr Ile Leu Asp Asp Met Val His Val Thr Glu Trp
1               5                   10                  15 cac aac ggc gaa aag gaa ttc ctg ccg ttc tcc gac gcc gag atg agc      96
His Asn Gly Glu Lys Glu Phe Leu Pro Phe Ser Asp Ala Glu Met Ser
            20                  25                  30 cgg cga cag gac gac gtg cgc agt tgg atg gga gcg aat aac gtc gat     144
Arg Arg Gln Asp Asp Val Arg Ser Trp Met Gly Ala Asn Asn Val Asp
        35                  40                  45 gcg gcg ctc ttc acc tcg tat cac tgc atc aac tac tat tcg ggc tgg     192
Ala Ala Leu Phe Thr Ser Tyr His Cys Ile Asn Tyr Tyr Ser Gly Trp
50                  55                  60 ctc tac tgc tat ttc ggc cgc agg tac ggc atg gtg atc acg ccc gac     240
Leu Tyr Cys Tyr Phe Gly Arg Arg Tyr Gly Met Val Ile Thr Pro Asp
65                  70                  75                  80 gcg gcc acg acc atc tcc gcc ggc atc gac ggc ggc cag ccc tgg cgg     288
Ala Ala Thr Thr Ile Ser Ala Gly Ile Asp Gly Gly Gln Pro Trp Arg
                85                  90                  95 cgg acc ttc ggc aac aac gtc acc tac acc gac tgg cgc cgc gac aac     336
Arg Thr Phe Gly Asn Asn Val Thr Tyr Thr Asp Trp Arg Arg Asp Asn
            100                 105                 110 tac tac cag gcg gtg agg cag ctc ctg ccg ggt gtc agg cgg ctg ggc     384
Tyr Tyr Gln Ala Val Arg Gln Leu Leu Pro Gly Val Arg Arg Leu Gly
        115                 120                 125 atc gaa ttc gac cac gtg tcg ctc gac ttc cgt cgg gac ctc gaa gcg     432
Ile Glu Phe Asp His Val Ser Leu Asp Phe Arg Arg Asp Leu Glu Ala
130                 135                 140 gcg ctg ccg ggg gtg gag ttc gtc gac gtg ggc cag ccc tcg atg tgg     480
Ala Leu Pro Gly Val Glu Phe Val Asp Val Gly Gln Pro Ser Met Trp
145                 150                 155                 160 atg cgc acc atc aag tcc gcg gag gag cag aag ctg atc cgc gaa ggc     528
Met Arg Thr Ile Lys Ser Ala Glu Glu Gln Lys Leu Ile Arg Glu Gly
                165                 170                 175 gcc cgc atc tgc gac atc ggc ggc gag gcg gtg gcg aag gcc gtg aag     576
Ala Arg Ile Cys Asp Ile Gly Gly Glu Ala Val Ala Lys Ala Val Lys
            180                 185                 190 gcc ggc gtc ccg gag cac gag gtg gcc atc gcc tcg acc aac gcg atg     624
Ala Gly Val Pro Glu His Glu Val Ala Ile Ala Ser Thr Asn Ala Met
        195                 200                 205 atc cgc gag atc gcc gag tcc ttt ccc tac gtc gag ctg atg gac acc     672
Ile Arg Glu Ile Ala Glu Ser Phe Pro Tyr Val Glu Leu Met Asp Thr
210                 215                 220 tgg acg tgg ttc cag tcc ggg atc aac acc gac ggc gcc cac aat ccg     720
Trp Thr Trp Phe Gln Ser Gly Ile Asn Thr Asp Gly Ala His Asn Pro
225                 230                 235                 240 gtc acg aac cgc gtg gtg cag tca ggc gac atc ctc tcg ctc aac tgc     768
Val Thr Asn Arg Val Val Gln Ser Gly Asp Ile Leu Ser Leu Asn Cys
                245                 250                 255 ttc ccc atg atc ttc ggc tat tac acc gcg ctc gag cgg acg atg ttc     816
Phe Pro Met Ile Phe Gly Tyr Tyr Thr Ala Leu Glu Arg Thr Met Phe
            260                 265                 270 tgc gac cac gtc gac gac gcg agc ctc gac gta tgg gag aag aac gtc     864
Cys Asp His Val Asp Asp Ala Ser Leu Asp Val Trp Glu Lys Asn Val
```

```
                275                 280                 285
gcg gtt cac cgg cgc ggg ctc gag ctg atc cgc ccc ggg aag aag tgc      912
Ala Val His Arg Arg Gly Leu Glu Leu Ile Arg Pro Gly Lys Lys Cys
290                 295                 300 ggg gag atc gcg cag gag ctg aac cag atg tac cgc gag tgg gat ctg      960
Gly Glu Ile Ala Gln Glu Leu Asn Gln Met Tyr Arg Glu Trp Asp Leu
305                 310                 315                 320 ctg cag tac cgc tcc ttc ggc tac ggc cac tca ttc ggg gtc ctc tcc     1008
Leu Gln Tyr Arg Ser Phe Gly Tyr Gly His Ser Phe Gly Val Leu Ser
                325                 330                 335 cac tac tac gga cgc gaa gcc ggg gtg gaa ctg cgg gag gac atc gac     1056
His Tyr Tyr Gly Arg Glu Ala Gly Val Glu Leu Arg Glu Asp Ile Asp
            340                 345                 350 acc gag ctc aag ccc ggc atg gtc gtg tcc atg gag ccg atg gtg atg     1104
Thr Glu Leu Lys Pro Gly Met Val Val Ser Met Glu Pro Met Val Met
        355                 360                 365 atc ccc gag ggg aag ccc ggc gcc ggt ggc tac cgg gag cac gac ata     1152
Ile Pro Glu Gly Lys Pro Gly Ala Gly Gly Tyr Arg Glu His Asp Ile
370                 375                 380 ctg atc gtc acc gag gat ggc gcg gag aac ata acc ggc ttc ccg ttc     1200
Leu Ile Val Thr Glu Asp Gly Ala Glu Asn Ile Thr Gly Phe Pro Phe
385                 390                 395                 400 ggg ccg gag cac aac gtg atc cgc aac tga                             1230
Gly Pro Glu His Asn Val Ile Arg Asn
                405
```

<210> SEQ ID NO 34
<211> LENGTH: 409
<212> TYPE: PRT
<213> ORGANISM: Lutibaculum baratangense

<400> SEQUENCE: 34

```
Met Leu Asp Lys Thr Ile Leu Asp Asp Met Val His Val Thr Glu Trp
1               5                   10                  15

His Asn Gly Glu Lys Glu Phe Leu Pro Phe Ser Asp Ala Glu Met Ser
                20                  25                  30

Arg Arg Gln Asp Asp Val Arg Ser Trp Met Gly Ala Asn Asn Val Asp
            35                  40                  45

Ala Ala Leu Phe Thr Ser Tyr His Cys Ile Asn Tyr Ser Gly Trp
        50                  55                  60

Leu Tyr Cys Tyr Phe Gly Arg Arg Tyr Gly Met Val Ile Thr Pro Asp
65                  70                  75                  80

Ala Ala Thr Thr Ile Ser Ala Gly Ile Asp Gly Gly Gln Pro Trp Arg
                85                  90                  95

Arg Thr Phe Gly Asn Asn Val Thr Tyr Thr Asp Trp Arg Arg Asp Asn
            100                 105                 110

Tyr Tyr Gln Ala Val Arg Gln Leu Leu Pro Gly Val Arg Arg Leu Gly
        115                 120                 125

Ile Glu Phe Asp His Val Ser Leu Asp Phe Arg Arg Asp Leu Glu Ala
    130                 135                 140

Ala Leu Pro Gly Val Glu Phe Val Asp Val Gly Gln Pro Ser Met Trp
145                 150                 155                 160

Met Arg Thr Ile Lys Ser Ala Glu Glu Gln Lys Leu Ile Arg Glu Gly
                165                 170                 175

Ala Arg Ile Cys Asp Ile Gly Gly Glu Ala Val Ala Lys Ala Val Lys
            180                 185                 190

Ala Gly Val Pro Glu His Glu Val Ala Ile Ala Ser Thr Asn Ala Met
```

```
            195                 200                 205
Ile Arg Glu Ile Ala Glu Ser Phe Pro Tyr Val Glu Leu Met Asp Thr
        210                 215                 220

Trp Thr Trp Phe Gln Ser Gly Ile Asn Thr Asp Gly Ala His Asn Pro
225                 230                 235                 240

Val Thr Asn Arg Val Val Gln Ser Gly Asp Ile Leu Ser Leu Asn Cys
                245                 250                 255

Phe Pro Met Ile Phe Gly Tyr Tyr Thr Ala Leu Glu Arg Thr Met Phe
            260                 265                 270

Cys Asp His Val Asp Asp Ala Ser Leu Asp Val Trp Glu Lys Asn Val
        275                 280                 285

Ala Val His Arg Arg Gly Leu Glu Leu Ile Arg Pro Gly Lys Lys Cys
    290                 295                 300

Gly Glu Ile Ala Gln Glu Leu Asn Gln Met Tyr Arg Glu Trp Asp Leu
305                 310                 315                 320

Leu Gln Tyr Arg Ser Phe Gly Tyr Gly His Ser Phe Gly Val Leu Ser
                325                 330                 335

His Tyr Tyr Gly Arg Glu Ala Gly Val Glu Leu Arg Glu Asp Ile Asp
            340                 345                 350

Thr Glu Leu Lys Pro Gly Met Val Val Ser Met Glu Pro Met Val Met
        355                 360                 365

Ile Pro Glu Gly Lys Pro Gly Ala Gly Tyr Arg Glu His Asp Ile
    370                 375                 380

Leu Ile Val Thr Glu Asp Gly Ala Glu Asn Ile Thr Gly Phe Pro Phe
385                 390                 395                 400

Gly Pro Glu His Asn Val Ile Arg Asn
                405

<210> SEQ ID NO 35
<211> LENGTH: 409
<212> TYPE: PRT
<213> ORGANISM: Lutibaculum baratangense
<220> FEATURE:
<221> NAME/KEY: mat_peptide
<222> LOCATION: (1)..(409)
<223> OTHER INFORMATION: Mutant creatine amidinohydrolase _Lutibaculum
      baratangense V4RGE5 with C180A+C304A  substitutions

<400> SEQUENCE: 35

Met Leu Asp Lys Thr Ile Leu Asp Asp Met Val His Val Thr Glu Trp
1               5                  10                  15

His Asn Gly Glu Lys Glu Phe Leu Pro Phe Ser Asp Ala Glu Met Ser
                20                  25                  30

Arg Arg Gln Asp Asp Val Arg Ser Trp Met Gly Ala Asn Asn Val Asp
            35                  40                  45

Ala Ala Leu Phe Thr Ser Tyr His Cys Ile Asn Tyr Tyr Ser Gly Trp
    50                  55                  60

Leu Tyr Cys Tyr Phe Gly Arg Arg Tyr Gly Met Val Ile Thr Pro Asp
65                  70                  75                  80

Ala Ala Thr Thr Ile Ser Ala Gly Ile Asp Gly Gly Gln Pro Trp Arg
                85                  90                  95

Arg Thr Phe Gly Asn Asn Val Thr Tyr Thr Asp Trp Arg Arg Asp Asn
            100                 105                 110

Tyr Tyr Gln Ala Val Arg Gln Leu Leu Pro Gly Val Arg Arg Leu Gly
        115                 120                 125

Ile Glu Phe Asp His Val Ser Leu Asp Phe Arg Arg Asp Leu Glu Ala
```

```
            130                 135                 140
Ala Leu Pro Gly Val Glu Phe Val Asp Val Gly Gln Pro Ser Met Trp
145                 150                 155                 160

Met Arg Thr Ile Lys Ser Ala Glu Glu Gln Lys Leu Ile Arg Glu Gly
                165                 170                 175

Ala Arg Ile Ala Asp Ile Gly Gly Glu Ala Val Ala Lys Ala Val Lys
            180                 185                 190

Ala Gly Val Pro Glu His Glu Val Ala Ile Ala Ser Thr Asn Ala Met
                195                 200                 205

Ile Arg Glu Ile Ala Glu Ser Phe Pro Tyr Val Glu Leu Met Asp Thr
            210                 215                 220

Trp Thr Trp Phe Gln Ser Gly Ile Asn Thr Asp Gly Ala His Asn Pro
225                 230                 235                 240

Val Thr Asn Arg Val Val Gln Ser Gly Asp Ile Leu Ser Leu Asn Cys
                245                 250                 255

Phe Pro Met Ile Phe Gly Tyr Tyr Thr Ala Leu Glu Arg Thr Met Phe
            260                 265                 270

Cys Asp His Val Asp Asp Ala Ser Leu Asp Val Trp Glu Lys Asn Val
            275                 280                 285

Ala Val His Arg Arg Gly Leu Glu Leu Ile Arg Pro Gly Lys Lys Ala
            290                 295                 300

Gly Glu Ile Ala Gln Glu Leu Asn Gln Met Tyr Arg Glu Trp Asp Leu
305                 310                 315                 320

Leu Gln Tyr Arg Ser Phe Gly Tyr Gly His Ser Phe Gly Val Leu Ser
                325                 330                 335

His Tyr Tyr Gly Arg Glu Ala Gly Val Glu Leu Arg Glu Asp Ile Asp
            340                 345                 350

Thr Glu Leu Lys Pro Gly Met Val Val Ser Met Glu Pro Met Val Met
            355                 360                 365

Ile Pro Glu Gly Lys Pro Gly Ala Gly Tyr Arg Glu His Asp Ile
            370                 375                 380

Leu Ile Val Thr Glu Asp Gly Ala Glu Asn Ile Thr Gly Phe Pro Phe
385                 390                 395                 400

Gly Pro Glu His Asn Val Ile Arg Asn
                405

<210> SEQ ID NO 36
<211> LENGTH: 409
<212> TYPE: PRT
<213> ORGANISM: Lutibaculum baratangense
<220> FEATURE:
<221> NAME/KEY: mat_peptide
<222> LOCATION: (1)..(409)
<223> OTHER INFORMATION: Mutant creatine amidinohydrolase _Lutibaculum
      baratangense V4RGE5 with C180A+C304A+C273L substitutions

<400> SEQUENCE: 36

Met Leu Asp Lys Thr Ile Leu Asp Asp Met Val His Val Thr Glu Trp
1               5                   10                  15

His Asn Gly Glu Lys Glu Phe Leu Pro Phe Ser Asp Ala Glu Met Ser
                20                  25                  30

Arg Arg Gln Asp Asp Val Arg Ser Trp Met Gly Ala Asn Asn Val Asp
            35                  40                  45

Ala Ala Leu Phe Thr Ser Tyr His Cys Ile Asn Tyr Tyr Ser Gly Trp
50                  55                  60

Leu Tyr Cys Tyr Phe Gly Arg Arg Tyr Gly Met Val Ile Thr Pro Asp
```

```
             65                  70                  75                  80
    Ala Ala Thr Thr Ile Ser Ala Gly Ile Asp Gly Gly Gln Pro Trp Arg
                        85                  90                  95

Arg Thr Phe Gly Asn Asn Val Thr Tyr Thr Asp Trp Arg Arg Asp Asn
                       100                 105                 110

Tyr Tyr Gln Ala Val Arg Gln Leu Leu Pro Gly Val Arg Arg Leu Gly
                       115                 120                 125

Ile Glu Phe Asp His Val Ser Leu Asp Phe Arg Arg Asp Leu Glu Ala
                130                 135                 140

Ala Leu Pro Gly Val Glu Phe Val Asp Val Gly Gln Pro Ser Met Trp
    145                 150                 155                 160

Met Arg Thr Ile Lys Ser Ala Glu Glu Gln Lys Leu Ile Arg Glu Gly
                        165                 170                 175

Ala Arg Ile Ala Asp Ile Gly Gly Glu Ala Val Ala Lys Ala Val Lys
                        180                 185                 190

Ala Gly Val Pro Glu His Glu Val Ala Ile Ala Ser Thr Asn Ala Met
                        195                 200                 205

Ile Arg Glu Ile Ala Glu Ser Phe Pro Tyr Val Glu Leu Met Asp Thr
                210                 215                 220

Trp Thr Trp Phe Gln Ser Gly Ile Asn Thr Asp Gly Ala His Asn Pro
    225                 230                 235                 240

Val Thr Asn Arg Val Val Gln Ser Gly Asp Ile Leu Ser Leu Asn Cys
                        245                 250                 255

Phe Pro Met Ile Phe Gly Tyr Tyr Thr Ala Leu Glu Arg Thr Met Phe
                        260                 265                 270

Leu Asp His Val Asp Asp Ala Ser Leu Asp Val Trp Glu Lys Asn Val
                275                 280                 285

Ala Val His Arg Arg Gly Leu Glu Leu Ile Arg Pro Gly Lys Lys Ala
                290                 295                 300

Gly Glu Ile Ala Gln Glu Leu Asn Gln Met Tyr Arg Glu Trp Asp Leu
    305                 310                 315                 320

Leu Gln Tyr Arg Ser Phe Gly Tyr Gly His Ser Phe Gly Val Leu Ser
                        325                 330                 335

His Tyr Tyr Gly Arg Glu Ala Gly Val Glu Leu Arg Glu Asp Ile Asp
                        340                 345                 350

Thr Glu Leu Lys Pro Gly Met Val Val Ser Met Glu Pro Met Val Met
                        355                 360                 365

Ile Pro Glu Gly Lys Pro Gly Ala Gly Gly Tyr Arg Glu His Asp Ile
                370                 375                 380

Leu Ile Val Thr Glu Asp Gly Ala Glu Asn Ile Thr Gly Phe Pro Phe
    385                 390                 395                 400

Gly Pro Glu His Asn Val Ile Arg Asn
                        405

<210> SEQ ID NO 37
<211> LENGTH: 1218
<212> TYPE: DNA
<213> ORGANISM: Roseobacter sp
<220> FEATURE:
<221> NAME/KEY: CDS
<222> LOCATION: (1)..(1218)
<223> OTHER INFORMATION: EDM71125.1 Roseobacter sp. AzwK-3b gene
      encoding creatine amidinohydrolase [A6FQQ7]

<400> SEQUENCE: 37 atg ctt gac gac atg ctc cac gtg acc gaa tgg cac aat gga gaa aag     48
```

```
Met Leu Asp Asp Met Leu His Val Thr Glu Trp His Asn Gly Glu Lys
1               5                   10                  15 gaa ttt tcg cct ttt tcc gac aac gaa atg gcg cgc agg cag aat gaa      96
Glu Phe Ser Pro Phe Ser Asp Asn Glu Met Ala Arg Arg Gln Asn Glu
            20                  25                  30 ctg cgc gac tgg atg gcc aag aac gac gtc gat gcg gtg ctg ctc acg      144
Leu Arg Asp Trp Met Ala Lys Asn Asp Val Asp Ala Val Leu Leu Thr
        35                  40                  45 tct tat cac tgc att aca tat tac tca ggc tgg ctg tat tgc tat ttc      192
Ser Tyr His Cys Ile Thr Tyr Tyr Ser Gly Trp Leu Tyr Cys Tyr Phe
    50                  55                  60 ggt cgc aaa tac gga atg gtg atc gac cag aag act gcc acc acc gtt      240
Gly Arg Lys Tyr Gly Met Val Ile Asp Gln Lys Thr Ala Thr Thr Val
65                  70                  75                  80 tcg gcg ggc atc gat ggc ggt caa ccc tgg cgc cgg agc ttt ggc aac      288
Ser Ala Gly Ile Asp Gly Gly Gln Pro Trp Arg Arg Ser Phe Gly Asn
                85                  90                  95 aac gtc acc tat acc gat tgg cgg cgc gac aat ttc tat cgt gca gtg      336
Asn Val Thr Tyr Thr Asp Trp Arg Arg Asp Asn Phe Tyr Arg Ala Val
            100                 105                 110 cag ggg ctt acc cag ggc gcg cgg cgt gtg ggc atc gag ttc gac cat      384
Gln Gly Leu Thr Gln Gly Ala Arg Arg Val Gly Ile Glu Phe Asp His
        115                 120                 125 gtc tcg ctg gaa tat cgc gat ctg ttg cag gat gcg ctg ccg ggt gtg      432
Val Ser Leu Glu Tyr Arg Asp Leu Leu Gln Asp Ala Leu Pro Gly Val
    130                 135                 140 gac ttc gtc gat gtc agc cag ccg tcg atg tgg atg cgc acg atc aaa      480
Asp Phe Val Asp Val Ser Gln Pro Ser Met Trp Met Arg Thr Ile Lys
145                 150                 155                 160 tca gac gag gag atc aag ctg atc cgc gaa ggc gca cgg gtg gcg gat      528
Ser Asp Glu Glu Ile Lys Leu Ile Arg Glu Gly Ala Arg Val Ala Asp
                165                 170                 175 gtc ggc ggt tat gcc gtg gcc gcc gcc gtg caa gcg ggc gtg ccg gag      576
Val Gly Gly Tyr Ala Val Ala Ala Ala Val Gln Ala Gly Val Pro Glu
            180                 185                 190 cat gag gtc gcc atc gcg ggc acc aat gcg atg atc cgc gag atc gcc      624
His Glu Val Ala Ile Ala Gly Thr Asn Ala Met Ile Arg Glu Ile Ala
        195                 200                 205 aaa tcc ttc ccc ttt gtc gag ttg atg gac acc tgg acc tgg ttc cag      672
Lys Ser Phe Pro Phe Val Glu Leu Met Asp Thr Trp Thr Trp Phe Gln
    210                 215                 220 tca ggt atc aat acc gac ggt gcg cat aac ccg gtg acg aac cgc gtg      720
Ser Gly Ile Asn Thr Asp Gly Ala His Asn Pro Val Thr Asn Arg Val
225                 230                 235                 240 gtg caa tcg ggc gat atc ctc agc ctc aac acc ttt ccg atg atc ttc      768
Val Gln Ser Gly Asp Ile Leu Ser Leu Asn Thr Phe Pro Met Ile Phe
                245                 250                 255 ggc tat tac acc gcg ctg gag cgc acg ctg ttt tgc gac tcg gtg gat      816
Gly Tyr Tyr Thr Ala Leu Glu Arg Thr Leu Phe Cys Asp Ser Val Asp
            260                 265                 270 gat gcg agc ttg gat gtc tgg gaa aag aac gtg gca gtg cat cgt cgc      864
Asp Ala Ser Leu Asp Val Trp Glu Lys Asn Val Ala Val His Arg Arg
        275                 280                 285 gga ctc gag ctt atg aag ccg ggt gcg cgc tgc atg gat atc gcg atc      912
Gly Leu Glu Leu Met Lys Pro Gly Ala Arg Cys Met Asp Ile Ala Ile
    290                 295                 300 gaa ctg aac gag atg tat cgc gaa tgg gac ctg ctg aaa tac cgc tcg      960
Glu Leu Asn Glu Met Tyr Arg Glu Trp Asp Leu Leu Lys Tyr Arg Ser
305                 310                 315                 320
```

```
ttc ggc tat ggc cac agc ttt ggc gtg ctc agt cac tat tac ggg cgc      1008
Phe Gly Tyr Gly His Ser Phe Gly Val Leu Ser His Tyr Tyr Gly Arg
                325                 330                 335 gag gcc ggg gtc gaa ctg cgc gag gat atc gac acg gtg ctc aag ccc      1056
Glu Ala Gly Val Glu Leu Arg Glu Asp Ile Asp Thr Val Leu Lys Pro
            340                 345                 350 ggc atg gtc gtg tcc atg gag ccg atg gtc atg atc ccc gaa ggg gcg      1104
Gly Met Val Val Ser Met Glu Pro Met Val Met Ile Pro Glu Gly Ala
        355                 360                 365 ccc ggt gcg ggc ggc tac cgc gag cat gat atc ctc gtg atc ggc gag      1152
Pro Gly Ala Gly Gly Tyr Arg Glu His Asp Ile Leu Val Ile Gly Glu
    370                 375                 380 gat ggg gcg gag aac atc acc ggg ttt ccc ttc ggc ccc gag cac aac      1200
Asp Gly Ala Glu Asn Ile Thr Gly Phe Pro Phe Gly Pro Glu His Asn
385                 390                 395                 400 atc gtc ggc tcc aac tga                                              1218
Ile Val Gly Ser Asn
                405

<210> SEQ ID NO 38
<211> LENGTH: 405
<212> TYPE: PRT
<213> ORGANISM: Roseobacter sp

<400> SEQUENCE: 38

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Asp Trp Met Ala Lys Asn Asp Val Asp Ala Val Leu Leu Thr
        35                  40                  45

Ser Tyr His Cys Ile Thr Tyr Tyr Ser Gly Trp Leu Tyr Cys Tyr Phe
    50                  55                  60

Gly Arg Lys Tyr Gly Met Val Ile Asp Gln Lys Thr Ala Thr Thr Val
65                  70                  75                  80

Ser Ala Gly Ile Asp Gly Gly Gln Pro Trp Arg Arg Ser Phe Gly Asn
            85                  90                  95

Asn Val Thr Tyr Thr Asp Trp Arg Arg Asp Asn Phe Tyr Arg Ala Val
            100                 105                 110

Gln Gly Leu Thr Gln Gly Ala Arg Arg Val Gly Ile Glu Phe Asp His
        115                 120                 125

Val Ser Leu Glu Tyr Arg Asp Leu Leu Gln Asp Ala Leu Pro Gly Val
    130                 135                 140

Asp Phe Val Asp Val Ser Gln Pro Ser Met Trp Met Arg Thr Ile Lys
145                 150                 155                 160

Ser Asp Glu Glu Ile Lys Leu Ile Arg Glu Gly Ala Arg Val Ala Asp
            165                 170                 175

Val Gly Gly Tyr Ala Val Ala Ala Val Gln Ala Gly Val Pro Glu
        180                 185                 190

His Glu Val Ala Ile Ala Gly Thr Asn Ala Met Ile Arg Glu Ile Ala
    195                 200                 205

Lys Ser Phe Pro Phe Val Glu Leu Met Asp Thr Trp Thr Trp Phe Gln
210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
            245                 250                 255
```

```
Gly Tyr Tyr Thr Ala Leu Glu Arg Thr Leu Phe Cys Asp Ser Val Asp
            260                 265                 270

Asp Ala Ser Leu Asp Val Trp Glu Lys Asn Val Ala Val His Arg Arg
        275                 280                 285

Gly Leu Glu Leu Met Lys Pro Gly Ala Arg Cys Met Asp Ile Ala Ile
    290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Ala
        355                 360                 365

Pro Gly Ala Gly Gly Tyr Arg Glu His Asp Ile Leu Val Ile Gly Glu
    370                 375                 380

Asp Gly Ala Glu Asn Ile Thr Gly Phe Pro Phe Gly Pro Glu His Asn
385                 390                 395                 400

Ile Val Gly Ser Asn
                405

<210> SEQ ID NO 39
<211> LENGTH: 405
<212> TYPE: PRT
<213> ORGANISM: Roseobacter sp
<220> FEATURE:
<221> NAME/KEY: mat_peptide
<222> LOCATION: (1)..(405)
<223> OTHER INFORMATION: Mutant creatine amidinohydrolase Roseobacter
      sp. _A6FQQ7 with C299A substitution

<400> SEQUENCE: 39

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Asp Trp Met Ala Lys Asn Asp Val Asp Ala Val Leu Leu Thr
        35                  40                  45

Ser Tyr His Cys Ile Thr Tyr Tyr Ser Gly Trp Leu Tyr Cys Tyr Phe
    50                  55                  60

Gly Arg Lys Tyr Gly Met Val Ile Asp Gln Lys Thr Ala Thr Thr Val
65                  70                  75                  80

Ser Ala Gly Ile Asp Gly Gly Gln Pro Trp Arg Arg Ser Phe Gly Asn
                85                  90                  95

Asn Val Thr Tyr Thr Asp Trp Arg Arg Asp Asn Phe Tyr Arg Ala Val
            100                 105                 110

Gln Gly Leu Thr Gln Gly Ala Arg Arg Val Gly Ile Glu Phe Asp His
        115                 120                 125

Val Ser Leu Glu Tyr Arg Asp Leu Leu Gln Asp Ala Leu Pro Gly Val
    130                 135                 140

Asp Phe Val Asp Val Ser Gln Pro Ser Met Trp Met Arg Thr Ile Lys
145                 150                 155                 160

Ser Asp Glu Glu Ile Lys Leu Ile Arg Glu Gly Ala Arg Val Ala Asp
                165                 170                 175

Val Gly Gly Tyr Ala Val Ala Ala Val Gln Ala Gly Val Pro Glu
            180                 185                 190
```

-continued

His Glu Val Ala Ile Ala Gly Thr Asn Ala Met Ile Arg Glu Ile Ala
                195                 200                 205

Lys Ser Phe Pro Phe Val Glu Leu Met Asp Thr Trp Thr Trp Phe Gln
            210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp Ser Val Asp
            260                 265                 270

Asp Ala Ser Leu Asp Val Trp Glu Lys Asn Val Ala Val His Arg Arg
            275                 280                 285

Gly Leu Glu Leu Met Lys Pro Gly Ala Arg Ala Met Asp Ile Ala Ile
            290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Ala
            355                 360                 365

Pro Gly Ala Gly Gly Tyr Arg Glu His Asp Ile Leu Val Ile Gly Glu
            370                 375                 380

Asp Gly Ala Glu Asn Ile Thr Gly Phe Pro Phe Gly Pro Glu His Asn
385                 390                 395                 400

Ile Val Gly Ser Asn
                405

<210> SEQ ID NO 40
<211> LENGTH: 405
<212> TYPE: PRT
<213> ORGANISM: Roseobacter sp.
<220> FEATURE:
<221> NAME/KEY: mat_peptide
<222> LOCATION: (1)..(405)
<223> OTHER INFORMATION: Mutant creatine amidinohydrolase Roseobacter
      sp._A6FQQ7 with C299A+ C268L substitution

<400> SEQUENCE: 40

Met Leu Asp Asp Met Leu His Val Thr Glu Trp His Asn Gly Glu Lys
1               5                   10                  15

Glu Phe Ser Pro Phe Ser Asp Asn Glu Met Ala Arg Arg Gln Asn Glu
            20                  25                  30

Leu Arg Asp Trp Met Ala Lys Asn Asp Val Asp Ala Val Leu Leu Thr
        35                  40                  45

Ser Tyr His Cys Ile Thr Tyr Tyr Ser Gly Trp Leu Tyr Cys Tyr Phe
    50                  55                  60

Gly Arg Lys Tyr Gly Met Val Ile Asp Gln Lys Thr Ala Thr Thr Val
65                  70                  75                  80

Ser Ala Gly Ile Asp Gly Gly Gln Pro Trp Arg Arg Ser Phe Gly Asn
                85                  90                  95

Asn Val Thr Tyr Thr Asp Trp Arg Arg Asp Asn Phe Tyr Arg Ala Val
            100                 105                 110

Gln Gly Leu Thr Gln Gly Ala Arg Arg Val Gly Ile Glu Phe Asp His
        115                 120                 125

```
Val Ser Leu Glu Tyr Arg Asp Leu Leu Gln Asp Ala Leu Pro Gly Val
    130                 135                 140

Asp Phe Val Asp Val Ser Gln Pro Ser Met Trp Met Arg Thr Ile Lys
145                 150                 155                 160

Ser Asp Glu Glu Ile Lys Leu Ile Arg Glu Gly Ala Arg Val Ala Asp
                165                 170                 175

Val Gly Gly Tyr Ala Val Ala Ala Ala Val Gln Ala Gly Val Pro Glu
            180                 185                 190

His Glu Val Ala Ile Ala Gly Thr Asn Ala Met Ile Arg Glu Ile Ala
        195                 200                 205

Lys Ser Phe Pro Phe Val Glu Leu Met Asp Thr Trp Thr Trp Phe Gln
    210                 215                 220

Ser Gly Ile Asn Thr Asp Gly Ala His Asn Pro Val Thr Asn Arg Val
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Leu Asp Ser Val Asp
            260                 265                 270

Asp Ala Ser Leu Asp Val Trp Glu Lys Asn Val Ala Val His Arg Arg
        275                 280                 285

Gly Leu Glu Leu Met Lys Pro Gly Ala Arg Ala Met Asp Ile Ala Ile
    290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Ser His Tyr Tyr Gly Arg
                325                 330                 335

Glu Ala Gly Val Glu Leu Arg Glu Asp Ile Asp Thr Val Leu Lys Pro
            340                 345                 350

Gly Met Val Val Ser Met Glu Pro Met Val Met Ile Pro Glu Gly Ala
        355                 360                 365

Pro Gly Ala Gly Gly Tyr Arg Glu His Asp Ile Leu Val Ile Gly Glu
    370                 375                 380

Asp Gly Ala Glu Asn Ile Thr Gly Phe Pro Phe Gly Pro Glu His Asn
385                 390                 395                 400

Ile Val Gly Ser Asn
                405

<210> SEQ ID NO 41
<211> LENGTH: 1233
<212> TYPE: DNA
<213> ORGANISM: Dinoroseobacter shibae
<220> FEATURE:
<221> NAME/KEY: CDS
<222> LOCATION: (1)..(1233)
<223> OTHER INFORMATION: ABV93862.1 Dinoroseobacter shibae DSM 16493
      gene encoding creatine amidinohydrolase [A8LQJ5]

<400> SEQUENCE: 41 atg gac ggt aat acc aac gtc gac gac atg ctc cac gtc atg gaa tgg      48
Met Asp Gly Asn Thr Asn Val Asp Asp Met Leu His Val Met Glu Trp
1               5                   10                  15 cat aac ggc gaa aaa gag ttc tcg ccc ttt tcg gac acc gag atg gcc      96
His Asn Gly Glu Lys Glu Phe Ser Pro Phe Ser Asp Thr Glu Met Ala
                20                  25                  30 cgt cgg caa aac gaa ttg cgc gac tgg atg gcc aag aac gat gtc gat     144
Arg Arg Gln Asn Glu Leu Arg Asp Trp Met Ala Lys Asn Asp Val Asp
            35                  40                  45
```

```
gcg tcg ctc ttc acc tcg tat cac tgc atc aac tat tac agc ggc tgg    192
Ala Ser Leu Phe Thr Ser Tyr His Cys Ile Asn Tyr Tyr Ser Gly Trp
 50              55                  60 ctg tat tgc tat ttc ggc cgt aaa tac ggc atg gtc atc gac cag aag    240
Leu Tyr Cys Tyr Phe Gly Arg Lys Tyr Gly Met Val Ile Asp Gln Lys
 65              70                  75                  80 aac gcc acg acg atc tcc gcc ggg atc gat ggc ggc cag ccc ttc cgc    288
Asn Ala Thr Thr Ile Ser Ala Gly Ile Asp Gly Gly Gln Pro Phe Arg
                 85                  90                  95 cgg agc ttt ggc aac aac atc acc tac acc gac tgg cgc cgc gac aac    336
Arg Ser Phe Gly Asn Asn Ile Thr Tyr Thr Asp Trp Arg Arg Asp Asn
            100                 105                 110 ttt tat cgc gcg atc cag cag ctg acc ccg ggc gcc aag cgc atc ggc    384
Phe Tyr Arg Ala Ile Gln Gln Leu Thr Pro Gly Ala Lys Arg Ile Gly
        115                 120                 125 atc gag ttc gac cat gtc tcg ctc gag tac cgc cag ctg ctg cag gat    432
Ile Glu Phe Asp His Val Ser Leu Glu Tyr Arg Gln Leu Leu Gln Asp
130                 135                 140 gcg ctg ccg ggc gtc gag ttc gtc gat gtc ggc cag ccc gcc atg tgg    480
Ala Leu Pro Gly Val Glu Phe Val Asp Val Gly Gln Pro Ala Met Trp
145                 150                 155                 160 atg cgc acc atc aag tcc gcc gaa gag atc aag ctg atc aag gaa ggc    528
Met Arg Thr Ile Lys Ser Ala Glu Glu Ile Lys Leu Ile Lys Glu Gly
                165                 170                 175 gcg cgc gtc gcc gac gtg ggt ggc gcg gcc gtg gcc gca gcg gtc aag    576
Ala Arg Val Ala Asp Val Gly Gly Ala Ala Val Ala Ala Ala Val Lys
            180                 185                 190 gcc ggt gtc ccc gag cat gaa gtg gcc atc gcc ggc acc acc gcg atg    624
Ala Gly Val Pro Glu His Glu Val Ala Ile Ala Gly Thr Thr Ala Met
        195                 200                 205 atc cgc gag atc gcg aac tcc ttc ccc ttc gtc gag ctg atg gac acc    672
Ile Arg Glu Ile Ala Asn Ser Phe Pro Phe Val Glu Leu Met Asp Thr
210                 215                 220 tgg acc tgg ttc cag tcc ggc atc aac acc gac ggc gcc cat aac ccg    720
Trp Thr Trp Phe Gln Ser Gly Ile Asn Thr Asp Gly Ala His Asn Pro
225                 230                 235                 240 gtg acc aac aag aag gtg cag tcg ggc gag atc ctc agc ctc aac acc    768
Val Thr Asn Lys Lys Val Gln Ser Gly Glu Ile Leu Ser Leu Asn Thr
                245                 250                 255 ttc ccg atg atc ttc ggc tat tac acc gcg ctg gaa cgg acc ctg ttc    816
Phe Pro Met Ile Phe Gly Tyr Tyr Thr Ala Leu Glu Arg Thr Leu Phe
            260                 265                 270 tgt gac cat gtg gac gat gcc agc ctc gac atc tgg gaa aag aac gtg    864
Cys Asp His Val Asp Asp Ala Ser Leu Asp Ile Trp Glu Lys Asn Val
        275                 280                 285 aag gtg cac gag cgt ggc ctg cag ctg atc aag ccc ggc gcg cgc tgc    912
Lys Val His Glu Arg Gly Leu Gln Leu Ile Lys Pro Gly Ala Arg Cys
290                 295                 300 atg gac atc gcg atc gag ctc aac gag atg tat cgc gag tgg gac ctg    960
Met Asp Ile Ala Ile Glu Leu Asn Glu Met Tyr Arg Glu Trp Asp Leu
305                 310                 315                 320 ctg aag tat cgc tcc ttc ggc tac ggg cac agc ttc ggt gtg ctg agc   1008
Leu Lys Tyr Arg Ser Phe Gly Tyr Gly His Ser Phe Gly Val Leu Ser
                325                 330                 335 cac tac tac ggc cgc gag gcg ggc gtc gag ctc cgc gag gat atc gaa   1056
His Tyr Tyr Gly Arg Glu Ala Gly Val Glu Leu Arg Glu Asp Ile Glu
            340                 345                 350 acc gag ctg aag cca ggg atg gtg gtg tcc atg gag ccg atg gtg atg   1104
Thr Glu Leu Lys Pro Gly Met Val Val Ser Met Glu Pro Met Val Met
```

```
                    355                 360                 365
atc ccc gag ggt cag ccg ggg gcc ggg ggc tac cgc gag cat gac atc    1152
Ile Pro Glu Gly Gln Pro Gly Ala Gly Gly Tyr Arg Glu His Asp Ile
370                 375                 380 ctg gtc atc aac gac gac aac acg gtg gaa aac atc acc ggg ttc ccc    1200
Leu Val Ile Asn Asp Asp Asn Thr Val Glu Asn Ile Thr Gly Phe Pro
385                 390                 395                 400 ttc ggc ccc gag cac aac atc atc aag aac tga                        1233
Phe Gly Pro Glu His Asn Ile Ile Lys Asn
                405                 410

<210> SEQ ID NO 42
<211> LENGTH: 410
<212> TYPE: PRT
<213> ORGANISM: Dinoroseobacter shibae

<400> SEQUENCE: 42

Met Asp Gly Asn Thr Asn Val Asp Asp Met Leu His Val Met Glu Trp
1               5                   10                  15

His Asn Gly Glu Lys Glu Phe Ser Pro Phe Ser Asp Thr Glu Met Ala
            20                  25                  30

Arg Arg Gln Asn Glu Leu Arg Asp Trp Met Ala Lys Asn Asp Val Asp
        35                  40                  45

Ala Ser Leu Phe Thr Ser Tyr His Cys Ile Asn Tyr Tyr Ser Gly Trp
    50                  55                  60

Leu Tyr Cys Tyr Phe Gly Arg Lys Tyr Gly Met Val Ile Asp Gln Lys
65                  70                  75                  80

Asn Ala Thr Thr Ile Ser Ala Gly Ile Asp Gly Gly Gln Pro Phe Arg
                85                  90                  95

Arg Ser Phe Gly Asn Asn Ile Thr Tyr Thr Asp Trp Arg Arg Asp Asn
            100                 105                 110

Phe Tyr Arg Ala Ile Gln Gln Leu Thr Pro Gly Ala Lys Arg Ile Gly
        115                 120                 125

Ile Glu Phe Asp His Val Ser Leu Glu Tyr Arg Gln Leu Leu Gln Asp
    130                 135                 140

Ala Leu Pro Gly Val Glu Phe Val Asp Val Gly Gln Pro Ala Met Trp
145                 150                 155                 160

Met Arg Thr Ile Lys Ser Ala Glu Glu Ile Lys Leu Ile Lys Glu Gly
                165                 170                 175

Ala Arg Val Ala Asp Val Gly Gly Ala Ala Val Ala Ala Ala Val Lys
            180                 185                 190

Ala Gly Val Pro Glu His Glu Val Ala Ile Ala Gly Thr Thr Ala Met
        195                 200                 205

Ile Arg Glu Ile Ala Asn Ser Phe Pro Phe Val Glu Leu Met Asp Thr
    210                 215                 220

Trp Thr Trp Phe Gln Ser Gly Ile Asn Thr Asp Gly Ala His Asn Pro
225                 230                 235                 240

Val Thr Asn Lys Lys Val Gln Ser Gly Glu Ile Leu Ser Leu Asn Thr
                245                 250                 255

Phe Pro Met Ile Phe Gly Tyr Tyr Thr Ala Leu Glu Arg Thr Leu Phe
            260                 265                 270

Cys Asp His Val Asp Asp Ala Ser Leu Asp Ile Trp Glu Lys Asn Val
        275                 280                 285

Lys Val His Glu Arg Gly Leu Gln Leu Ile Lys Pro Gly Ala Arg Cys
    290                 295                 300
```

```
Met Asp Ile Ala Ile Glu Leu Asn Glu Met Tyr Arg Glu Trp Asp Leu
305                 310                 315                 320

Leu Lys Tyr Arg Ser Phe Gly Tyr Gly His Ser Phe Gly Val Leu Ser
            325                 330                 335

His Tyr Tyr Gly Arg Glu Ala Gly Val Glu Leu Arg Gly Asp Ile Glu
                340                 345                 350

Thr Glu Leu Lys Pro Gly Met Val Ser Met Glu Pro Met Val Met
            355                 360                 365

Ile Pro Glu Gly Gln Pro Gly Ala Gly Tyr Arg Glu His Asp Ile
    370                 375                 380

Leu Val Ile Asn Asp Asn Thr Val Glu Asn Ile Thr Gly Phe Pro
385                 390                 395                 400

Phe Gly Pro Glu His Asn Ile Ile Lys Asn
                405                 410

<210> SEQ ID NO 43
<211> LENGTH: 410
<212> TYPE: PRT
<213> ORGANISM: Dinoroseobacter shibae
<220> FEATURE:
<221> NAME/KEY: mat_peptide
<222> LOCATION: (1)..(410)
<223> OTHER INFORMATION: Mutant creatine amidinohydrolase Roseobacter
      sp. _A8LQJ5 with C304A substitution

<400> SEQUENCE: 43

Met Asp Gly Asn Thr Asn Val Asp Asp Met Leu His Val Met Glu Trp
1               5                   10                  15

His Asn Gly Glu Lys Glu Phe Ser Pro Phe Ser Asp Thr Glu Met Ala
            20                  25                  30

Arg Arg Gln Asn Glu Leu Arg Asp Trp Met Ala Lys Asn Asp Val Asp
        35                  40                  45

Ala Ser Leu Phe Thr Ser Tyr His Cys Ile Asn Tyr Tyr Ser Gly Trp
    50                  55                  60

Leu Tyr Cys Tyr Phe Gly Arg Lys Tyr Gly Met Val Ile Asp Gln Lys
65                  70                  75                  80

Asn Ala Thr Thr Ile Ser Ala Gly Ile Asp Gly Gly Gln Pro Phe Arg
            85                  90                  95

Arg Ser Phe Gly Asn Asn Ile Thr Tyr Thr Asp Trp Arg Arg Asp Asn
        100                 105                 110

Phe Tyr Arg Ala Ile Gln Gln Leu Thr Pro Gly Ala Lys Arg Ile Gly
    115                 120                 125

Ile Glu Phe Asp His Val Ser Leu Glu Tyr Arg Gln Leu Leu Gln Asp
130                 135                 140

Ala Leu Pro Gly Val Glu Phe Val Asp Val Gly Gln Pro Ala Met Trp
145                 150                 155                 160

Met Arg Thr Ile Lys Ser Ala Glu Glu Ile Lys Leu Ile Lys Glu Gly
            165                 170                 175

Ala Arg Val Ala Asp Val Gly Gly Ala Val Ala Ala Val Lys
        180                 185                 190

Ala Gly Val Pro Glu His Glu Val Ala Ile Ala Gly Thr Thr Ala Met
    195                 200                 205

Ile Arg Glu Ile Ala Asn Ser Phe Pro Phe Val Glu Leu Met Asp Thr
210                 215                 220

Trp Thr Trp Phe Gln Ser Gly Ile Asn Thr Asp Gly Ala His Asn Pro
225                 230                 235                 240
```

```
Val Thr Asn Lys Lys Val Gln Ser Gly Glu Ile Leu Ser Leu Asn Thr
            245                 250                 255

Phe Pro Met Ile Phe Gly Tyr Tyr Thr Ala Leu Glu Arg Thr Leu Phe
        260                 265                 270

Cys Asp His Val Asp Asp Ala Ser Leu Asp Ile Trp Glu Lys Asn Val
        275                 280                 285

Lys Val His Glu Arg Gly Leu Gln Leu Ile Lys Pro Gly Ala Arg Ala
        290                 295                 300

Met Asp Ile Ala Ile Glu Leu Asn Glu Met Tyr Arg Glu Trp Asp Leu
305                 310                 315                 320

Leu Lys Tyr Arg Ser Phe Gly Tyr Gly His Ser Phe Gly Val Leu Ser
                325                 330                 335

His Tyr Tyr Gly Arg Glu Ala Gly Val Glu Leu Arg Glu Asp Ile Glu
                340                 345                 350

Thr Glu Leu Lys Pro Gly Met Val Val Ser Met Glu Pro Met Val Met
            355                 360                 365

Ile Pro Glu Gly Gln Pro Gly Ala Gly Tyr Arg Gly His Asp Ile
        370                 375                 380

Leu Val Ile Asn Asp Asp Asn Thr Val Glu Asn Ile Thr Gly Phe Pro
385                 390                 395                 400

Phe Gly Pro Glu His Asn Ile Ile Lys Asn
                405                 410

<210> SEQ ID NO 44
<211> LENGTH: 409
<212> TYPE: PRT
<213> ORGANISM: Dinoroseobacter shibae
<220> FEATURE:
<221> NAME/KEY: mat_peptide
<222> LOCATION: (1)..(409)
<223> OTHER INFORMATION: Mutant creatine amidinohydrolase Roseobacter
      sp._A8LQJ5 with C304A +C273L substitutions

<400> SEQUENCE: 44

Met Asp Gly Asn Thr Asn Val Asp Asp Met Leu His Val Met Glu Trp
1               5                   10                  15

His Asn Gly Glu Lys Glu Phe Ser Pro Phe Ser Asp Thr Glu Met Ala
            20                  25                  30

Arg Arg Gln Asn Glu Leu Arg Asp Trp Met Ala Lys Asn Asp Val Asp
        35                  40                  45

Ala Ser Leu Phe Thr Ser Tyr His Cys Ile Asn Tyr Tyr Ser Gly Trp
    50                  55                  60

Leu Tyr Cys Tyr Phe Gly Arg Lys Tyr Gly Met Val Ile Asp Gln Lys
65                  70                  75                  80

Asn Ala Thr Thr Ile Ser Ala Gly Ile Asp Gly Gly Gln Pro Phe Arg
                85                  90                  95

Arg Ser Phe Gly Asn Asn Ile Thr Tyr Thr Asp Trp Arg Arg Asp Asn
            100                 105                 110

Phe Tyr Arg Ala Ile Gln Gln Leu Thr Pro Gly Ala Lys Arg Ile Gly
        115                 120                 125

Ile Glu Phe Asp His Val Ser Leu Glu Tyr Arg Gln Leu Leu Gln Asp
    130                 135                 140

Ala Leu Pro Gly Val Glu Phe Val Asp Val Gly Gln Pro Ala Met Trp
145                 150                 155                 160

Met Arg Thr Ile Lys Ser Ala Glu Glu Ile Lys Leu Ile Lys Glu Gly
                165                 170                 175
```

```
Ala Arg Val Ala Asp Val Gly Gly Ala Val Ala Ala Val Lys
            180                 185                 190

Ala Gly Val Pro Glu His Glu Val Ala Ile Ala Gly Thr Thr Ala Met
            195                 200                 205

Ile Arg Glu Ile Ala Asn Ser Phe Pro Phe Val Glu Leu Met Asp Thr
    210                 215                 220

Trp Thr Trp Phe Gln Ser Gly Ile Asn Thr Asp Gly Ala His Asn Pro
225                 230                 235                 240

Val Thr Asn Lys Lys Val Gln Ser Gly Glu Ile Leu Ser Leu Asn Thr
                245                 250                 255

Phe Pro Met Ile Phe Gly Tyr Tyr Thr Ala Leu Glu Arg Thr Leu Phe
            260                 265                 270

Leu Asp His Val Asp Asp Ala Ser Leu Asp Ile Trp Glu Lys Asn Val
            275                 280                 285

Lys Val His Glu Arg Gly Leu Gln Leu Ile Lys Pro Gly Ala Arg Ala
    290                 295                 300

Met Asp Ile Ala Ile Glu Leu Asn Glu Met Tyr Arg Glu Trp Asp Leu
305                 310                 315                 320

Leu Lys Tyr Arg Ser Phe Gly Tyr Gly His Ser Phe Gly Val Leu Ser
                325                 330                 335

His Tyr Tyr Gly Arg Glu Ala Gly Val Glu Leu Arg Glu Asp Ile Glu
            340                 345                 350

Thr Glu Leu Lys Pro Gly Met Val Ser Met Glu Pro Met Val Met
            355                 360                 365

Ile Pro Glu Gly Gln Pro Gly Ala Gly Tyr Arg Glu His Asp Ile
    370                 375                 380

Leu Val Ile Asn Asp Asp Asn Thr Val Glu Asn Ile Thr Gly Phe Pro
385                 390                 395                 400

Phe Gly Pro Glu His Asn Ile Ile Lys
                405

<210> SEQ ID NO 45
<211> LENGTH: 1140
<212> TYPE: DNA
<213> ORGANISM: Paracoccus denitrificans
<220> FEATURE:
<221> NAME/KEY: CDS
<222> LOCATION: (1)..(1140)
<223> OTHER INFORMATION: ABL71480.1 Paracoccus denitrificans PD1222 gene
      encoding creatine amidinohydrolase [A1B7I6]

<400> SEQUENCE: 45 atg cag cgg cgc cag gac gac atg cgc cgc tgg atg gcc ggg aac ggc    48
Met Gln Arg Arg Gln Asp Asp Met Arg Arg Trp Met Ala Gly Asn Gly
1               5                   10                  15 gtc gat gcg gca ctg ttc acc tcg tat cac tgc atc aac tat tat tcg    96
Val Asp Ala Ala Leu Phe Thr Ser Tyr His Cys Ile Asn Tyr Tyr Ser
            20                  25                  30 ggc tgg ctc tac tgc tat ttc ggc cgc aaa tac ggc atg gtc atc acc   144
Gly Trp Leu Tyr Cys Tyr Phe Gly Arg Lys Tyr Gly Met Val Ile Thr
        35                  40                  45 cag gac gcg gcg acc acc atc agc gcc ggc atc gat ggc ggt cag ccg   192
Gln Asp Ala Ala Thr Thr Ile Ser Ala Gly Ile Asp Gly Gly Gln Pro
    50                  55                  60 tgg cgg cgc agc ttt ggc ggc aac gtc acc tat acc gat tgg cgg cgc   240
Trp Arg Arg Ser Phe Gly Gly Asn Val Thr Tyr Thr Asp Trp Arg Arg
65                  70                  75                  80 gac aat tat ttc cgc gcg gtg cgg cag ctg acc ccc ggc gtc aag cgg   288
```

```
                Asp Asn Tyr Phe Arg Ala Val Arg Gln Leu Thr Pro Gly Val Lys Arg
                                 85                  90                  95 ctg gga atc gag ttc gac cat gtc aac atg gac ttg cgc cgc cag ctt          336
Leu Gly Ile Glu Phe Asp His Val Asn Met Asp Leu Arg Arg Gln Leu
                100                 105                 110 gag gca gcc ctg ccg ggg gtg gaa ttc gtc gat gtc ggc cag ccc tcg          384
Glu Ala Ala Leu Pro Gly Val Glu Phe Val Asp Val Gly Gln Pro Ser
            115                 120                 125 atg tgg atg cgc tcg atc aag tcg gcc gag gaa cac aag ctg atc cgc          432
Met Trp Met Arg Ser Ile Lys Ser Ala Glu Glu His Lys Leu Ile Arg
        130                 135                 140 gag ggc gcg cgc atc tgc gac gtg ggc ggc gcg gcg gtg gcg gct gcg          480
Glu Gly Ala Arg Ile Cys Asp Val Gly Gly Ala Ala Val Ala Ala Ala
145                 150                 155                 160 gtc aag gcg ggc gtg ccc gag cac gag gtc gcc atc gcc tcg acc aat          528
Val Lys Ala Gly Val Pro Glu His Glu Val Ala Ile Ala Ser Thr Asn
                165                 170                 175 gcc atg atc cgc gag gtc gcc gcc tcc ttc ccc ttc gtc gag ctg atg          576
Ala Met Ile Arg Glu Val Ala Ala Ser Phe Pro Phe Val Glu Leu Met
                180                 185                 190 gat acc tgg acc tgg ttc cag tcc ggc atc aac acc gac ggg gcg cat          624
Asp Thr Trp Thr Trp Phe Gln Ser Gly Ile Asn Thr Asp Gly Ala His
            195                 200                 205 aac ccg gtg acg aac aag aag atc gca tcg ggc gag atc ctg tcg ctg          672
Asn Pro Val Thr Asn Lys Lys Ile Ala Ser Gly Glu Ile Leu Ser Leu
        210                 215                 220 aac tgc ttc ccg atg atc ttc ggc tat tat acc gcg ctg gaa cgc acg          720
Asn Cys Phe Pro Met Ile Phe Gly Tyr Tyr Thr Ala Leu Glu Arg Thr
225                 230                 235                 240 atg ttt tgc gac agc gtg gac gat gcc agc ctc gac atc tgg gaa aag          768
Met Phe Cys Asp Ser Val Asp Asp Ala Ser Leu Asp Ile Trp Glu Lys
                245                 250                 255 aac gtc gcc gtg cat cgc cgg ggc ctg gaa ctg atc aag ccc ggt gcg          816
Asn Val Ala Val His Arg Arg Gly Leu Glu Leu Ile Lys Pro Gly Ala
                260                 265                 270 aaa tgc aac gag atc gca ttg gag ctc aac gac atg tac cgc cag tgg          864
Lys Cys Asn Glu Ile Ala Leu Glu Leu Asn Asp Met Tyr Arg Gln Trp
            275                 280                 285 gat ctg ctg aaa tat cgc agc ttc ggc tat ggc cac tcc ttc ggc gtc          912
Asp Leu Leu Lys Tyr Arg Ser Phe Gly Tyr Gly His Ser Phe Gly Val
        290                 295                 300 ctg agc cac tat tac ggg cgc gag gcc ggg gtc gag ctg cgc gag gac          960
Leu Ser His Tyr Tyr Gly Arg Glu Ala Gly Val Glu Leu Arg Glu Asp
305                 310                 315                 320 atc gag acc gag ctg aag ccc ggc atg gtg gtc tcg atg gaa ccg atg         1008
Ile Glu Thr Glu Leu Lys Pro Gly Met Val Val Ser Met Glu Pro Met
                325                 330                 335 gtg atg ttg ccc gag ggt gcg ccc ggc gcg ggc ggc tat cgc gag cat         1056
Val Met Leu Pro Glu Gly Ala Pro Gly Ala Gly Gly Tyr Arg Glu His
                340                 345                 350 gac atc ctg atc gtg acc gag gac ggg gcc gat aac atc acc ggg ttc         1104
Asp Ile Leu Ile Val Thr Glu Asp Gly Ala Asp Asn Ile Thr Gly Phe
            355                 360                 365 ccc ttc ggc ccc gag cac aac atc atc cgc aac tga                         1140
Pro Phe Gly Pro Glu His Asn Ile Ile Arg Asn
        370                 375

<210> SEQ ID NO 46
<211> LENGTH: 379
<212> TYPE: PRT
```

<213> ORGANISM: Paracoccus denitrificans

<400> SEQUENCE: 46

| | | | | | | | | | | | | | | | |
|---|---|---|---|---|---|---|---|---|---|---|---|---|---|---|---|

Met Gln Arg Arg Gln Asp Met Arg Arg Trp Met Ala Gly Asn Gly
1               5                   10                  15

Val Asp Ala Ala Leu Phe Thr Ser Tyr His Cys Ile Asn Tyr Tyr Ser
                20                  25                  30

Gly Trp Leu Tyr Cys Tyr Phe Gly Arg Lys Tyr Gly Met Val Ile Thr
            35                  40                  45

Gln Asp Ala Ala Thr Thr Ile Ser Ala Gly Ile Asp Gly Gly Gln Pro
        50                  55                  60

Trp Arg Arg Ser Phe Gly Gly Asn Val Thr Tyr Thr Asp Trp Arg Arg
65                  70                  75                  80

Asp Asn Tyr Phe Arg Ala Val Arg Gln Leu Thr Pro Gly Val Lys Arg
                85                  90                  95

Leu Gly Ile Glu Phe Asp His Val Asn Met Asp Leu Arg Arg Gln Leu
            100                 105                 110

Glu Ala Ala Leu Pro Gly Val Glu Phe Val Asp Val Gly Gln Pro Ser
        115                 120                 125

Met Trp Met Arg Ser Ile Lys Ser Ala Glu Glu His Lys Leu Ile Arg
130                 135                 140

Glu Gly Ala Arg Ile Cys Asp Val Gly Gly Ala Ala Val Ala Ala Ala
145                 150                 155                 160

Val Lys Ala Gly Val Pro Glu His Glu Val Ala Ile Ala Ser Thr Asn
                165                 170                 175

Ala Met Ile Arg Glu Val Ala Ala Ser Phe Pro Phe Val Glu Leu Met
            180                 185                 190

Asp Thr Trp Thr Trp Phe Gln Ser Gly Ile Asn Thr Asp Gly Ala His
        195                 200                 205

Asn Pro Val Thr Asn Lys Lys Ile Ala Ser Gly Glu Ile Leu Ser Leu
210                 215                 220

Asn Cys Phe Pro Met Ile Phe Gly Tyr Tyr Thr Ala Leu Glu Arg Thr
225                 230                 235                 240

Met Phe Cys Asp Ser Val Asp Asp Ala Ser Leu Asp Ile Trp Glu Lys
                245                 250                 255

Asn Val Ala Val His Arg Arg Gly Leu Glu Leu Ile Lys Pro Gly Ala
            260                 265                 270

Lys Cys Asn Glu Ile Ala Leu Glu Leu Asn Asp Met Tyr Arg Gln Trp
        275                 280                 285

Asp Leu Leu Lys Tyr Arg Ser Phe Gly Tyr Gly His Ser Phe Gly Val
290                 295                 300

Leu Ser His Tyr Tyr Gly Arg Glu Ala Gly Val Glu Leu Arg Glu Asp
305                 310                 315                 320

Ile Glu Thr Glu Leu Lys Pro Gly Met Val Val Ser Met Glu Pro Met
                325                 330                 335

Val Met Leu Pro Glu Gly Ala Pro Ala Gly Gly Tyr Arg Glu His
            340                 345                 350

Asp Ile Leu Ile Val Thr Glu Asp Gly Ala Asp Asn Ile Thr Gly Phe
        355                 360                 365

Pro Phe Gly Pro Glu His Asn Ile Ile Arg Asn
370                 375

<210> SEQ ID NO 47
<211> LENGTH: 379

```
<212> TYPE: PRT
<213> ORGANISM: Paracoccus denitrificans
<220> FEATURE:
<221> NAME/KEY: mat_peptide
<222> LOCATION: (1)..(379)
<223> OTHER INFORMATION: Mutant creatine amidinohydrolase Paracoccus
      denitrificans _A1B7I6 with C150A+C274A substitutions

<400> SEQUENCE: 47
```

Met Gln Arg Arg Gln Asp Asp Met Arg Arg Trp Met Ala Gly Asn Gly
1               5                   10                  15

Val Asp Ala Ala Leu Phe Thr Ser Tyr His Cys Ile Asn Tyr Tyr Ser
                20                  25                  30

Gly Trp Leu Tyr Cys Tyr Phe Gly Arg Lys Tyr Gly Met Val Ile Thr
            35                  40                  45

Gln Asp Ala Ala Thr Thr Ile Ser Ala Gly Ile Asp Gly Gly Gln Pro
        50                  55                  60

Trp Arg Arg Ser Phe Gly Gly Asn Val Thr Tyr Thr Asp Trp Arg Arg
65              70                  75                  80

Asp Asn Tyr Phe Arg Ala Val Arg Gln Leu Thr Pro Gly Val Lys Arg
                85                  90                  95

Leu Gly Ile Glu Phe Asp His Val Asn Met Asp Leu Arg Arg Gln Leu
            100                 105                 110

Glu Ala Ala Leu Pro Gly Val Glu Phe Val Asp Val Gly Gln Pro Ser
        115                 120                 125

Met Trp Met Arg Ser Ile Lys Ser Ala Glu Glu His Lys Leu Ile Arg
130             135                 140

Glu Gly Ala Arg Ile Ala Asp Val Gly Gly Ala Val Ala Ala Ala
145                 150                 155                 160

Val Lys Ala Gly Val Pro Glu His Glu Val Ala Ile Ala Ser Thr Asn
                165                 170                 175

Ala Met Ile Arg Glu Val Ala Ala Ser Phe Pro Phe Val Glu Leu Met
            180                 185                 190

Asp Thr Trp Thr Trp Phe Gln Ser Gly Ile Asn Thr Asp Gly Ala His
        195                 200                 205

Asn Pro Val Thr Asn Lys Lys Ile Ala Ser Gly Glu Ile Leu Ser Leu
            210                 215                 220

Asn Cys Phe Pro Met Ile Phe Gly Tyr Tyr Thr Ala Leu Glu Arg Thr
225                 230                 235                 240

Met Phe Cys Asp Ser Val Asp Asp Ala Ser Leu Asp Ile Trp Glu Lys
                245                 250                 255

Asn Val Ala Val His Arg Arg Gly Leu Glu Leu Ile Lys Pro Gly Ala
            260                 265                 270

Lys Ala Asn Glu Ile Ala Leu Glu Leu Asn Asp Met Tyr Arg Gln Trp
        275                 280                 285

Asp Leu Leu Lys Tyr Arg Ser Phe Gly Tyr Gly His Ser Phe Gly Val
        290                 295                 300

Leu Ser His Tyr Tyr Gly Arg Glu Ala Gly Val Leu Arg Glu Asp
305                 310                 315                 320

Ile Glu Thr Glu Leu Lys Pro Gly Met Val Val Ser Met Glu Pro Met
                325                 330                 335

Val Met Leu Pro Glu Gly Ala Pro Gly Ala Gly Tyr Arg Glu His
            340                 345                 350

Asp Ile Leu Ile Val Thr Glu Asp Gly Ala Asp Asn Ile Thr Gly Phe
        355                 360                 365

```
Pro Phe Gly Pro Glu His Asn Ile Ile Arg Asn
        370                 375
```

<210> SEQ ID NO 48
<211> LENGTH: 379
<212> TYPE: PRT
<213> ORGANISM: Paracoccus denitrificans
<220> FEATURE:
<221> NAME/KEY: mat_peptide
<222> LOCATION: (1)..(379)
<223> OTHER INFORMATION: Mutant creatine amidinohydrolase Paracoccus
    denitrificans _A1B7I6 with C150A+C274A+C243L substitutions

<400> SEQUENCE: 48

```
Met Gln Arg Arg Gln Asp Asp Met Arg Arg Trp Met Ala Gly Asn Gly
1               5                   10                  15

Val Asp Ala Ala Leu Phe Thr Ser Tyr His Cys Ile Asn Tyr Tyr Ser
            20                  25                  30

Gly Trp Leu Tyr Cys Tyr Phe Gly Arg Lys Tyr Gly Met Val Ile Thr
        35                  40                  45

Gln Asp Ala Ala Thr Thr Ile Ser Ala Gly Ile Asp Gly Gly Gln Pro
    50                  55                  60

Trp Arg Arg Ser Phe Gly Gly Asn Val Thr Tyr Thr Asp Trp Arg Arg
65                  70                  75                  80

Asp Asn Tyr Phe Arg Ala Val Arg Gln Leu Thr Pro Gly Val Lys Arg
                85                  90                  95

Leu Gly Ile Glu Phe Asp His Val Asn Met Asp Leu Arg Arg Gln Leu
            100                 105                 110

Glu Ala Ala Leu Pro Gly Val Glu Phe Val Asp Val Gly Gln Pro Ser
        115                 120                 125

Met Trp Met Arg Ser Ile Lys Ser Ala Glu Glu His Lys Leu Ile Arg
    130                 135                 140

Glu Gly Ala Arg Ile Ala Asp Val Gly Gly Ala Ala Val Ala Ala Ala
145                 150                 155                 160

Val Lys Ala Gly Val Pro Glu His Glu Val Ala Ile Ala Ser Thr Asn
                165                 170                 175

Ala Met Ile Arg Glu Val Ala Ala Ser Phe Pro Phe Val Glu Leu Met
            180                 185                 190

Asp Thr Trp Thr Trp Phe Gln Ser Gly Ile Asn Thr Asp Gly Ala His
        195                 200                 205

Asn Pro Val Thr Asn Lys Lys Ile Ala Ser Gly Glu Ile Leu Ser Leu
    210                 215                 220

Asn Cys Phe Pro Met Ile Phe Gly Tyr Tyr Thr Ala Leu Glu Arg Thr
225                 230                 235                 240

Met Phe Leu Asp Ser Val Asp Asp Ala Ser Leu Asp Ile Trp Glu Lys
                245                 250                 255

Asn Val Ala Val His Arg Arg Gly Leu Glu Leu Ile Lys Pro Gly Ala
            260                 265                 270

Lys Ala Asn Glu Ile Ala Leu Glu Leu Asn Asp Met Tyr Arg Gln Trp
        275                 280                 285

Asp Leu Leu Lys Tyr Arg Ser Phe Gly Tyr Gly His Ser Phe Gly Val
    290                 295                 300

Leu Ser His Tyr Tyr Gly Arg Glu Ala Gly Val Glu Leu Arg Glu Asp
305                 310                 315                 320

Ile Glu Thr Glu Leu Lys Pro Gly Met Val Val Ser Met Glu Pro Met
                325                 330                 335
```

```
Val Met Leu Pro Glu Gly Ala Pro Gly Ala Gly Gly Tyr Arg Glu His
            340             345             350

Asp Ile Leu Ile Val Thr Glu Asp Gly Ala Asp Asn Ile Thr Gly Phe
            355             360             365

Pro Phe Gly Pro Glu His Asn Ile Ile Arg Asn
            370             375
```

MODIFIED CREATINASE

This application is a national stage filing under 35 U.S.C. § 371 of International Application No. PCT/EP2016/053760, filed on Feb. 23, 2016, which claims priority of Danish Patent Application No. PA 2015 00114, filed Feb. 27, 2015. The contents of these applications are each incorporated herein by reference.

FIELD OF THE INVENTION

The invention relates to a mutant polypeptide having *creatine amidinohydrolase* activity, where the polypeptide both retains activity in the presence of reagents that modify thiol groups and has enhanced thermostability. The invention further relates to methods for producing the mutant polypeptide; and to a sensor comprising the mutant polypeptide for use in the measurement of creatinine in samples of physiological fluids. Additionally, the invention teaches how to use the mutant polypeptide to enhance the life-time of a creatinine sensor, and a method for producing the sensor.

BACKGROUND OF THE INVENTION

The level of creatinine in samples of physiological fluids, such as whole blood, serum, plasma or urine, is an important indicator of renal function. Creatine phosphate is stored in the muscles of vertebrates and provides an energy reserve. It is irreversibly converted into creatinine (a degradation product) and the energy rich phosphate group. During normal muscle function about 1-2% per day of the total amount of creatine phosphate is converted into creatinine. Creatinine is released into the blood and removed by the kidneys. In a healthy individual the level of creatinine is thus relatively constant at about 35 to about 75 µM. If the level of creatinine in the blood increases it may be a sign of some malfunction of the kidneys. In such cases the level of creatinine may increase to levels as high as 2,000 µM.

The level of creatinine in a sample of physiological fluid derived from a subject can be measured enzymatically, for example using creatinine iminohydrolase (by detection of $NH_3$) or creatinine amidohydrolase. Creatinine amidohydrolase is also referred to as "creatininase". In the case of creatininase, the creatinine level in a physiological fluid can be determined by a cascade of enzymatic reactions involving the enzymes creatininase (EC 3.5.2.10), *creatine amidinohydrolase* (EC 3.5.3.3—"*creatinase*") and sarcosine oxidase (EC 1.5.3.1) as represented by the following reactions:

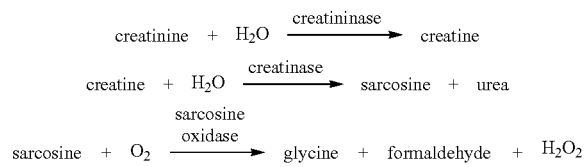

This reaction cascade results in the formation of $H_2O_2$, which in turn may be detected amperometrically or photometrically. In some systems a further enzyme (e.g., peroxidase) or an indicator may be used (e.g., a luminophor).

The level of creatinine in samples of physiological fluids can be measured using a sensor adapted for measurement of creatinine, for example a sensor comprising creatininase in combination with the enzymes *creatinase* and sarcosine oxidase. Such sensors are often referred to as biosensors and may employ both electrochemical and/or photometric principles.

The intermediate product creatine is also present in samples of blood, serum, plasma or urine as such. Therefore, a dual sensor system is preferably employed if the creatinine is to be determined by the above cascade of enzymatic reactions. Using a dual sensor system the creatinine may be determined as the difference between the total of the two substances and the intermediate product alone. Accordingly, in a first sensor for the determination of the total concentration of creatinine and creatine in the sample, both creatininase, *creatinase* and sarcosine oxidase are present for converting creatinine and creatine into $H_2O_2$. In a second sensor for the determination of the concentration of creatine in the sample, *creatinase* and sarcosine oxidase are present for converting creatine into $H_2O_2$. The concentration of creatinine in the sample is thus determined from the difference between the total concentration of creatinine and creatine in the sample and the concentration of creatine in the sample.

Biosensors designed for analysis of consecutive samples of physiological fluids commonly employ a flow channel for delivery of samples to and from the sensor; where delivery of each sample is typically followed by a rinse step prior to analysis of a subsequent sample. The rinse step serves to prevent contamination of one sample by the next, but may additionally be used to prevent bacterial growth and bio-film formation in the sensor and sample flow channels. Rinse (or preservative) solutions comprising the active agent 2-methyl-4-isothiazolin-3-one, also known as Methylisothiazolinone or MIT, or other isothiazolinone-derived biocides may be utilized for controlling microbial growth in water-containing solutions.

Isothiazolinone or MIT, present in preservative solutions, are thiol-interactive agents, that interact with various proteins/enzymes in bacteria and fungi, leading to inhibition of cell growth; irreversible cell damage and cell death. A drawback with use of isothiazolinone or MIT agents is that by reacting and inactivating one or more thiol group-containing enzyme in a biosensor, they can limit the useful lifetime of the biosensor. Creatinase is a thiol containing hydrolase, whose activity may be inhibited by thiol-interactive agents, such as isothiazolinone-derived agents, including MIT, which limits the use of these preservative agents in sensors used for measuring creatinine in samples of physiological fluids.

Accordingly, there exists a need for a *creatinase* enzyme that is more resistant to thiol-interactive agents; allowing the use of such agents in the rinse solution in a sensor for measurement of creatinine. Furthermore, there is a need for a *creatinase* enzyme having both enhanced resistance to thiol-interactive agents, while at the same time having thermostable properties. This is because biosensors mounted in an analyzer are commonly used and stored at 37° C., so it is important that the components of the biosensor are stable over a range of ambient temperatures, for example at least up to 37° C.

According to JPH10174585 (A), bacteria belonging to the genus *Alcaligenes*, in general, exhibit excellent thermal stability. JPH10174585 (A), further discloses the use of protein engineering techniques to produce a mutant *Alcaligenes* gene encoding a mutant *creatine amidinohydrolase* having improved long-term stability at temperatures such as 45° C. The mutant enzyme was characterized by one, or two or more combined substituted positions out of glutamic acid at $15^{th}$ position, and arginine at $104^{th}$ and $135^{th}$ positions in comparison with a wild type *creatine amidinohydrolase*; where the wild type sequence is set out in AB016788.

An *Alcaligenes* strain KS-85 gene is reported to encode a thermostable *creatinase* (EC 3.5.3.3) in GenBank: BAA88830.1.

JPH07255485 (A) describes a mutant *creatinase* obtained by mutation of a *Flavobacterium* U-188 *creatinase* gene mutation; whereby at least one of the 166$^{th}$, 277$^{th}$ and 328$^{th}$ amino acid sequences is substituted with a hydrophobic amino acid such as isoleucine. The mutant *creatinase* held activity for 1 hour when stored at 55° C.

SUMMARY OF THE INVENTION

The present invention provides a mutant *creatinase* that is more resistant to thiol-agents such as MIT or other isothiazolinone-derived agents. A sensor comprising the mutant *creatinase* is compatible with the use of a preservative such as Neolone 950 by having a longer life-time when used in combination with a "standard" (and effective) concentration of Neolone 950.

According to a first embodiment, the invention provides an isolated mutant polypeptide having *creatine amidinohydrolase* activity that retains enzymatic activity in the presence of thiol-agents such as MIT or other isothiazolinone-derived agents at temperatures of above 25° C., wherein the polypeptide is:
  a. a polypeptide comprises an amino acid sequence having at least 80% identity to SEQ ID No: 2; wherein amino acid residue cysteine at position 175 is substituted with alanine and amino acid residue cysteine at position 299 is substituted with alanine, or
  b. a polypeptide having an amino acid sequence selected from among SEQ ID No 3 (corresponding to *Alcaligenes* sp. *creatine amidinohydrolase*—Uniprot: Q9RHU9 with substitutions: C175A+C299A); SEQ ID No 7 (corresponding to *Ochrobactrum anthropic creatinase*—Uniprot: A0A076WGB5 with substitutions: C171A+C295A); SEQ ID No 11 (corresponding to *Mesorhizobium* sp. LNHC221B00 *creatinase*—Uniprot: X6DLM3 with substitutions: S175A+C299A); SEQ ID No 15 (corresponding to *Roseovarius* sp TM1035 *creatinase*—Uniprot: A6DVF8 with substitutions: C175A+C299A); SEQ ID No 19 (corresponding to *Roseovarius* sp 217 *creatinase*—Uniprot: A3W1E4 with substitutions: C175A+C299A); SEQ ID No 23 (corresponding to *Paracoccus denitrificans creatinase*—Uniprot: A1B0T5 with substitutions: C175A+C299A); SEQ ID No 27 (corresponding to *Rubellimicrobium mesophilum creatinase*—Uniprot: A0A017HRV0 with substitutions: C175A+C299A); SEQ ID No. 31 (corresponding to *Loktanella vestfoldensis* SKA53 *creatinase*—Uniprot: A3V128 with substitutions: C298A); SEQ ID No. 35 (corresponding to *Lutibaculum baratangense* AMV1 *creatinase*—Uniprot: V4RGE5 with substitutions: C180A+C304A); SEQ ID No. 39 (corresponding to *Roseobacter* sp. AzwK-3b *creatinase*—Uniprot: A6FQQ7 with substitution: C299A); SEQ ID No. 43 (corresponding to *Dinoroseobacter shibae creatinase*—Uniprot: A8LQJ5 with substitution: C304A); SEQ ID No. 47 (corresponding to *Paracoccus denitrificans creatinase*—Uniprot: A1B7I6 with substitution: C150A+C274A).

According to a further embodiment, the said isolated mutant polypeptide comprises:
  a. an amino acid sequence having at least 80% identity to SEQ ID No: 2; wherein the amino acid residue corresponding to the cysteine at position 175 in SEQ ID No: 2 is alanine, and the amino acid residue corresponding to the cysteine at position 299 in SEQ ID No: 2 is alanine and the amino acid residue corresponding to the cysteine at position 268 in SEQ ID No: 2 is selected from leucine, valine, isoleucine or alanine; or
  b. an amino acid sequence selected from among SEQ ID No 4 (corresponding to *Alcaligenes* sp. *creatine amidinohydrolase*—Uniprot: Q9RHU9 with substitutions: C175A+C299A+C268L); SEQ ID No 8 (corresponding to *Ochrobactrum anthropic creatinase*—Uniprot: A0A076WGB5 with substitutions: C171A+C295A+C264L); SEQ ID No 12 (corresponding to *Mesorhizobium* sp. LNHC221B00 *creatinase*—Uniprot: X6DLM3 with substitutions: S175A+C299A+C268L); SEQ ID No 16 (corresponding to *Roseovarius* sp TM1035 *creatinase*—Uniprot: A6DVF8 with substitutions: C175A+C299A+C268L); SEQ ID No 20 (corresponding to *Roseovarius* sp 217 *creatinase*—Uniprot: A3W1E4 with substitutions: C175A+C299A+C268L); SEQ ID No 24 (corresponding to *Paracoccus denitrificans creatinase*—Uniprot: A1B0T5 with substitutions: C175A+C299A+C268L); SEQ ID No 28 (corresponding to *Rubellimicrobium mesophilum creatinase*—Uniprot: A0A017HRV0 with substitutions: C175A+C299A+C268L); SEQ ID No. 32 (corresponding to *Loktanella vestfoldensis* SKA53 *creatinase*—Uniprot: A3V128 with substitutions: C298A+C267L); SEQ ID No. 36 (corresponding to *Lutibaculum baratangense* AMV1 *creatinase*—Uniprot: V4RGE5 with substitutions: C180A+C304A+C273L); SEQ ID No. 40 (corresponding to *Roseobacter* sp. AzwK-3b *creatinase*—Uniprot: A6FQQ7 with substitution: C299A+C268L); SEQ ID No. 44 (corresponding to *Dinoroseobacter shibae creatinase*—Uniprot: A8LQJ5 with substitution: C304A+C273L); SEQ ID No. 48 (corresponding to *Paracoccus denitrificans creatinase*—Uniprot: A1B7I6 with substitution: C150A+C274A+C243L).

According to a second embodiment, the invention provides an isolated polynucleotide comprising a nucleotide sequence encoding the mutant *creatine amidinohydrolase* polypeptide.

According to a further embodiment, the invention provides a nucleic acid construct comprising the polynucleotide encoding the mutant *creatine amidinohydrolase* polypeptide, wherein the polynucleotide is operably linked to one or more control sequences that direct the production of the mutant polypeptide in an expression host.

According to a further embodiment, the invention provides a genetically modified host cell comprising a nucleic acid construct encoding the mutant the mutant *creatine amidinohydrolase* polypeptide, wherein said cell is preferably selected from among a bacterial cell, a yeast cell and a fungal cell.

According to a third embodiment, the invention provides a method for producing the mutant the mutant *creatine amidinohydrolase* polypeptide, comprising the steps of:
  a. providing a recombinant host cell, wherein the cell comprises a DNA molecule, the DNA molecule comprising a nucleic acid sequence encoding the mutant *creatine amidinohydrolase* polypeptide,
  b. incubating the host cell under conditions suitable for expression of the mutant *creatine amidinohydrolase* polypeptide, and recovering the mutant polypeptide expressed by the host cell.

According to a forth embodiment, the invention provides a composition comprising the mutant *creatine amidinohydrolase* polypeptide, wherein the composition is formulated as a dry powder, a tablet, or as a liquid; and optionally further comprises a sarcosine oxidase (EC 1.5.3.1), or both a creatininase (EC 3.5.2.10) and sarcosine oxidase (EC 1.5.3.1).

According to a fifth embodiment, the invention discloses the use of the mutant *creatine amidinohydrolase* polypeptide, or the composition comprising the mutant *creatine amidinohydrolase* polypeptide, in a sensor for determination of creatinine and/or creatine in combination with a rinse solution comprising a thiol-inactivating agent.

According to a sixth embodiment, the invention provides a sensor for determination of creatinine and/or creatine in a sample fluid comprising at least one electrode having a surface, and a plurality of enzymes immobilized on the at least one electrode surface, and wherein at least one of the enzymes is a *creatine amidinohydrolase* polypeptide that retains enzymatic activity in the presence of thiol-agents such as MIT or other isothiazolinone-derived agents at temperatures of above 25° C., for example above 30, 32, 34, 35, 37 or 40° C.

According to a further embodiment, the invention provides a method for producing a sensor for determination of creatinine or creatine in a sample fluid, comprising the step of depositing an aqueous mixture containing a plurality of enzymes on a surface of an electrode; wherein at least one of the enzymes is a mutant *creatine amidinohydrolase* polypeptide.

According to a seventh embodiment, the invention provides a method for determination of creatinine and/or creatine in a sample of physiological fluid derived from a subject comprising the steps of:
a) contacting a sensor or a dual sensor with the sample;
b) detecting creatine and/or creatinine in the sample; and a rinse step comprising:
c) contacting the sensor with a rinse solution comprising a thiol-interactive agent, wherein the rinse step (c) is either before step (a), after step (b), or both before step (a) and after step (b); wherein the method is performed at a temperature of above 25° C.; and
wherein the sensor comprises a *creatine amidinohydrolase* polypeptide that retains enzymatic activity in the presence of thiol-agents such as MIT or other isothiazolinone-derived agents at temperatures of above 25° C., for example at or above 30, 32, 34, 35, or 37° C.

DEFINITIONS

Figure 1:
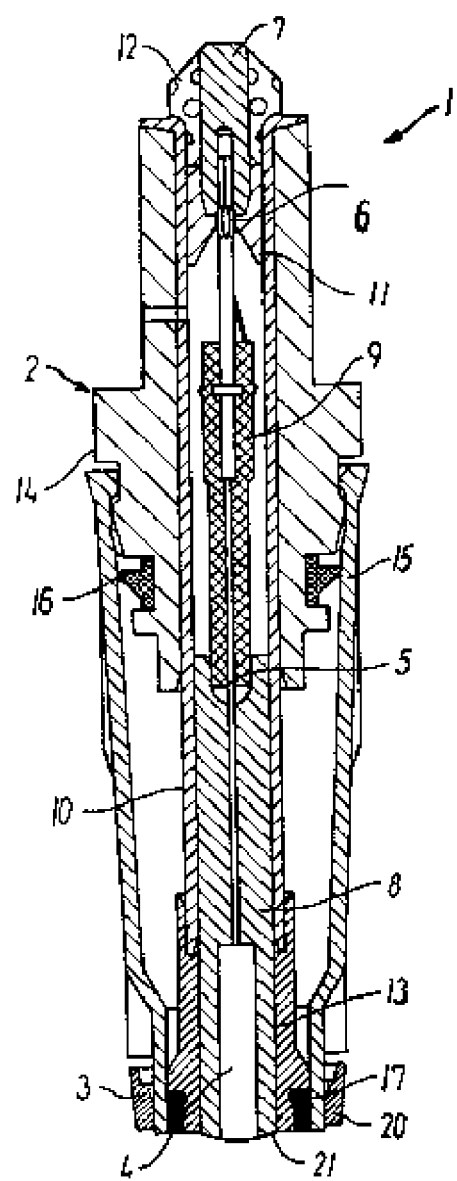
FIG. 1: illustrates a conventional enzyme sensor comprising an electrode and a membrane.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

*Creatine amidinohydrolase* activity: the term *creatine amidinohydrolase* activity (or "*creatinase*" activity) is defined as hydrolase activity which catalyzes the hydrolysis of creatine to produce sarcosine and urea, having EC number: EC 3.5.3.3. Creatinase activity is measured by incubating the *creatinase* in a phosphate buffer with creatine and sarcosine oxidase, and formation of $H_2O_2$ is detected continuously by horse radish peroxidase, 4-hydroxybenzenesulphonate and 4-aminoantipyrine. Formation of the colored product formed by oxidation of 4-hydroxybenzenesulphonate subsequently reacting with 4-aminoantipyrine is followed by increase in absorbance at 490 nm.

Decrease in sensitivity: in respect of a sensor of the invention this is the loss of sensitivity for the detection of creatinine or creatine when the sensor is exposed to a rinse solution comprising 0.11 g MIT/L at a temperature of 37° C. after a certain period of time up to several weeks.

Thermostability: a *creatinase* enzyme that retains enzymatic activity at temperatures above 25° C., for example at, or above 30, 32, 34, 35, or 37° C., preferably at, or above 35 or 37° C. is said to exhibit thermostability in the context of the present invention.

DETAILED DESCRIPTION OF THE INVENTION

The life-time of a sensor, comprising the enzymes creatininase (EC 3.5.2.10), *creatine amidinohydrolase* (EC 3.5.3.3—"*creatinase*") and sarcosine oxidase (EC 1.5.3.1) for the measurement of creatinine, was observed to be greatly reduced after a certain period of time or a certain number of measurements when a rinse solution comprising the preservative MIT (e.g. the preservative Neolone 950 comprising 9% MIT) was employed. Inactivation of *creatinase* by MIT causing a reduction in the life-time of the sensor system was especially observed at elevated temperatures, e.g. at 37° C.

The recommended concentration of Neolone 950 for preventing bacterial growth and bio-film formation in the flow channel of the sensor is about 1.25 g Neolone 950/L (corresponding to 0.11 g MIT/L) rinse solution. Inactivation of *creatinase* by Neolone 950 was found to be the cause of the short half-life of the sensor; believed to be due to interaction between the thiol agent MIT in Neolone 950 and the thiol groups in *creatinase*.

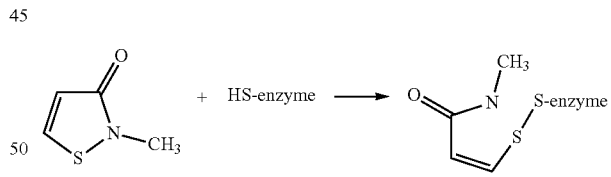

Although the life-time of the sensor can be extended to 2 weeks by reducing the amount of Neolone 950 to 0.3 g/L rinse solution; this concentration of preservative is not enough to prevent bacterial growth and bio-film formation in the sensor.

Although the native *creatinase* (EC 3.5.3.3) isolated from *Alcaligenes* sp.KS-85 is reported to be thermostable (Uniprot Q9RHU9), this enzyme becomes unstable at elevated temperatures when stored in a rinse solution comprising 0.11 g MIT/L, as can be seen from Example 1.

I. A Mutant Creatinase (EC 3.5.3.3) that is Thermostable in the Presence of Isothiazolinone-Derived Agents Synthetic genes encoding a wide range of mutant creatinases, derived from the wild-type *creatinase* (Uniprot Q9RHU9) or homologues thereof, were constructed and recombinantly expressed in order to identify a mutant that is more stable in the presence of isothiazolinone-derived agents when stored at elevated temperatures as compared to its wild-type parent enzyme. These studies revealed that a mutant *creatinase* enzyme having this combination of properties (i.e. stability at elevated temperatures and in the isothiazolinone-derived agents) was characterized by the presence of specific amino acids at positions corresponding to amino acid residue 175 and 299 in Uniprot Q9RHU9 (see example 1). It is furthermore shown that a mutant *creatinase* enzyme having this desired combination of properties can be derived from a native enzyme by firstly selecting a native *creatinase* enzyme that is structurally-related to the *Alcaligenes* sp.KS-85 *creatinase*, and then substituting one or more amino acid residue such that the expressed polypeptide has the required specific amino acids at positions corresponding to amino acid residue 175 and 299 in Uniprot Q9RHU9.

Accordingly, the present invention provides a mutant polypeptide having *creatine amidinohydrolase* activity, wherein the polypeptide has the properties of being more resistant to thiol-agents such as MIT or other isothiazolinone-derived agents; as well as exhibiting thermostability as compared to its wild-type parent enzyme. Thermostability is to be understood as the ability of the mutant polypeptide to retain at least 50% (more preferably at least 55, 60, 65, 70, 75, 80, 85 or 90%) enzymatic activity in a liquid environment after incubation at temperatures of up to about 40° C., more typically up to about 37° C. for a period of 3 or more days, for example for or above 10, 14, 21, 30, 36 or above 50 days, preferably at or above 36 days. A mutant *creatinase* enzyme of the invention is observed to retain more enzymatic activity at temperatures above 25° C., for example at, or above 30, 32, 34, 35, or 37° C., preferably at, or above 35 or 37° C. when compared to a wild-type parent enzyme.

According to one embodiment, the mutant polypeptide is derivable from the native *creatinase* enzyme from *Alcaligenes* sp (Q9RHU9_Uniprot), wherein the native enzyme has SEQ ID No: 2, or may be derived from a native *creatinase* enzyme encoded by a gene that is a homolog (i.e. ortholog or paralog) of the native gene encoding Q9RHU9 (Accession No: AB016788.1). Native *creatinase* enzymes (EC 3.5.3.3) each encoded by a gene that is a homolog (i.e. ortholog or paralog) of the native gene encoding Q9RHU9 (Accession No: AB016788.1; SEQ ID No 1) share a high degree of amino acid sequence identity, and hence their sequences can be aligned relative to each other using an appropriate program (e.g. CLUSTAL 0(1-2-1)) to reveal their sequence identity, and to locate the corresponding residues in their respective amino acid sequences. The mutant polypeptide of the invention has an amino acid sequence having at least 80% sequence identity to SEQ ID No: 3; wherein the amino acid residue corresponding to the cysteine at position 175 in SEQ ID No: 2 is alanine, and the amino acid residue corresponding to the cysteine at position 299 in SEQ ID No: 2 is alanine (see Table 1). The preferred percentage of amino acid sequence identity of the mutant polypeptide to SEQ ID No: 3 is at least 80%, such as at least 82%, at least 85%, at least 90%, at least 91%, at least 92%, at least 93%, at least 94%, at least 95%, at least 96%, at least 97%, at least 98%, at least 99%, and at least 99.5%. Preferably, the numbers of substitutions, insertions, additions or deletions of one or more amino acid residues in the polypeptide is limited, i.e. no more than 1, 2, 3, 4, 5, 6, 7, 8, 9, or 10 substitutions, and/or no more than 1, 2, 3, 4, 5, 6, 7, 8, 9, or 10 insertions, and/or no more than 1, 2, 3, 4, 5, 6, 7, 8, 9, or 10 additions, and/or no more than 1, 2, 3, 4, 5, 6, 7, 8, 9, or 10 deletions compared to the corresponding mutant polypeptide having SEQ ID NO.: 3. The term "sequence identity" as used herein, indicates a quantitative measure of the degree of identity between two amino acid sequences of substantially equal length or between two nucleic acid sequences of substantially equal length. The two sequences to be compared must be aligned to best possible fit with the insertion of gaps or alternatively, truncation at the ends of the protein or nucleic acid sequences. The sequence identity can be calculated as ((Nref−Ndif)100)/(Nref), wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Ndif=2 and Nref=8). A gap is counted as non-identity of the specific residue(s), i.e. the nucleic acid sequence AGTGTC will have a sequence identity of 75% with the nucleic acid sequence AGTCAGTC (Ndif=2 and Nref=8). Equally, the polypeptide sequence AlaGlyThrCysAlaGlyThrCys will have a sequence identity of 75% with the sequence AlaAlaThrCysAlaAlaThrCys (Ndif=2 and Nref=8). A gap is counted as non-identity of the specific residue(s), i.e. the polypeptide sequence AlaGlyThrGlyThrCys will have a sequence identity of 75% with the polypeptide sequence AlaGlyThrCysAlaGlyThrCys (Ndif=2 and Nref=8). Sequence identity can alternatively be calculated by the BLAST program e.g. the BLASTP program (Pearson W. R and D. J. Lipman (1988)) (www.ncbi.nlm.nih.gov/cgi-bin/BLAST). In one embodiment of the invention, alignment is performed with the sequence alignment method ClustalW with default parameters as described by Thompson J., et al 1994, available at http://www2.ebi.ac.uk/clustalw/.

According to a further embodiment, the mutant polypeptide has an amino acid sequence having at least 80% identity to SEQ ID No: 3; wherein the amino acid residue corresponding to the cysteine at position 175 in SEQ ID No: 2 is alanine, and the amino acid residue corresponding to the cysteine at position 299 in SEQ ID No: 2 is alanine (see Table 1); wherein the polypeptide comprises an amino acid sequence selected from among SEQ ID No 3 (corresponding to *Alcaligenes* sp. *creatine amidinohydrolase*—Uniprot: Q9RHU9 with substitutions: C175A+C299A); SEQ ID No 7 (corresponding to *Ochrobactrum anthropi creatinase*—Uniprot: A0A076WGB5 (SEQ ID No 6) with substitutions: C171A+C295A); SEQ ID No 11 (corresponding to *Mesorhizobium* sp. LNHC221B00 *creatinase*—Uniprot: X6DLM3 (SEQ ID No 10) with substitutions: S175A+C299A); SEQ ID No 15 (corresponding to *Roseovarius* sp TM1035 *creatinase*—Uniprot: A6DVF8 (SEQ ID No 14) with substitutions: C175A+C299A); SEQ ID No 19 (corresponding to *Roseovarius* sp 217 *creatinase*—Uniprot: A3W1E4 (SEQ ID No 18) with substitutions: C175A+C299A); SEQ ID No 23 (corresponding to *Paracoccus denitrificans creatinase*—Uniprot: A1B0T5 (SEQ ID No 22) with substitutions: C175A+C299A); SEQ ID No 27 (corresponding to *Rubellimicrobium mesophilum creatinase*—Uniprot: A0A017HRV0 (SEQ ID No 26) with substitutions: C175A+C299A); SEQ ID No. 31 (corresponding to *Loktanella vestfoldensis* SKA53 *creatinase*—Uniprot: A3V128 (SEQ ID No 30) with substitutions: C298A); SEQ ID No. 35 (corresponding to *Lutibaculum baratangense* AMV1 *creatinase*—Uniprot: V4RGE5 (SEQ ID No 34) with substitutions: C180A+C304A); SEQ ID No 39 (corresponding to *Roseobacter* sp. AzwK-3b *creatinase*—Uniprot: A6FQQ7 (SEQ ID No 38) with substitution: C299A); SEQ ID No. 43

(corresponding to *Dinoroseobacter shibae* creatinase—Uniprot: A8LQJ5 (SEQ ID No 42) with substitution: C304A); SEQ ID No. 47 (corresponding to *Paracoccus denitrificans* creatinase—Uniprot: A1B7I6 (SEQ ID No 46) with substitution: C150A+C274A).

According to a further embodiment, the mutant polypeptide has an amino acid sequence having at least 80% identity to SEQ ID No: 3; wherein the amino acid residue corresponding to the cysteine at position 175 in SEQ ID No: 2 is alanine, and the amino acid residue corresponding to the cysteine at position 299 in SEQ ID No: 2 is alanine and the amino acid residue corresponding to the cysteine at position 268 in SEQ ID No: 2 is selected from leucine, valine, isoleucine or alanine, preferably leucine (see Table 1).

According to a further embodiment, the mutant polypeptide has an amino acid sequence having at least 80% identity to SEQ ID No: 3; wherein the amino acid residue corresponding to the cysteine at position 175 in SEQ ID No: 2 is alanine, and the amino acid residue corresponding to the cysteine at position 299 in SEQ ID No: 2 is alanine, and the amino acid residue corresponding to the cysteine at position 268 in SEQ ID No: 2 is leucine (see Table 1); wherein the polypeptide comprises an amino acid sequence selected from among SEQ ID No 4 (corresponding to *Alcaligenes* sp. creatine amidinohydrolase—Uniprot: Q9RHU9 (SEQ ID No 2) with substitutions: C175A+C299A+C268L); SEQ ID No 8 (corresponding to *Ochrobactrum anthropic* creatinase—Uniprot: A0A076WGB5 (SEQ ID No 6) with substitutions: C171A+C295A+C264L); SEQ ID No 12 (corresponding to *Mesorhizobium* sp. LNHC221B00 creatinase—Uniprot: X6DLM3 (SEQ ID No 10) with substitutions: S175A+C299A+C268L); SEQ ID No 16 (corresponding to *Roseovarius* sp TM1035 creatinase—Uniprot: A6DVF8 (SEQ ID No 14) with substitutions: C175A+C299A+C268L); SEQ ID No 20 (corresponding to *Roseovarius* sp 217 creatinase—Uniprot: A3W1E4 (SEQ ID No 18) with substitutions: C175A+C299A+C268L); SEQ ID No 24 (corresponding to *Paracoccus denitrificans* creatinase—Uniprot: A1B0T5 (SEQ ID No 22) with substitutions: C175A+C299A+C268L); SEQ ID No 28 (corresponding to *Rubellimicrobium mesophilum* creatinase—Uniprot: A0A017HRV0 (SEQ ID No 26) with substitutions: C175A+C299A+C268L); SEQ ID No. 32 (corresponding to *Loktanella vestfoldensis* SKA53 creatinase—Uniprot: A3V128 (SEQ ID No 30) with substitutions: C298A+C267L); SEQ ID No. 36 (corresponding to *Lutibaculum baratangense* AMV1 creatinase—Uniprot: V4RGE5 (SEQ ID No 34) with substitutions: C180A+C304A+C273L); SEQ ID No. 40 (corresponding to *Roseobacter* sp. AzwK-3b creatinase—Uniprot: A6FQQ7 (SEQ ID No 38) with substitution: C299A+C268L); SEQ ID No. 44 (corresponding to *Dinoroseobacter shibae* creatinase—Uniprot: A8LQJ5 (SEQ ID No 42) with substitution: C304A+C273L); SEQ ID No. 48 (corresponding to *Paracoccus denitrificans* creatinase—Uniprot: A1B7I6 (SEQ ID No 46) with substitution: C150A+C274A+C243L).

According to a further embodiment, the mutant polypeptide has an amino acid sequence having at least 80% identity to SEQ ID No: 2; wherein the amino acid residue corresponding to the cysteine at position 175 in SEQ ID No: 2 is alanine; the amino acid residue corresponding to the cysteine at position 299 in SEQ ID No: 2 is alanine; and the amino acid residue corresponding to position 202 in SEQ ID No 2 is alanine and the amino acid residue corresponding to position 312 in SEQ ID No 2 is glutamate; and optionally the amino acid residue corresponding to the cysteine at position 268 in SEQ ID No: 2 is selected from leucine, valine, isoleucine or alanine (see Table 1).

TABLE 1

```
            Alignment of creatinase enzymes of the invention

|Q9RHU9|     -----MTDDMLHVMKWHNGEKDYSPFSDAEMTRRQNDVRGWMAKNNVDAALFTSYHCINY   55
|A0A076WGB5| ---------MLHVMKWHNGEKDYSPFSEAEMTRRQNDVRGWMAKNDVDAALFTSYHCINY   51
|X6DLM3|     -----MTDDMLHVVKWHNGEKDYSPFSEAEMKRRQNDVRRWMADNNVDAALFTSYHCINY   55
|A6DVF8|     -----MLDDMLHVTEWHNGEKEFSPFSDNEMARRQNELRVWMADNNVDAALFTSYHCINY   55
|A3W1E4|     -----MLDDMLHVTEWHNGEKEFSPFSDNEMARRQNELRVWMADNNVDAALFTSYHCINY   55
|A1B0T5|     -----MTDDMLHVMEWHNGDKDFSPFSDAEMQRRQDDMRRWMAGNGVDAALFTSYHCINY   55
|A0A017HRV0| -----MAEDMLHVMGWHNGDKEYSPFSEAEMSRRQGDIRTWMAENDVDAALFTSYHCINY   55
|A3V128|     ------MDDMLHVMEWHNGEKEFSPFSDNEMARRQNELRDWMGKNDVDASLFTSYHCINY   54
|V4RGE5|     MLDKTILDDMVHVTEWHNGEKEFLPFSDAEMSRRQDDVRSWMGANNVDAALFTSYHCINY   60
|A6FQQ7|     -----MLDDMLHVTEWHNGEKEFSPFSDNEMARRQNELRDWMAKNDVDAVLLTSYHCITY   55
|A8LQJ5|     MDGNTNVDDMLHVMEWHNGEKEFSPFSDTEMARRQNELRDWMAKNDVDASLFTSYHCINY   60
|A1B7I6|     ----------------------------MQRRQDDMRRWMAGNGVDAALFTSYHCINY    30
                                         *  ***  :.*  **.  * *** *:****** *

↓                  ↓
|Q9RHU9|     YSGWLYCYFGRKYGMVIDHNNATTISAGIDGGQPWRRSFGDNITYTDWRRDNFYRAVRQL  115
|A0A076WGB5| YSGWLYCYFGRKYGMVIDHNKATTISAGIDGGQPWRRSFGDNITYTDWRRDNFYQAVRQL  111
|X6DLM3|     YSGWLYCYFGRKYGMVIDQDNATTISAGIDGGQPYRRSFGDNITYTDWRRDNYYRAVRQL  115
|A6DVF8|     YSGWLYCYFGRKYGMVIDQKNATTISAGIDGGQPWRRTFGSNVTYTDWRRDNFYRAVQGL  115
|A3W1E4|     YSGWLYCYFGRKYGMVIDQKNATTISAGIDGGQPWRRTFGSNVTYTDWRRDNFYRAVQGL  115
|A1B0T5|     YSGWLYCYFGRKYGMVITQDAATTISAGIDGGQPWRRSFGGNVTYTDWRRDNYFRAVRQL  115
|A0A017HRV0| YSGWLYCQFGRRYGMIVTQDRALTVSAGIDGGQPWRRSFGDNITYTDWRRDNFYRAVRQN  115
|A3V128|     YSGWLYCYFGRKYGMVIDQKNATTISAGIDGGQPFRRSFGNNITYTDWRRDNFYRAIQQL  114
|V4RGE5|     YSGWLYCYFGRRYGMVITPDAATTISAGIDGGQPWRRTFGNNVTYTDWRRDNYYQAVRQL  120
|A6FQQ7|     YSGWLYCYFGRKYGMVIDQKTATTVSAGIDGGQPWRRSFGNNVTYTDWRRDNFYRAVQGL  115
|A8LQJ5|     YSGWLYCYFGRKYGMVIDQKNATTISAGIDGGQPFRRSFGNNITYTDWRRDNFYRAIQQL  120
|A1B7I6|     YSGWLYCYFGRKYGMVITQDAATTISAGIDGGQPWRRSFGGNVTYTDWRRDNYFRAVRQL   90
             ******* ***:***::.   .*  *:*********:**:**  *:*********:::*:.

⇓
|Q9RHU9|     TTGAKRIGIEFDHVNLDFRRQLEEALPGVEFVDISQPSMWWMRTIKSLEEQKLIREGARVC  175
|A0A076WGB5| TKGAKRVGIEFDHVSLDFRRQLEEALPGVEFVDVGQPSMWWMRTIKSAEEQKLIREGARVC  171
|X6DLM3|     TAGAKRVGIEFDHVNLDFRRQLEEALPGVEFIDIAQPSMWWMRSIKSVEEHTLIREGARVS  175
|A6DVF8|     TKGARRVGIEFDHVSLDYRQLLQDALPGVELVDVSQPSMWWMRTIKSAEEIKLITEGARIC  175
|A3W1E4|     TKGARRVGIEFDHVSLDYRQLLQDALPGVELVDVSQPSMWWMRTIKSAEEIKLITEGARIC  175
```

TABLE 1-continued

Alignment of creatinase enzymes of the invention

| | | |
|---|---|---|
| \|A1B0T5\| | TPGVKRLGIEFDHVNMDLRRQLEAALPGVEFVDVGQPSMWMRSIKSAEEHKLIREGARIC | 175 |
| \|A0A017HRV0\| | LPGVRRLGIEFDHVSLDFRRQLGEALPGVEFVDVGQPSMWMRTIKSEEERRLIREGARVC | 175 |
| \|A3V128\| | TPGAKRIGIEFDHVSLEYRQLLQDALPGVEFVDVGQPAMWMRTIKSAEEEIKLIKEGARVA | 174 |
| \|V4RGE5\| | LPGVRRLGIEFDHVSLDFRRDLEAALPGVEFVDVGQPSMWMRTIKSAEEQKLIREGARIC | 180 |
| \|A6FQQ7\| | TQGARRVGIEFDHVSLEYRDLLQDALPGVDFVDVSQPSMWMRTIKSDEEIKLIREGARVA | 175 |
| \|A8LQJ5\| | TPGAKRIGIEFDHVSLEYRQLLQDALPGVEFVDVGQPAMWMRTIKSAEEIKLIKEGARVA | 180 |
| \|A1B7I6\| | TPGVKRLGIEFDHVNMDLRRQLEAALPGVEFVDVGQPSMWMRSIKSAEEHKLIREGARIC | 150 |
| | *.:*:*******.:: * * ***** :::*:.::*   ****:. | |
| | ↓ | |
| \|Q9RHU9\| | DVGGAACAAAIKAGVPEHEVAIATTNAMIREIAKSFPFVELMDTWTWFQSGINTDGAHNP | 235 |
| \|A0A076WGB5\| | DVGGAACAAAVKAGVPEHEVAIATTNAMVREIAKSFPFVELMDTWTWFQSGINTDGAHNP | 231 |
| \|X6DLM3\| | DVGGAACVAAVKAGVPEHEVAIATTDAMIREIAKSHPFVELMDTWTWFQSGINTDGAHNP | 235 |
| \|A6DVF8\| | DVGGYAVAGAVKAGVPEHEVAIAGTNAMIREIAKSFPFVELMDTWTWFQSGINTDGAHNP | 235 |
| \|A3W1E4\| | DVGGYAVAGAVKAGVPEHEVAIAGTNAMIREIAKSFPFVELMDTWTWFQSGINTDGAHNP | 235 |
| \|A1B0T5\| | DVGGAAVAAAVKAGVPEHEVAIASTNAMIREIAASFPFVELMDTWTWFQSGINTDGAHNP | 235 |
| \|A0A017HRV0\| | DVGGAAVAEAVRAGVPEHEVAIASTNAMIREIARSFPYVELMDTWTWFQSGINTDGAHNP | 235 |
| \|A3V128\| | DVGGAAVAAAVKAGVPEHEVAIASTNAMIREIANSFPFVELMDTWTWFQSGINTDGAHNP | 234 |
| \|V4RGE5\| | DIGGEAVAKAVKAGVPEHEVAIAAANMIREIAESFPYVELMDTWTWFQSGINTDGAHNP | 240 |
| \|A6FQQ7\| | DVGGYAVAAAVQAGVPEHEVAIAGTNAMIREIAKSFPFVELMDTWTWFQSGINTDGAHNP | 235 |
| \|A8LQJ5\| | DVGGAAVAAAVKAGVPEHEVAIAGTTAMIREIANSFPFVELMDTWTWFQSGINTDGAHNP | 240 |
| \|A1B7I6\| | DVGGAAVAAAVKAGVPEHEVAIASTNAMIREVAASFPFVELMDTWTWFQSGINTDGAHNP | 210 |
| | *:** * . *:.********** * .:* *.*:********************* | |
| | ↓    ↓  ↓  ⇓ | |
| \|Q9RHU9\| | VTNRIVQSGDILSLNTFPMIFGYYTALERTLFCDHVDDASLDIWEKNVAVHRRGLELIKP | 295 |
| \|A0A076WGB5\| | VTNRIVQSGDILSLNTFPMIFGYYTALERTLFCDHVDDASLDIWEKNVAVHRRGLELIKP | 291 |
| \|X6DLM3\| | VTNRVVRAGDILSLNTFPMIFGYYTALERTLFCDHADDASLDVWQKNVAVHRRGLELIKP | 295 |
| \|A6DVF8\| | VTNRVVQSGDILSLNTFPMIFGYYTALERTLFCDHVDDASLDIWEKNVAVHRRGLELMKP | 295 |
| \|A3W1E4\| | VTNRVVQSGDILSLNTFPMIFGYYTALERTLFCDHVDDASLDIWEKNVAVHRRGLELMKP | 295 |
| \|A1B0T5\| | VTNKKIASGEILSLNCFPMIFGYYTALERTMFCDSVDDASLDIWEKNVAVHRRGLELIKP | 295 |
| \|A0A017HRV0\| | VTNRVVQSGDILSLNCFPMIFGYYTALERTMFCDHVDDASLDIWEKNVAVHRRGLELIRP | 295 |
| \|A3V128\| | VTNKKVQSGEILSLNTFPMIFGYYTALERTLFCDHVDDASLDIWEKNVKVHERGLELIKP | 294 |
| \|V4RGE5\| | VTNRVVQSGDILSLNCFPMIFGYYTALERTMFCDHVDDASLDVWEKNVAVHRRGLELIRP | 300 |
| \|A6FQQ7\| | VTNRVVQSGDILSLNTFPMIFGYYTALERTLFCDSVDDASLDVWEKNVAVHRRGLELMKP | 295 |
| \|A8LQJ5\| | VTNKKVQSGEILSLNTFPMIFGYYTALERTLFCDHVDDASLDIWEKNVKVHERGLQLIKP | 300 |
| \|A1B7I6\| | VTNKKIASGEILSLNCFPMIFGYYTALERTMFCDSVDDASLDIWEKNVAVHRRGLELIKP | 270 |
| | ***.  :  : *:******** ********:* .******:*:* .::* | |
| | ⇓ | ↓ |
| \|Q9RHU9\| | GARCKDIAIELNEMYREWDLLKYRSFGYGHSFGVLCHYYGREAGVELREDIDTELKPGMV | 355 |
| \|A0A076WGB5\| | GARCKDIALELNDMYREWDLLKYRSFGYGHSFGVLCHYYGREAGVELREDIDTVLEPGMV | 351 |
| \|X6DLM3\| | GVRCKDIAIELNEMYREWDLLKYRSFGYGHSFGVLCHYYGREAGVELREDIETVLEPGMV | 355 |
| \|A6DVF8\| | GARCMDIAIELNEMYREWDLLKYRSFGYGHSFGVLSHYYGREAGVELREDIDTVLKPGMV | 355 |
| \|A3W1E4\| | GARCMDIAIELNEMYRDWDLLKYRSFGYGHSFGVLSHYYGREAGVELREDIDTVLKPGMV | 355 |
| \|A1B0T5\| | GAKCNEIALELNDMYRQWDLLKYRSFGYGHSFGVLSHYYGREAGVELREDIETELKPGMV | 355 |
| \|A0A017HRV0\| | GAKCNEIAAELNEMYRQWDLLQYRSFGYGHSFGVLCHYYGREAGVELREDIDTELKPGMV | 355 |
| \|A3V128\| | GARCMDIAIELNEMYRDWDLLKYRSFGYGHSFGVLSHYYGREAGVELREDIETELKPGMV | 354 |
| \|V4RGE5\| | GKKCGEIAQELNQMYREWDLLQYRSFGYGHSFGVLSHYYGREAGVELREDIDTELKPGMV | 360 |
| \|A6FQQ7\| | GARCMDIAIELNEMYREWDLLKYRSFGYGHSFGVLSHYYGREAGVELREDIDTVLKPGMV | 355 |
| \|A8LQJ5\| | GARCMDIAIELNEMYREWDLLKYRSFGYGHSFGVLSHYYGREAGVELREDIETELKPGMV | 360 |
| \|A1B7I6\| | GAKCNEIALELNDMYRQWDLLKYRSFGYGHSFGVLSHYYGREAGVELREDIETELKPGMV | 330 |
| | * :* : *:*: ********.*************:* *:**** | |
| | ↓ | |
| \|Q9RHU9\| | VSMEPMVMLPEGMPGAGGYREHDILIVGEDG-AENITGFPFGPEHNIIRN- | 404 | SEQID 2 |
| \|A0A076WGB5\| | VSMEPMVMLPEGAPGAGGYREHDILIVKEDS-AENITGFPFGPEHNIIKN- | 400 | SEQID 6 |
| \|X6DLM3\| | VSMEPMVMLPEGTPGAGGYREHDILIVKDDG-AENITGFPFGPEHNIIRN- | 404 | SEQID 10 |
| \|A6DVF8\| | VSMEPMVMIPEGQPGAGGYREHDILVIGEDG-AENITGFPFGPEHNIVGKG | 405 | SEQID 14 |
| \|A3W1E4\| | VSMEPMVMIPEGQPGAGGYREHDILVIGEDG-AENITGFPFGPEHNIVGKG | 405 | SEQID 18 |
| \|A1B0T5\| | VSMEPMVMLPEGAPGAGGYREHDILIVTEDG-ADNITGFPFGPEHNIIRN- | 404 | SEQID 22 |
| \|A0A017HRV0\| | VSMEPMVMIPNGNPGAGGYREHDILIVTEDG-AENITKFPFGPEHNVIRN- | 404 | SEQID 26 |
| \|A3V128\| | VSMEPMVMIPEGQPGAGGYREHDILVIGEDNTVENITGFPFGPEHNVIKN- | 404 | SEQID 30 |
| \|V4RGE5\| | VSMEPMVMIPEGKPGAGGYREHDILIVTEDG-AENITGFPFGPEHNVIRN- | 409 | SEQID 34 |
| \|A6FQQ7\| | VSMEPMVMIPEGAPGAGGYREHDILVIGEDG-AENITGFPFGPEHNIVGSN | 405 | SEQID 38 |
| \|A8LQJ5\| | VSMEPMVMIPEGQPGAGGYREHDILVINDDNTVENITGFPFGPEHNIIKN- | 410 | SEQID 42 |
| \|A1B7I6\| | VSMEPMVMLPEGAPGAGGYREHDILIVTEDG-ADNITGFPFGPEHNIIRN- | 379 | SEQID 46 |
| | ********:*:* *************:: :*  .:*** *********::  . | | |

↓ = Active site residues of creatinase (EC 3.5.3.3)
⇓ = Mutation sites corresponding to residues C175A, C268L and C299A in SEQ ID No 2.

II. Methods for Producing the Mutant Creatinase (EC 3.5.3.3) of the Invention The invention further provides a genetically modified host cell comprising a gene encoding the mutant polypeptide of the invention. Host cells suitable for expression of the mutant polypeptide include a bacterial cell, a yeast cell and a fungal cell. Nucleic acid molecules encoding the mutant polypeptide can be made synthetically, and then restriction site cloned into the cloning site of an expression plasmid that can be transformed into the selected host cell. The nucleic acid molecule transformed into the host cell, may either be integrated into the host genome or may be retained on a self-replicating vector. The nucleic acid molecule encoding the mutant polypeptide maybe fused to a promoter that facilitates expression in the transformed host cell. The nucleic acid molecule may further encode the mutant polypeptide fused to a C-terminal or N-terminally fused amino acid sequence tag to facilitate purification of the expressed polypeptide. Suitable fusion amino acid sequence tags can e.g. be a bacterial fimbrial protein, e.g. the pilus components pilin and papA; protein A; the ZZ-peptide (ZZ-fusions are marketed by Pharmacia in Sweden); the maltose, cellulose or starch binding proteins/peptides (domains); glutathione S-transferase; (-galactosidase; or poly-histidine) and optionally a protease cleavage site for removal of such tag after purification.

The invention further provides a method for producing the mutant polypeptide of the invention, comprising the steps of: a) providing a recombinant host cell, wherein the cell comprises a DNA molecule, the DNA molecule comprising a nucleic acid sequence encoding the mutant polypeptide; b) incubating the host cell in a medium suitable for expression of the mutant polypeptide, and c) recovering the mutant polypeptide expressed by the host cell in step b) from the medium.

III Compositions Comprising the Mutant Creatinase (EC 3.5.3.3) of the Invention

In a further embodiment the invention provides a composition comprising *creatinase* (EC 3.5.3.3) and sarcosine oxidase (EC 1.5.3.1); or alternatively comprising *creatinase* (EC 3.5.3.3), creatininase (EC 3.5.2.10) and sarcosine oxidase (EC 1.5.3.1); wherein the *creatinase* is thermostable in the presence of isothiazolinone-derived agents; and wherein the amino acid sequence of the *creatinase* is as defined above in section I. The composition may be formulated as a dry powder, a tablet, or as a liquid.

IV a Sensor Suitable for the Measurement of Creatinine and/or Creatine in Samples of Physiological Fluids Comprising the Mutant Creatinase (EC 3.5.3.3) of the Invention The invention further provides a creatine sensor comprising *creatinase* (EC 3.5.3.3) and sarcosine oxidase (EC 1.5.3.1); or a creatinine sensor comprising *creatinase* (EC 3.5.3.3), creatininase (EC 3.5.2.10) and sarcosine oxidase (EC 1.5.3.1); or a dual sensor comprising both a creatine and creatinine sensors, wherein the *creatinase* enzyme is thermostable in the presence of isothiazolinone-derived agents; and wherein the amino acid sequence of the *creatinase* is as defined above in section I.

The sensor for determination of creatinine or creatine in a sample fluid comprises an electrode having a surface, wherein a plurality of enzymes for determination of creatinine or creatine are immobilized on the electrode surface, characterized in that one of the enzymes is a *creatine amidinohydrolase* is as defined above in section I.

V A Conventional Sensor Comprising the Mutant Creatinase (EC 3.5.3.3) of the Invention In one embodiment the sensor comprising the mutant *creatinase* is a conventional sensor, suitable for the measurement of creatinine in samples of physiological fluids. The conventional sensor comprises a dual sensor system composed of a creatine and the creatinine sensors that are built up as traditional amperometric sensors. FIG. 1 shows such a sensor 1, which is suited for mounting in an apparatus for measuring the concentration of analytes in a biological sample (e.g., an ABL™ 837 Blood Gas Analyzer (Radiometer Medical ApS, Copenhagen, Denmark)).

Basically, the sensor 1 comprises an electrode 2 onto which a membrane ring 3 is attached. The electrode 2 comprises a platinum anode 4 connected with a platinum wire 5, which, through a micro plug 6, is connected with a silver anode contact body 7. The platinum anode 4 and the lower part of the platinum wire 5 are sealed into a glass body 8. Between the glass body 8 and the micro plug 6, the platinum wire 5 is protected with heat-shrink tubing. A tubular silver reference electrode 10 encircles the upper part of the glass body 8 and extends the length of the electrode 2 to the anode contact body 7, which is fastened inside the reference electrode by means of a fixing body 11 and epoxy 12. The lower part of the glass body 8 is surrounded by an electrode base 13 whereto the membrane ring 3 is attached.

The upper part of the reference electrode 10 is surrounded by a plug part 14 for mounting the electrode 2 in the corresponding plug of an analysis apparatus (not shown) and for fixing a mantle 15. Gaskets 16 and 17 are placed between the electrode 2 and the mantle 15 in order to ensure that any electrolyte located at the measuring surface of the electrode 2 does not evaporate. The membrane ring 3, which is mounted at one end of the mantle 15, comprises a ring 20. A membrane 21 is stretched over the lower opening of the ring 20. This membrane 21 is shown in detail in FIG. 2.

Figure 2:
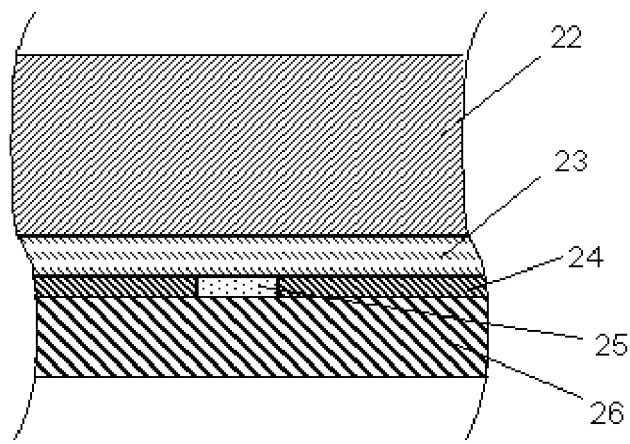
FIG. 2: illustrates the membrane of the sensor of FIG. 1.

FIG. 2 shows details of the membrane 21 which comprises five layers: a noise reducing spacer layer 22 facing the platinum anode 4 of the electrode 2, an interference limiting membrane layer 23, a gasket 24 encircling an enzyme layer 25, and a diffusion limiting porous membrane layer 26 which has been coated with a hydrophilic protection layer of polyurethane having a water content of around 80%. The coated membrane layer 26 faces the sample to be analysed.

The noise reducing spacer layer 22 may be about a 21±2 μm track-edged membrane of polyethylene terephthalate (PETP). The interference limiting membrane layer 23 may be about a 6±2 μm porous membrane of cellulose acetate (CA).

The gasket 24 may be a 30±5 μm double-sided adhesive disc having a center hole with a diameter of 1500 μm. The adhesive of the gasket 24 adheres to the interference limiting layer 23 and the diffusion limiting layer 26 to an extent that the enzymes are prevented from leaking out between the layers.

The enzyme layer 25 of the creatine sensor is typically an approximately 20 μm layer of *creatinase* and sarcosine oxidase cross-linked to glutaraldehyde (supplied by Kikkoman.co.jp) mixed with suitable additives, such as buffer. The enzyme layer 25 of the creatinine sensor is typically an approximately 20 μm layer of creatininase (supplied by Kikkoman.co.jp), *creatinase* and sarcosine oxidase cross-linked to glutaraldehyde mixed with suitable additives, such as buffer.

The diffusion limiting porous membrane layer 26 may be an approximately 12 μm layer of polyethyleneterephthalate (PETP) (pore diameter approximately 0.1 μm; pore density approximately $3 \cdot 10^7$ pores/cm$^2$), which has been coated with a polyurethane having a water content of about 80%.

In the creatinine sensor, both creatine and creatinine are enzymatically converted into hydrogen peroxide. In the creatine sensor, only creatine is enzymatically converted into hydrogen peroxide.

At the amperometric electrode, hydrogen peroxide is oxidized anodically at +675 mV against Ag/AgCl. The resulting current flow is proportional to the creatinine/creatine concentration in the sample. The concentration of creatinine is determined from the difference between the creatinine sensor signal (detecting creatine+creatinine) and the creatine sensor signal (detecting creatine).

VI A Thick-Film Sensor Comprising the Mutant Creatinase (EC 3.5.3.3) of the Invention In one embodiment the sensor comprising the mutant *creatinase* is a thick-film sensor, suitable for the measurement of creatinine in samples of physiological fluids. The thick-film sensor is composed of a dual sensor system comprising a creatine and a creatinine sensor that are built up as illustrated in FIG. 3.

Figure 3:
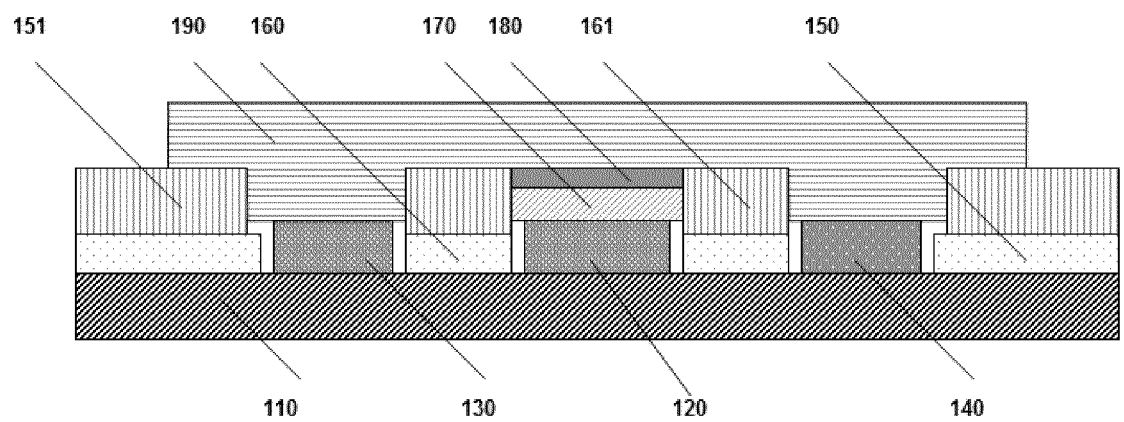
FIG. 3: illustrates an exemplary planar, thick-film sensor construction.

Referring to FIG. 3, an alumina substrate 110 of a thickness of 200 μm is provided at one surface with a circular platinum working electrode 120 of a diameter 1000 μm and a thickness of 10 μm, an annular platinum counter electrode 130 of an outer diameter 3000 μm, an inner diameter 2000 μm and a thickness of 10 μm, covering the angular range 30-3300 of the outer periphery of the working electrode, and a circular silver/silver chloride reference electrode 140 of a diameter 50 μm, positioned at the outer periphery of the working electrode at 0°. All of these three electrode structures are connected to the sensor electronics (not shown) across the alumina substrate 110 via platinum filed through holes (not shown) traversing the substrate. Upon operation, the working electrode 120 is polarised to +675 mV vs. the reference electrode 140.

Further on the alumina substrate 110 are two-layered structures of glass and polymer encapsulant. These two-layered structures include an annular structure 160, 161 of an outer diameter 1800 μm, an inner diameter 1200 μm and a thickness of 50 μm surrounding the working electrode 120 and a structure 150, 151 of a thickness 50 μm surrounding the complete electrode system. Both of these two-layered structures consist of an inner layer 150, 160 facing the alumina substrate 110 of ESL glass 4904 from ESL Europe of the United Kingdom of a thickness of 20 μm, and an outer layer 151, 161 of polymer encapsulant from SenDx Medical Inc. of California, USA as disclosed in international patent application WO97/43634 to SenDx Medical Inc. of California, USA which comprises 28.1% by weight of polyethylmethacrylate (Elvacite, part number 2041, from DuPont), 36.4% by weight of carbitol acetate, 34.3% by weight of silanised kaolin (part number HF900 from Engelhard), 0.2% by weight of fumed silica and 1.0% by weight of trimethoxysilane.

A circular inner membrane 170 of cellulose acetate and cellulose acetate butyrate of a diameter 1200 μm and a thickness of 10 μm covers the working electrode 120. For the creatinine sensor, a circular enzyme layer 180 of creatininase, glutaric aldehyde-treated *creatinase* and sarcosine oxidase, having a diameter 1200 μm and a thickness of 12 μm, covers the inner membrane 170.

For the creatine sensor, a circular enzyme layer 180 of glutaric aldehyde-treated *creatinase* and sarcosine oxidase, having a diameter 1200 μm and a thickness of 12 μm, covers the inner membrane 170.

A circular outer membrane layer 190 of acrylate (diffusion limiting membrane), having a diameter 4000 μm and a thickness of approximately 10 μm, covers the complete electrode system, centered onto the working electrode 120.

The outer membrane was prepared from a diluted dispersion of polyacrylate (Eudragit) dispersion was dispensed on the sensor area to cover all three electrodes and to have an approx. 0.5 mm overlap with the polymer encapsulant 151. In the creatinine sensor, both creatine and creatinine are enzymatically converted into hydrogen peroxide. In the creatine sensor, only creatine is enzymatically converted into hydrogen peroxide. The concentration of creatinine is determined from the difference between the creatinine sensor signal (representing creatine+creatinine) and the creatine sensor signal (representing creatine).

VII A Method for Measurement of Creatinine or Creatine in Samples of Physiological Fluids Using the Mutant Creatinase (EC 3.5.3.3) of the Invention The invention further provides a method for measurement of creatine and/or creatinine in a sample, comprising the step of contacting a sample with a sensor or a dual sensor comprising a *creatinase* enzyme (EC 3.5.3.3) that is thermostable in the presence of isothiazolinone-derived agents, and detecting creatine and/or creatinine in the sample. The creatine and/or creatinine detected by the sensor is then used to determine the level of the detected creatine and/or creatinine in the sample. In one embodiment, the method includes the step of contacting the sensor with a rinse solution comprising a thiol-interactive agent, such as isothiazolinone-derived agents (e.g. MIT), and wherein the rinse step may take place either before, after, or before and after the step of contacting a sample with the sensor or the dual sensor. The method for measurement of creatine and/or creatinine in a sample and the rinse step, is normally performed at a temperature of 37° C., but may be performed at temperatures above 25° C. (such as at, or above 26, 27, 28, 29, 30, 31, 32, 33, 34, 35, 36, 37, 38, 39, 40, 41, 42 or 45° C.).

In one embodiment of the method, the sensor comprises *creatinase* (EC 3.5.3.3) and sarcosine oxidase (EC 1.5.3.1) for measurement of creatine; and in a second embodiment of the method the sensor comprises *creatinase* (EC 3.5.3.3), creatininase (EC 3.5.2.10) and sarcosine oxidase (EC 1.5.3.1) for measurement of creatinine; or in a third embodiment of the method the sensor is a dual sensor comprising both said creatine and creatinine sensors. In a further embodiment of the method, wherein the *creatinase* enzyme is a mutant *creatinase*; and wherein the amino acid sequence of the *creatinase* is as defined above in section I.

VII Use of the Mutant Creatinase (EC 3.5.3.3) of the Invention in a Creatinine or Creatine Sensor with Enhanced Stability in the Presence of a Thiol-Interactive Agent at 37° C. and Above.

The invention further provides for the use of a *creatinase* enzyme (EC 3.5.3.3) that is thermostable in the presence of a thiol-interactive agent (e.g. a isothiazolinone-derived agents such as MIT), in a sensor suitable for determination of creatinine in combination with a rinse solution comprising a thiol-inactivating agent, wherein the life-time of the sensor at temperatures of about 37° C. and above is extended.

The *creatinase* enzyme may furthermore be used in either: a) a creatine sensor comprising *creatinase* (EC 3.5.3.3) and sarcosine oxidase (EC 1.5.3.1); b) a creatinine sensor comprising *creatinase* (EC 3.5.3.3), creatininase (EC 3.5.2.10) and sarcosine oxidase (EC 1.5.3.1); or c) a dual sensor comprising both a creatine and creatinine sensors, wherein the *creatinase* enzyme is thermostable in the presence of isothiazolinone-derived agents; and wherein the amino acid sequence of the *creatinase* is as defined above in section I.

Example 1: Method for Producing a *creatine amidinohydrolase* that Both Retains Activity in the Presence of Reagents that Modify Thiol Groups and has Enhanced Thermostability The native *creatinase* enzyme from *Alcaligenes* sp (Q9RHU9_Uniprot) was selected as the "wild-type" parent enzyme since it is known to be inherently thermostable.

Mutant polypeptides derived from the *Alcaligenes* sp (Q9RHU9_Uniprot) *creatinase* were produced in recombinant microbial cells transformed with a synthetic transgene encoding the desired mutant (supplied to order by GenScript).

Cysteine residues present in the native *creatinase* enzyme (Q9RHU9_Uniprot) were selected for mutation, on the grounds that these residues are a potential target for SH reagents attacking thiol groups that might compromise *creatinase* activity. A number of substitutions for each cysteine residue were tested, starting from conservative substitutions such as alanine, serine and threonine residues. Accordingly a series of mutant *creatinase* polypeptides were produced comprising one, two, three or more substitutions of cysteine residues in a given mutant polypeptide. The expressed and purified mutant polypeptides were then tested for their stability (in terms of retained *creatinase* enzyme activity) following incubation of 0.2 mg/ml enzyme in a 100 mM phosphate buffer pH 7.4 without the preservative Neolone as well as a rinse solution for ABL90 analyzers (Radiometer Medical aps) containing 1.25 g/L Neolone and incubated at either 4° C., 22° C. (RT) or 40° C., over a period of 8 days (or 4 days as indicated). The rinse solution for ABL90 analyzers was a buffered saline solution with pH 7.4 preserved with 1.25 g/L Neolone (comprising MIT).

After incubation residual activity of the samples were determined after diluting all samples 10 times in a 100 mM phosphate buffer pH 7.5. 100 μl of each diluted sample was pipetted in duplicate in a microwell plate followed by 100 μl of a 60 mM phosphate buffer pH 7.5 containing 50 mM creatine, 10 U/ml sarcosine oxidase, 5 U/ml horse radish peroxidase, 0.04% 4-hydroxybenzenesulphonate and 1.5 mM 4-aminoantipyrine. Formation of the colored product formed by oxidation of 4-hydroxybenzenesulphonate subsequently reacting with 4-aminoantipyrine is followed in a micro-well reader thermostated to 25° C. by increase in absorbance at 490 nm (ΔAbs). ΔAbs/minute taken over the linear part of the progress curve is used as a measure of the relative *creatinase* activity.

The stability of the mutant polypeptides (% retained activity relative to activity after incubation at 4° C.) was compared with the wild-type parent enzyme and a commercially available recombinant thermostable *creatinase*, C2-AT (supplied by Kikkoman.co.jp). The determined amino acid sequence of *creatinase*, C2-AT was found to be identical to the sequence of *Alcaligenes creatinase* Q9RHU9 with the exception of having two amino acid substitutions: A202T and E312K.

TABLE 2

Test results for stability of creatinase mutants

| Creatinase | Buffer 4° C. | Buffer RT | Buffer 40° C. | Rinse 4° C. | Rinse RT | Rinse 40° C. |
|---|---|---|---|---|---|---|
| Wt | 100 | 88.6 | 81.5 | 100 | 81.6 | −0.2 |
| C175A | 100 | 98.8 | 59.7 | 100 | 99.7 | −0.1 |
| C175T | 100 | 91.3 | 23.7 | 100 | 62.9 | −0.4 |
| C175G | 100 | 95.8 | 69.1 | 100 | 63.8 | −0.2 |
| C299A | 100 | 101.5 | 12.8 | 100 | 99.7 | 0.1 |
| C299S | 100 | 94.3 | 11.2 | 100 | 65.2 | 0.6 |
| C175A, C182T | 100 | 98.6 | 83.3 | 100 | 84.8 | −0.4 |
| C52N, C175A | 100 | 100.5 | 69.1 | 100 | 89.5 | −0.1 |
| C175A, C268L | 100 | 99.0 | 100.4 | 100 | 93.8 | 2.9 |
| C175A, C299A | 100 | 96.3 | 70.7 | 100 | 100.6 | 54.2 |

TABLE 2-continued

Test results for stability of creatinase mutants

| Creatinase | Buffer 4° C. | Buffer RT | Buffer 40° C. | Rinse 4° C. | Rinse RT | Rinse 40° C. |
|---|---|---|---|---|---|---|
| C175S, C299S | 100 | 72.3 | 9.0 | 100 | 44.4 | 7.9 |
| E312K | 100 | 101.1 | 81.4 | 100 | 86.9 | 0.0 |
| A202T* | 100 | 101.5 | 99.7 | 100 | 76.3 | 0.2 |
| A202T, C299T, E312K | 100 | 97.6 | 31.0 | 100 | 107.0 | 0.6 |
| A202T, C299G, E312K | 100 | 95.0 | 32.0 | 100 | 106.1 | 0.4 |
| C175A, A202T, E312K | 100 | 95.1 | 78.5 | 100 | 99.8 | 1.8 |
| C299A, E312K, A202T | 100 | 100.4 | 42.9 | 100 | 101.9 | 11.6 |
| C175A, C299A, E312K, A202T | 100 | 94.7 | 44.1 | 100 | 96.6 | 51.8 |
| C175A, C268L, C299A | 100 | 89.0 | 61.9 | 100 | 100.0 | 63.5 |
| C2-AT, Kikkoman | 100 | 94.6 | 88.3 | 100 | 81.0 | 2.4 |

*4 days treatment

Substituting all cysteine residues in *Alcaligenes creatinase* with serine led to a complete loss of enzyme activity (not shown). A conservative substitution of some of the cysteine residues led to improved stability towards MIT at room temperature of 22° C. A comparison of alternative conservative substitutions of cysteine residues surprisingly revealed that substitution with alanine confers the greatest stability towards MIT. For example substitution of C175 as well as C299 with either threonine, glycine or serine failed to enhance stability towards MIT. However, mutant enzymes with a single cysteine substitution, while showing enhanced stability towards MIT at room temperature, exhibited a loss of enzyme stability at 40° C.

Mutant *Alcaligenes creatinase* polypeptides comprising a number of different combinations of two cysteine substitutions were tested; of which the specific combination of C299A, C175A substitutions conferred the greatest stability towards isothiazolinones while at the same time retaining thermostability at 40° C. Additionally, a third conservative cysteine substitution, C268L, when inserted in a mutant having the double substitution (C299A, C175A), was found to confer a further increase in stability at 40° C. towards isothiazolinones. The two amino acid substitutions A202T and E312K, alone or in combination with of C299A, C175A substitutions did not however confer any additional increase in stability at 40° C. towards isothiazolinones.

Creatinase enzymes derived from other microbial sources, that share a high degree of structural homology and the same functional properties with the native *creatinase* enzyme from *Alcaligenes* sp (Q9RHU9_Uniprot) were identified, based on their sharing an amino acid sequence identity of greater than 80%, and being assigned *creatinase* activity of EC 3.5.3.3. The amino acid sequence of each of the selected *creatinase* enzymes were aligned with the amino acid sequence (SEQ ID No 2) of the native *creatinase* enzyme from *Alcaligenes* sp (Q9RHU9_Uniprot), and the substitutions corresponding to C299A, C175A and optionally C268L in SEQ ID No 2, were identified (see Table 1), that are sufficient to confer increased stability at up to 40° C. towards isothiazolinones in each respective enzyme.

Example 2: The Effective Lifetime of a Creatinine Sensor is Enhanced by Employing a *creatine amidinohydrolase* that Retains Activity in the Presence of Reagents that Modify Thiol Groups and has Enhanced Thermostability Creatine and creatinine sensors were produced with *creatinase* mutant #42 (C175A, A202T, C299A, E312K) as well as the commercial *creatinase* C2-AT from Kikkoman. The sensors were placed in sensor cassettes for the Radiometer ABL90 analyzer, mounted in an analyzer thermostated at 37° C. with a rinse solution containing 0.7 g/L Neolone 950 with 9% methylisothiazolinone (MIT). The analyzers were running for 8 days under standard analyser condition to ensure functionality and stable responses. On day 9 the analyzers were divided into two groups (A and B each consisting of three analyzers with mutant #42 CI enzyme and two analyzers with commercial CI, C2-AT. To group A was applied a rinse solution with 1.2 g/L Neolone 950 and to group B was applied a rinse solution with 2 g/L Neolone 950. The analyzers were then running with standard rinsing and calibration for further 36 days. The decrease in sensitivity of the sensors during these 36 days is summarized in the table:

|  | average ΔS [pA/µM], 36 days | | | |
|---|---|---|---|---|
|  | A. 1.2 g/L Neolone | | B. 2 g/L Neolone | |
|  | Mut.#42 | C2-AT | Mut.#42 | C2-AT |
| Creatininase 3-enzyme sensor | −4.57 | −9.54 | −6.22 | −12.35 |
| Creatinase 2-enzyme sensor | −4.38 | −10.2 | −6.38 | −10.72 |

Acceptable sensitivity loss over a sensor lifetime is approx. 10 pA/µM.

At both levels of the preservative Neolone 950 the reduction in sensitivity over 36 days is significantly lower with the CI mutant #42 compared to the commercial enzyme.

The invention claimed is:

1. A mutant polypeptide having *creatine amidinohydrolase* activity, wherein the polypeptide is selected from the group consisting of:
   a. a polypeptide comprising an amino acid sequence having at least 80% identity to SEQ ID No: 2; wherein amino acid residue cysteine at position 175 is substituted with alanine and amino acid residue cysteine at position 299 is substituted with alanine, and
   b. a polypeptide having an amino acid sequence selected from among SEQ ID No 3 (corresponding to *Alcaligenes* sp. *creatine amidinohydrolase*—Uniprot: Q9RHU9 with substitutions: C175A+C299A); SEQ ID No 7 (corresponding to *Ochrobactrum anthropic creatinase*—Uniprot: A0A076WGB5 with substitutions: C171A+C295A); SEQ ID No 11 (corresponding to *Mesorhizobium* sp. LNHC221B00 *creatinase*—Uniprot: X6DLM3 with substitutions: S175A+C299A); SEQ ID No 15 (corresponding to *Roseovarius* sp TM1035 *creatinase*—Uniprot: A6DVF8 with substitutions: C175A+C299A); SEQ ID No 19 (corresponding to *Roseovarius* sp 217 *creatinase*—Uniprot: A3W1E4 with substitutions: C175A+C299A); SEQ ID No 23 (corresponding to *Paracoccus denitrificans creatinase*—Uniprot: A1BOT5 with substitutions: C175A+C299A); SEQ ID No 27 (corresponding to *Rubellimicrobium mesophilum creatinase*—Uniprot: A0A017HRV0 with substitutions: C175A+C299A); SEQ ID No. 31 (corresponding to *Loktanella vestfoldensis* SKA53 *creatinase*—Uniprot: A3V128 with substitutions: C298A); SEQ ID No. 35 (corresponding to *Lutibaculum baratangense* AMV1 *creatinase*—Uniprot: V4RGE5 with substitutions: C180A+C304A); SEQ ID No. 39 (corresponding to *Roseobacter* sp. AzwK-3b *creatinase*—Uniprot: A6FQQ7 with substitution: C299A); SEQ ID No. 43 (corresponding to *Dinoroseobacter shibae creatinase*—Uniprot: A8LQJ5 with substitution: C304A); SEQ ID No. 47 (corresponding to *Paracoccus denitrificans creatinase*—Uniprot: A1B7I6 with substitution: C150A+C274A).

2. The mutant polypeptide having *creatine amidinohydrolase* activity according to claim 1, wherein the polypeptide comprises:
   a. an amino acid sequence having at least 80% identity to SEQ ID No: 2; wherein the amino acid residue corresponding to the cysteine at position 175 in SEQ ID No: 2 is alanine, and the amino acid residue corresponding to the cysteine at position 299 in SEQ ID No: 2 is alanine and the amino acid residue corresponding to the cysteine at position 268 in SEQ ID No: 2 is selected from leucine, valine, isoleucine or alanine; or
   b. an amino acid sequence selected from among SEQ ID No 4 (corresponding to *Alcaligenes* sp. *creatine amidinohydrolase*—Uniprot: Q9RHU9 with substitutions: C175A+C299A+C268L); SEQ ID No 8 (corresponding to *Ochrobactrum anthropic creatinase*—Uniprot: A0A076WGB5 with substitutions: C171A+C295A+C264L); SEQ ID No 12 (corresponding to *Mesorhizobium* sp. LNHC221B00 *creatinase*—Uniprot: X6DLM3 with substitutions: S175A+C299A+C268L); SEQ ID No 16 (corresponding to *Roseovarius* sp TM1035 *creatinase*—Uniprot: A6DVF8 with substitutions: C175A+C299A+C268L); SEQ ID No 20 (corresponding to *Roseovarius* sp 217 *creatinase*—Uniprot: A3W1E4 with substitutions: C175A+C299A+C268L); SEQ ID No 24 (corresponding to *Paracoccus denitrificans creatinase*—Uniprot: A1BOT5 with substitutions: C175A+C299A+C268L); SEQ ID No 28 (corresponding to *Rubellimicrobium mesophilum creatinase*—Uniprot: A0A017HRV0 with substitutions: C175A+C299A+C268L); SEQ ID No. 32 (corresponding to *Loktanella vestfoldensis* SKA53 *creatinase*—Uniprot: A3V128 with substitutions: C298A+C267L); SEQ ID No. 36 (corresponding to *Lutibaculum baratangense* AMV1 *creatinase*—Uniprot: V4RGE5 with substitutions: C180A+C304A+C273L); SEQ ID No. 40 (corresponding to *Roseobacter* sp. AzwK-3b *creatinase*—Uniprot: A6FQQ7 with substitution: C299A+C268L); SEQ ID No. 44 (corresponding to *Dinoroseobacter shibae creatinase*—Uniprot: A8LQJ5 with substitution: C304A+C273L); SEQ ID No. 48 (corresponding to *Paracoccus denitrificans creatinase*—Uniprot: A1B7I6 with substitution: C150A+C274A+C243L).

3. An isolated polynucleotide comprising a nucleotide sequence which encodes the mutant polypeptide of claim 1.

4. A nucleic acid construct comprising the polynucleotide of claim 3 operably linked to one or more control sequences that direct the production of the mutant polypeptide in an expression host.

5. A genetically modified host cell comprising a nucleic acid construct encoding the mutant polypeptide of claim 1, wherein said cell is selected from a bacterial cell, a yeast cell, and a fungal cell.

6. A method for producing the mutant polypeptide of claim 1, comprising the steps of:
   a. providing a recombinant host cell, wherein the cell comprises a DNA molecule, the DNA molecule comprising a nucleic acid sequence encoding the mutant polypeptide according to claim 1,
   b. incubating the host cell under conditions suitable for expression of the mutant polypeptide, and
   c. recovering the mutant polypeptide expressed by the host cell in step b).

7. A composition comprising the mutant polypeptide according to claim 1, wherein the composition is formulated as a dry powder, a tablet, or as a liquid.

8. The composition according to claim 7, further comprising:
   a. a sarcosine oxidase (EC 1.5.3.1); or
   b. a creatininase (EC 3.5.2.10) and sarcosine oxidase (EC 1.5.3.1).

9. A sensor for determination of creatinine and/or creatine in a sample fluid comprising at least one electrode having a surface, and a plurality of enzymes immobilized on the at least one electrode surface, and wherein at least one of the enzymes is the mutant polypeptide according to claim 1.

10. A sensor for determination of creatinine and/or creatine according to claim 9, wherein the sensor is selected from:
   a. a creatine sensor comprising *creatinase* (EC 3.5.3.3) and sarcosine oxidase (EC 1.5.3.1);
   b. a creatinine sensor comprising *creatinase* (EC 3.5.3.3), creatininase (EC 3.5.2.10) and sarcosine oxidase (EC 1.5.3.1); and
   c. a dual sensor comprising both the creatine sensor (a) and the creatinine sensor (b).

11. A method for producing a sensor for determination of creatinine and/or creatine in a sample fluid, comprising the step of depositing an aqueous mixture containing a plurality of enzymes on a surface of an electrode; wherein at least one of the enzymes is a mutant polypeptide according to claim 1.

12. A method for determination of creatinine and/or creatine in a sample of physiological fluid derived from a subject comprising the steps of:
   a. contacting a sensor or a dual sensor with the sample;
   b. detecting creatine and/or creatinine in the sample; and a rinse step comprising:
   c. contacting the sensor with a rinse solution comprising a thiol-interactive agent, wherein the rinse step (c) is either before step (a), after step (b), or both before step (a) and after step (b); wherein the method is performed at a temperature of above 25° C.; and wherein the sensor comprises an electrode having a surface, and a plurality of enzymes immobilized on the electrode surface, and wherein at least one of the enzymes is the mutant polypeptide according to claim 1.

13. A method for determination of creatinine and/or creatine according to claim 12, wherein the sensor is selected from:
   a. a creatine sensor comprising *creatinase* (EC 3.5.3.3) and sarcosine oxidase (EC 1.5.3.1);
   b. a creatinine sensor comprising *creatinase* (EC 3.5.3.3), creatininase (EC 3.5.2.10) and sarcosine oxidase (EC 1.5.3.1); and
   c. a dual sensor comprising both the creatine sensor (a) and the creatinine sensor (b).

14. The method of claim 12, wherein the mutant polypeptide is in a composition formulated as a dry powder, a tablet, or as a liquid.

15. The method of claim 14, wherein the composition further comprises:
   a. a sarcosine oxidase (EC 1.5.3.1); or
   b. a creatininase (EC 3.5.2.10) and sarcosine oxidase (EC 1.5.3.1).

* * * * *